United States Patent
Uda et al.

(10) Patent No.: US 10,633,429 B2
(45) Date of Patent: Apr. 28, 2020

(54) HUMAN ANTIBODY κ TYPE LIGHT CHAIN COMPLEX-CONTAINING COMPOSITION AND METHOD FOR PRODUCING SAME

(71) Applicant: JAPAN SCIENCE AND TECHNOLOGY AGENCY, Kawaguchi-shi, Saitama (JP)

(72) Inventors: Taizo Uda, Oita (JP); Emi Hifumi, Oita (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 551 days.

(21) Appl. No.: 14/912,444

(22) PCT Filed: Aug. 13, 2014

(86) PCT No.: PCT/JP2014/071379
§ 371 (c)(1),
(2) Date: Feb. 17, 2016

(87) PCT Pub. No.: WO2015/025786
PCT Pub. Date: Feb. 26, 2015

(65) Prior Publication Data
US 2019/0256576 A1    Aug. 22, 2019

(30) Foreign Application Priority Data
Aug. 20, 2013 (JP) ................. 2013-170414

(51) Int. Cl.
C07K 16/00 (2006.01)
C12N 9/00 (2006.01)
A61K 39/00 (2006.01)

(52) U.S. Cl.
CPC ............ *C07K 16/00* (2013.01); *C12N 9/0002* (2013.01); *C07K 2317/21* (2013.01); *C07K 2317/56* (2013.01); *C07K 2317/73* (2013.01)

(58) Field of Classification Search
None
See application file for complete search history.

(56) References Cited

U.S. PATENT DOCUMENTS

| | | | |
|---|---|---|---|
| 5,236,825 A | 8/1993 | Iverson et al. | |
| 5,236,836 A | 8/1993 | Paul | |
| 2012/0322135 A1 | 12/2012 | Uda et al. | |
| 2013/0280244 A1 | 10/2013 | Sidera et al. | |

FOREIGN PATENT DOCUMENTS

| | | |
|---|---|---|
| JP | H04-504526 A | 8/1992 |
| JP | H05-508073 A | 11/1993 |
| JP | 2006-197930 A | 8/2006 |
| WO | 90/07934 A1 | 7/1990 |
| WO | 91/14769 A1 | 10/1991 |
| WO | WO-2005120557 A2 * | 12/2005 ......... C07K 16/2863 |
| WO | 2008/029807 A1 | 3/2008 |
| WO | 2008054471 A2 | 5/2008 |
| WO | 2011/102517 A1 | 8/2011 |
| WO | 2012/041863 A1 | 4/2012 |
| WO | 2013/133253 A1 | 9/2013 |

OTHER PUBLICATIONS

R. T. Radulescu "Antibody constant region: potential to bind metal and nucleic acid" Medical Hypotheses (1995) 44: 137-145 (Year: 1995).*
Lakhrif et al. "A method to confer Protein L binding ability to any antibdoy fragment" MABS 2106, 8(2); pp. 379-388 (Year: 2016).*
Heiko van der Kuip et al. "Short term culture of breast cancer tissues to study the activity of the anticancer drug taxol in an intact tumor environment" BMC cancer 2006, 6: 86, pp. 1-11 (Year: 2006).*
Uda T et al: "Catalytic Activity of Antibody Light Chain to gp41:A Consideration of Refolding in Relation to Activation Mechanism," Catalytic Antibodies, Paul S (ed), Chemical Immunology, S. Karger AG, CH, vol. 77, Jan. 1, 2000, pp. 18-32.
Hifumi E et al: "Highly efficient method of preparing human catalytic antibody light chains and their biological characteristics," The FASEB Journal, vol. 26, No. 4, Apr. 1, 2012, pp. 1607-1615.
Sidera K et al: "The 4C5 Cell-Impermeable Anti-HSP90 Antibody with Anti-Cancer Activity, Is Composed of a Single Light Chain Dimer," PLOS ONE, vol. 6, No. 9, Jan. 1, 2011, e23906, 9 pages.
Hifumi E et al: "Biochemical Features of a Catalytic Antibody Light Chain, 22F6, Prepared from Human Lymphocytes," Journal of Biological Chemistry, vol. 288, No. 27, Jul. 5, 2013, pp. 19558-19568.
Kaplan B et al: "Immunoglobulin Free Light Chain Dimers in Human Diseases," The Scientific World Journal, vol. 11, Jan. 1, 2011, pp. 726-735.
Hifumi E et al: "A novel method of preparing the monoform structure of catalytic antibody light chain," The FASEB Journal, vol. 30, No. 2, Nov. 2, 2015, pp. 895-908.
Communication Supplementary European Search Report dated Oct. 7, 2016 in connection with European Patent Application No. 14838038. 9, 6 pages.

(Continued)

Primary Examiner — Daniel E Kolker
Assistant Examiner — James L Rogers
(74) Attorney, Agent, or Firm — Amster, Rothstein & Ebenstein LLP

(57) ABSTRACT

A human antibody κ type light chain complex-containing composition includes a complex in which a human antibody κ type light chain is bound to one or more kinds of metal ions selected from the group consisting of Group 10 elements, Group 11 elements, and Group 12 elements. The human antibody κ type light chain is a dimer, cysteines at C terminals of two human antibody κ type light chains are bound to each other via the metal ion, and 0.1 mol or more of the metal ion is bound per 1 mol of the human antibody κ type light chain.

3 Claims, 11 Drawing Sheets
Specification includes a Sequence Listing.

(56) References Cited

OTHER PUBLICATIONS

Derry C. Roopenian & Shreeram Akilesh., "FcRn: the neonatal Fc receptor comes of age", Nature Reviews Immunology, vol. 7, pp. 715-725 (Sep. 2007).
Emi Hifumi et al., Mokuhyo Tanpakushitsu de aru HIVgp41 o Hakai suru 'SuperKotai Koso' no Kakushu Seishitsu to Koso Kassei Hatsugen Kiko no Kaiseki, Dai 10 Kai Symposium on Polymers and Biosciences, vol. 10, pp. 31-32 (Jul. 2000).
International Search Report received for PCT Patent Application No. PCT/JP2014/071379 dated Nov. 18, 2014, 4 pages (2 pages of English Translation of International Search Report, 2 pages of International Search Report).
Written Opinion received for PCT Patent Application No. PCT/JP2014/071379 dated Nov. 18, 2014, 5 pages.

\* cited by examiner

HUMAN ANTIBODY κ TYPE LIGHT CHAIN COMPLEX-CONTAINING COMPOSITION AND METHOD FOR PRODUCING SAME

CROSS-REFERENCE TO RELATED APPLICATIONS

This application is a U.S. national stage entry under 35 U.S.C. § 371 of PCT International Patent Application No. PCT/JP2014/071379, filed Aug. 13, 2014, which claims the benefit of Japanese Patent Application No. 2013-170414, filed Aug. 20, 2013, the contents of which are incorporated herein by reference into the subject application.

TECHNICAL FIELD

The present invention relates to a human antibody κ type light chain-containing composition having high activity and excellent stability, and a method of producing the same.

Priority is claimed on Japanese Patent Application No. 2013-170414, filed Aug. 20, 2013, the content of which is incorporated herein by reference.

BACKGROUND ART

An antibody is composed of a heavy chain (H chain) and a light chain (L chain). The heavy chain and light chain are composed of a variable region (VR) and a constant region (CR). The variable region has a complementarity-determining region (CDR). Further, the light chains of the antibody are classified into κ-type light chains and λ-type light chains.

In recent years, an antibody having enzyme-like activity, that is, an abzyme, has attracted considerable attention. Such an abzyme is expected to be used in many fields, such as the medical field, and chemical and food industries, because it has both high molecular recognition ability and enzymatic activity of an antibody. In particular, an abzyme having high specificity to a target molecule and which is capable of exhibiting cytotoxicity against the target molecule by enzymatic activity is expected to be used as an effective anti-cancer drug having few side effects. Particularly, since a human abzyme is expected to cause few side effects when it is administered to the human body, domestic and foreign pharmaceutical companies have been waiting for the development of useful human abzymes.

The present inventors have carried out various types of original research relating to abzymes (for example, refer to PTL 1). Among them, in PTL 2, an abzyme composed of a human antibody κ type light chain having antiviral activity against rabies virus or influenza virus has been reported.

CITATION LIST

Patent Literature

[PTL 1] Japanese Unexamined Patent Application, First Publication No. 2006-197930
[PTL 2] PCT International Publication No. WO 2011/102517

SUMMARY OF INVENTION

Technical Problem

In order to clinically use an abzyme as a pharmaceutical product, it is important to stably mass-produce an abzyme having sufficient activity. However, when many abzymes are artificially synthesized by an intracellular or extracellular expression system using a genetic recombination technique, there is a problem in that performance is not stable, and the difference between lots is large.

A main object of the present invention is to provide an abzyme composed of a human antibody light chain and having higher activity, and a method of stably producing the abzyme.

Solution to Problem

The present inventors have found that a composition containing a human antibody light chain and having higher activity can be stably obtained by incubating a human antibody light chain with one or more metal ions selected from the group consisting of Group 10 elements, Group 11 elements, and Group 12 elements. Based on the findings, the present invention was completed.

That is, a human antibody κ type light chain complex-containing composition, and a method of producing the same are described in the following [1] to [11].

[1] A human antibody κ type light chain complex-containing composition, comprising: a complex in which a human antibody κ type light chain is bound to one or more kinds of metal ions selected from the group consisting of Group 10 elements, Group 11 elements, and Group 12 elements, in which the human antibody κ type light chain is a dimer, and cysteines at C terminals of two human antibody κ type light chains are bound to each other via the metal ion, and in which 0.1 mol or more of the metal ion is bound per 1 mol of the human antibody κ type light chain.

[2] The human antibody κ type light chain complex-containing composition according to [1], in which the metal ion is one or more selected from the group consisting of copper ion, nickel ion, zinc ion, gold ion, silver ion, and platinum ion.

[3] The human antibody κ type light chain complex-containing composition according to Claim 1 or 2, in which the human antibody κ type light chain is selected from the group consisting of: (1) a polypeptide in which a variable region is represented by an amino acid sequence of SEQ ID NO. 1 or an amino acid sequence obtained by substituting, adding or deleting one or several amino acids in the amino acid sequence; (2) a polypeptide in which a variable region is represented by an amino acid sequence of SEQ ID NO. 3 or an amino acid sequence obtained by substituting, adding or deleting one or several amino acids in the amino acid sequence; (3) a polypeptide in which a variable region is represented by an amino acid sequence of SEQ ID NO. 5 or an amino acid sequence obtained by substituting, adding or deleting one or several amino acids in the amino acid sequence; (4) a polypeptide in which a variable region is represented by an amino acid sequence of SEQ ID NO. 7 or an amino acid sequence obtained by substituting, adding or deleting one or several amino acids in the amino acid sequence; (5) a polypeptide in which a variable region is represented by an amino acid sequence of SEQ ID NO. 9 or an amino acid sequence obtained by substituting, adding or deleting one or several amino acids in the amino acid sequence; (6) a polypeptide in which a variable region is represented by an amino acid sequence of SEQ ID NO. 11 or an amino acid sequence obtained by substituting, adding or deleting one or several amino acids in the amino acid sequence; (7) a polypeptide in which a variable region is represented by an amino acid sequence of SEQ ID NO. 13 or an amino acid sequence obtained by substituting, adding or deleting one or several amino acids in the amino acid sequence; (8) a polypeptide in which a variable region is represented by an amino acid sequence of SEQ ID NO. 15 or an amino acid sequence obtained by substituting, adding or deleting one or several amino acids in the amino acid sequence; (9) a polypeptide in which a variable region is represented by an amino acid sequence of SEQ ID NO. 17 or an amino acid sequence obtained by substituting, adding or deleting one or several amino acids in the amino acid sequence; (10) a polypeptide in which a variable region is represented by an amino acid sequence of SEQ ID NO. 19 or an amino acid sequence obtained by substituting, adding or deleting one or several amino acids in the amino acid sequence; (11) a polypeptide in which a variable region is represented by an amino acid sequence of SEQ ID NO. 21 or an amino acid sequence obtained by substituting, adding or deleting one or several amino acids in the amino acid sequence; (12) a polypeptide in which a variable region is represented by an amino acid sequence of SEQ ID NO. 23 or an amino acid sequence obtained by substituting, adding or deleting one or several amino acids in the amino acid sequence; (13) a polypeptide in which a variable region is represented by an amino acid sequence of SEQ ID NO. 25 or an amino acid sequence obtained by substituting, adding or deleting one or several amino acids in the amino acid sequence; (14) a polypeptide in which a variable region is represented by an amino acid sequence of SEQ ID NO. 27 or an amino acid sequence obtained by substituting, adding or deleting one or several amino acids in the amino acid sequence; (15) a polypeptide which is represented by an amino acid sequence in which $219^{th}$ cysteine in an amino acid sequence of SEQ ID NO. 2 is substituted with alanine or by an amino acid sequence obtained by substituting, adding or deleting one or several amino acids in the amino acid sequence; (16) a polypeptide in which a variable region is represented by an amino acid sequence of SEQ ID NO. 29 or an amino acid sequence obtained by substituting, adding or deleting one or several amino acids in the amino acid sequence; (17) a polypeptide in which a variable region is represented by an amino acid sequence of SEQ ID NO. 31 or an amino acid sequence obtained by substituting, adding or deleting one or several amino acids in the amino acid sequence; (18) a polypeptide in which a variable region is represented by an amino acid sequence of SEQ ID NO. 33 or an amino acid sequence obtained by substituting, adding or deleting one or several amino acids in the amino acid sequence; (19) a polypeptide in which a variable region is represented by an amino acid sequence of SEQ ID NO. 35 or an amino acid sequence obtained by substituting, adding or deleting one or several amino acids in the amino acid sequence; (20) a polypeptide in which a variable region is represented by an amino acid sequence of SEQ ID NO. 37 or an amino acid sequence obtained by substituting, adding or deleting one or several amino acids in the amino acid sequence; (21) a polypeptide in which a variable region is represented by an amino acid sequence of SEQ ID NO. 39 or an amino acid sequence obtained by substituting, adding or deleting one or several amino acids in the amino acid sequence; (22) a polypeptide in which a variable region is represented by an amino acid sequence of SEQ ID NO. 41 or an amino acid sequence obtained by substituting, adding or deleting one or several amino acids in the amino acid sequence; (23) a polypeptide in which a variable region is represented by an amino acid sequence of SEQ ID NO. 43 or an amino acid sequence obtained by substituting, adding or deleting one or several amino acids in the amino acid sequence; (24) a polypeptide in which a variable region is represented by an amino acid sequence of SEQ ID NO. 45 or an amino acid sequence obtained by substituting, adding or deleting one or several amino acids in the amino acid sequence; (25) a polypeptide in which a variable region is represented by an amino acid sequence of SEQ ID NO. 47 or an amino acid sequence obtained by substituting, adding or deleting one or several amino acids in the amino acid sequence; (26) a polypeptide in which a variable region is represented by an amino acid sequence of SEQ ID NO. 49 or an amino acid sequence obtained by substituting, adding or deleting one or several amino acids in the amino acid sequence; and (27) a polypeptide in which a variable region is represented by an amino acid sequence of SEQ ID NO. 51 or an amino acid sequence obtained by substituting, adding or deleting one or several amino acids in the amino acid sequence.

[4] A pharmaceutical composition, comprising the human antibody κ type light chain complex-containing composition according to any one of [1] to [3] as an active ingredient.

[5] The pharmaceutical composition according to [4], which is an anti-cancer drug.

[6] A method of producing a human antibody κ type light chain complex-containing composition, comprising: an expression process of expressing a human antibody κ type light chain by an intracellular or extracellular expression system using an expression vector including a polynucleotide encoding the human antibody κ type light chain having cysteine residue at the C terminal thereof; and a purification process of purifying the human antibody κ type light chain from the expression product obtained in the expression process, in which, (a) the human antibody κ type light chain is expressed in the presence of one or more kinds of metal ions selected from the group consisting of Group 10 elements, Group 11 elements, and Group 12 elements in the expression process, or (b) the human antibody κ type light chain is purified from a mixture obtained by adding one or more kinds of metal ions selected from the group consisting of Group 10 elements, Group 11 elements, and Group 12 elements to the expression product obtained in the expression process.

[7] The method of producing a human antibody κ type light chain complex-containing composition according to [6], in which, in (b), the human antibody κ type light chain is purified from the mixture after incubating the mixture for 30 minutes to 48 hours.

[8] The method of producing a human antibody κ type light chain complex-containing composition according to [6] or [7], in which the purification process includes: a first purification process of obtaining a crude purified product containing the human antibody κ type light chain from the expression product obtained from the expression process by column chromatography using a column containing a first filler; and a second purification process of obtaining a purified product of the human antibody κ type light chain from the crude purified product obtained from the first purification process by column chromatography using a column containing a second filler, and in which the metal ion is added to the crude purified product before the second purification process after the first purification process.

[9] The method of producing a human antibody κ type light chain complex-containing composition according to [8], in which, before the second purification process, the crude purified product, to which the metal ion has been added, is incubated for 30 minutes to 48 hours.

[10] The method of producing a human antibody κ type light chain complex-containing composition according to [8] or [9], in which the metal ion is added into the expression system in the expression process, and is further added to the crude purified product before the second purification process after the first purification process. [11] A method of producing a human antibody κ type light chain complex-containing composition, in which a human antibody κ type light chain is incubated in a solution containing one or more kinds of metal ions selected from the group consisting of Group 10 elements, Group 11 elements, and Group 12 elements to produce a composition containing a complex in which cysteine residues at C terminals of two human antibody κ type light chains are bound to each other via the metal ion.

Advantageous Effects of Invention

The human antibody κ type light chain complex-containing composition according to the present invention has higher activity than a conventional composition in which a light chain is not bound to metal ions, and can be stably supplied. That is, the human antibody κ type light chain complex-containing composition according to the present invention has high activity and excellent mass-productivity, and is expected to be widely used as clinically applicable pharmaceutical products.

Further, according to the method of producing a human antibody κ type light chain complex-containing composition of the present invention, it is possible to stably produce a human antibody κ type light chain having high activity.

DESCRIPTION OF EMBODIMENTS

Figure 1A:
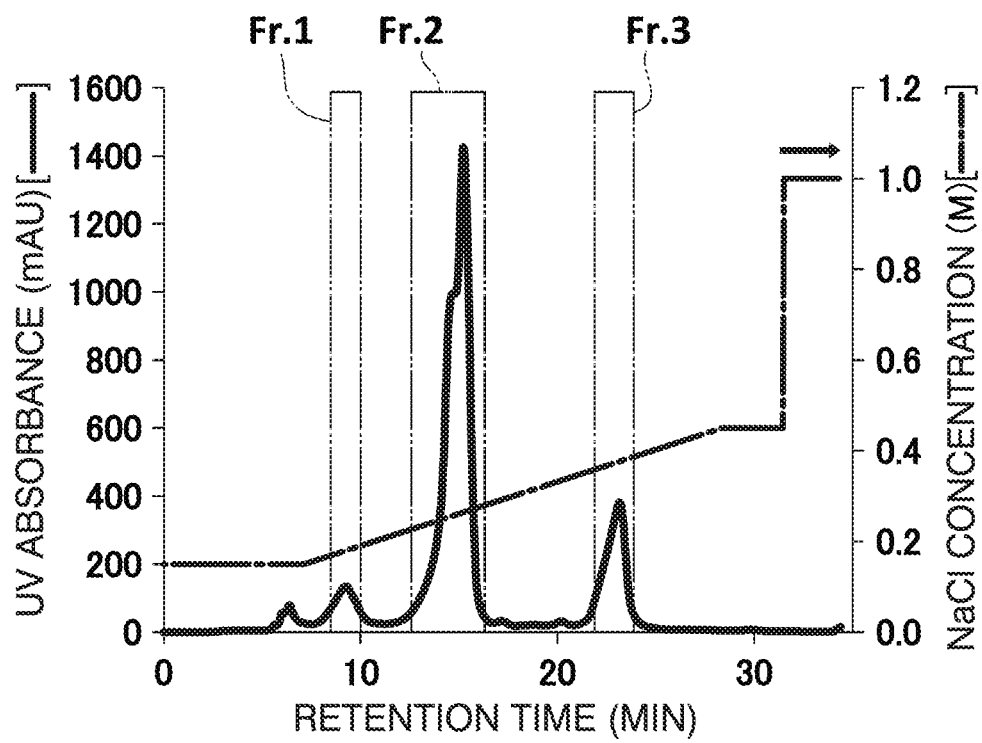
FIG. 1A is a graph showing the results of cation exchange chromatography in the control case (copper ion-free) in Example 1.

In the present invention, the term "human antibody κ type light chain" refers to a κ type light chain of immunoglobulin of human origin. The gene of a κ type antibody light chain is constructed by recombining the genes selected from a Vκ gene cluster, a Jκ gene cluster, and a gene cluster of constant region, existing in a germline gene.

Further, in the present invention, the term "anti-cancer drug" refers to a drug having activity for killing cancer cells or suppressing or inhibiting the proliferation of cancer cells, and the term "cellular cytotoxicity" refers to a property causing death or dysfunction to cells.

It is well known that some amino acids of the amino acid residue constituting a polypeptide can be easily altered without significantly affecting the structure or function of the polypeptide. Further, it is also well known that there exists a mutant that does not significantly change the structure or function of natural protein even when it is artificially altered. Herein, to substitute, add or delete one or more amino acids in a specific amino acid sequence is to mutate them.

The human antibody κ type light chain complex-containing composition according to the present invention (hereinafter, referred to as "a complex-containing composition according to the present invention") is a composition containing a complex in which two human antibody κ type light chains and specific metal ions are bound to each other in a specific amount ratio by the binding of cysteines at the C terminals of the human antibody κ type light chains with the metal ions (by the interaction of cysteines at the C terminals of the human antibody κ type light chains with the metal ions).

<Metal Ion>

In the present invention, the metal ion bound to a human antibody κ type light chain is one kind or more selected from the group consisting of Group 10 elements, Group 11 elements, and Group 12 elements. Only one kind of the metal ions may be bound to the human antibody κ type light chain, and two or more kinds of the metal ions may also be bound to the human antibody κ type light chain. The metal ion is preferably one or more selected from the group consisting of copper ion, nickel ion, zinc ion, gold ion, silver ion, and platinum ion, from the viewpoint of safety to a living body, more preferably one or more selected from the group consisting of copper ion, nickel ion, and zinc ion, from the viewpoint of mass production, and further preferably copper ion from the viewpoint of further increasing the activity of the human antibody κ type light chain to a living body.

<Human Antibody κ Type Light Chain>

The human antibody κ type light chain contained in the complex-containing composition according to the present invention and bound to specific metal ions (hereinafter, referred to as "a human antibody κ type light chain according to the present invention") is not particularly limited as long as it can be bound to the metal ions. However, from the viewpoint of applicability to pharmaceutical use, it is preferable that the human antibody κ type light chain have a catalytic triad residue-like structure. Here, the catalytic triad residue-like structure refers to a structure considered to have catalytic activity, which is formed by, for example, a serine residue, a histidine residue, and an asparagine residue. Examples of the human antibody κ type light chain having the catalytic triad residue-like structure include human antibody κ type light chains having Vκ genes belonging to subgroup II or having at least variable regions thereof, and mutants thereof. Meanwhile, a wild-type human antibody κ type light chain, for example, as disclosed in PTL 2, can be obtained by PCR having a nucleic acid derived from a biological sample (for example, lymphocyte, etc.) collected from a human as a template, and various mutants can be obtained from the obtained wild-type human antibody κ type light chain by gene recombination techniques.

It is particularly preferable that the human antibody κ type light chain according to the present invention have at least any one activity of amidase activity, nucleic acid degradation activity, cytotoxicity against cancer cells, and antiviral activity. The human antibody κ type light chain having these activities is particularly useful as an anti-cancer drug, an antiviral drug, or the like.

A wild-type antibody κ type light chain has cysteine for forming a disulfide bond at the C terminal thereof to form a dimer. In contrast, a mutant-type antibody type light chain, in which the cysteine is substituted with another amino acid (for example, alanine), cannot form a dimer, and exists as a monomer. The human antibody type light chain according to the present invention forms a dimer, and cysteines at C terminals of two human antibody κ type light chains are bound to each other via a metal ion. The human antibody κ type light chain forms a dimer via the metal ion, and thus a complex bound to the metal ion has higher activity than the human antibody κ type light chain before the binding. Further, depending on the kind of human antibody κ type light chains, a dimer has higher activity, such as cytotoxicity, than a monomer. In this regard, the dimer is excellent.

The human antibody κ type light chain according to the present invention is preferably any of the polypeptides of the following (1) to (27): (1) a polypeptide in which a variable region is represented by an amino acid sequence of SEQ ID NO. 1 or an amino acid sequence obtained by substituting, adding or deleting one or several amino acids in the amino acid sequence; (2) a polypeptide in which a variable region is represented by an amino acid sequence of SEQ ID NO. 3 or an amino acid sequence obtained by substituting, adding or deleting one or several amino acids in the amino acid sequence; (3) a polypeptide in which a variable region is represented by an amino acid sequence of SEQ ID NO. 5 or an amino acid sequence obtained by substituting, adding or deleting one or several amino acids in the amino acid sequence; (4) a polypeptide in which a variable region is represented by an amino acid sequence of SEQ ID NO. 7 or an amino acid sequence obtained by substituting, adding or deleting one or several amino acids in the amino acid sequence; (5) a polypeptide in which a variable region is represented by an amino acid sequence of SEQ ID NO. 9 or an amino acid sequence obtained by substituting, adding or deleting one or several amino acids in the amino acid sequence; (6) a polypeptide in which a variable region is represented by an amino acid sequence of SEQ ID NO. 11 or an amino acid sequence obtained by substituting, adding or deleting one or several amino acids in the amino acid sequence; (7) a polypeptide in which a variable region is represented by an amino acid sequence of SEQ ID NO. 13 or an amino acid sequence obtained by substituting, adding or deleting one or several amino acids in the amino acid sequence; (8) a polypeptide in which a variable region is represented by an amino acid sequence of SEQ ID NO. 15 or an amino acid sequence obtained by substituting, adding or deleting one or several amino acids in the amino acid sequence; (9) a polypeptide in which a variable region is represented by an amino acid sequence of SEQ ID NO. 17 or an amino acid sequence obtained by substituting, adding or deleting one or several amino acids in the amino acid sequence; (10) a polypeptide in which a variable region is represented by an amino acid sequence of SEQ ID NO. 19 or an amino acid sequence obtained by substituting, adding or deleting one or several amino acids in the amino acid sequence; (11) a polypeptide in which a variable region is represented by an amino acid sequence of SEQ ID NO. 21 or an amino acid sequence obtained by substituting, adding or deleting one or several amino acids in the amino acid sequence; (12) a polypeptide in which a variable region is represented by an amino acid sequence of SEQ ID NO. 23 or an amino acid sequence obtained by substituting, adding or deleting one or several amino acids in the amino acid sequence; (13) a polypeptide in which a variable region is represented by an amino acid sequence of SEQ ID NO. 25 or an amino acid sequence obtained by substituting, adding or deleting one or several amino acids in the amino acid sequence; (14) a polypeptide in which a variable region is represented by an amino acid sequence of SEQ ID NO. 27 or an amino acid sequence obtained by substituting, adding or deleting one or several amino acids in the amino acid sequence; (15) a polypeptide which is represented by an amino acid sequence in which $219^{th}$ cysteine in an amino acid sequence of SEQ ID NO. 2 is substituted with alanine or by an amino acid sequence obtained by substituting, adding or deleting one or several amino acids in the amino acid sequence; (16) a polypeptide in which a variable region is represented by an amino acid sequence of SEQ ID NO. 29 or an amino acid sequence obtained by substituting, adding or deleting one or several amino acids in the amino acid sequence; (17) a polypeptide in which a variable region is represented by an amino acid sequence of SEQ ID NO. 31 or an amino acid sequence obtained by substituting, adding or deleting one or several amino acids in the amino acid sequence; (18) a polypeptide in which a variable region is represented by an amino acid sequence of SEQ ID NO. 33 or an amino acid sequence obtained by substituting, adding or deleting one or several amino acids in the amino acid sequence; (19) a polypeptide in which a variable region is represented by an amino acid sequence of SEQ ID NO. 35 or an amino acid sequence obtained by substituting, adding or deleting one or several amino acids in the amino acid sequence; (20) a polypeptide in which a variable region is represented by an amino acid sequence of SEQ ID NO. 37 or an amino acid sequence obtained by substituting, adding or deleting one or several amino acids in the amino acid sequence; (21) a polypeptide in which a variable region is represented by an amino acid sequence of SEQ ID NO. 39 or an amino acid sequence obtained by substituting, adding or deleting one or several amino acids in the amino acid sequence; (22) a polypeptide in which a variable region is represented by an amino acid sequence of SEQ ID NO. 41 or an amino acid sequence obtained by substituting, adding or deleting one or several amino acids in the amino acid sequence; (23) a polypeptide in which a variable region is represented by an amino acid sequence of SEQ ID NO. 43 or an amino acid sequence obtained by substituting, adding or deleting one or several amino acids in the amino acid sequence; (24) a polypeptide in which a variable region is represented by an amino acid sequence of SEQ ID NO. 45 or an amino acid sequence obtained by substituting, adding or deleting one or several amino acids in the amino acid sequence; (25) a polypeptide in which a variable region is represented by an amino acid sequence of SEQ ID NO. 47 or an amino acid sequence obtained by substituting, adding or deleting one or several amino acids in the amino acid sequence; (26) a polypeptide in which a variable region is represented by an amino acid sequence of SEQ ID NO. 49 or an amino acid sequence obtained by substituting, adding or deleting one or several amino acids in the amino acid sequence; and (27) a polypeptide in which a variable region is represented by an amino acid sequence of SEQ ID NO. 51 or an amino acid sequence obtained by substituting, adding or deleting one or several amino acids in the amino acid sequence.

The human antibody κ type light chain composed of the polypeptide in which a variable region is represented by amino acid sequence of SEQ ID NO. 1 is referred to as "human antibody κ type light chain (#7)". The human antibody κ type light chain (#7) may be a human antibody κ type light chain in which a known human antibody constant region is added to the above-mentioned variable region. In one embodiment, the full-length amino acid sequence is represented by SEQ ID NO. 2. In the human antibody κ type light chain (#7), CDR 1 is $24^{th}$ to $39^{th}$ in the amino acid sequence of SEQ ID NOs. 1 and 2, CDR 2 is $55^{th}$ to $61^{st}$ in the amino acid sequence of SEQ ID NOs. 1 and 2, and CDR 3 is $94^{th}$ to $102^{nd}$ in the amino acid sequence of SEQ ID NOs. 1 and 2. Further, the cysteine that can form a disulfide bond together with another light chain and can be bound to metal ions is the $219^{th}$ cysteine in the amino acid sequence of SEQ ID NO. 2.

Here, the amino acid sequence of SEQ ID NO. 2 represents the full-length wild-type human antibody κ type light chain in which a variable region is represented by the amino acid sequence of SEQ ID NO. 1. The human antibody κ type light chain composed of the polypeptide represented by amino acid sequence of SEQ ID NO. 2 may also be referred to as "human antibody κ type light chain (#7_wt)".

The human antibody κ type light chain (#7), as shown in the following example, has cytotoxicity against cancer cells, particularly, lung cancer cells, stomach cancer cells, leukemia cells (cancerous T-cells), and pancreatic cancer cells. For this reason, the human antibody κ type light chain (#7) is suitable as an active ingredient of an anti-cancer drug. Since high molecular recognition ability for a target molecule is important for anti-cancer activity of the human antibody κ type light chain (#7), the active center of anti-cancer activity of the human antibody κ type light chain (#7) is located in a variable region, particularly, in a CDR sequence.

Therefore, the human antibody κ type light chain (#7) may be configured such that a region other than the variable region is different from the amino acid sequence of SEQ ID NO. 2. For example, a human antibody κ type light chain composed of a polypeptide represented by an amino acid sequence in which the $1^{st}$ aspartic acid of FR-1 in the amino acid sequence of SEQ ID NO. 2 ($1^{st}$ aspartic acid in the amino acid sequence of SEQ ID NO. 2) is substituted with glutamic acid, or composed of a polypeptide represented by an amino acid sequence in which the $2^{nd}$ valine of FR-1 in the amino acid sequence of SEQ ID NO. 2 ($2^{nd}$ valine in the amino acid sequence of SEQ ID NO. 2) is substituted with isoleucine is also included in the human antibody κ type light chain (#7). Here, the polypeptide may also be referred to as "a human antibody κ type light chain (#7_C219A)".

The human antibody κ type light chain according to the present invention may also be composed of a polypeptide represented by an amino acid sequence in which one or several amino acids of the amino acid sequence of SEQ ID NO. 1 are substituted, added, and deleted, or a polypeptide represented by an amino acid sequence which has 95% or more homology (sequence identity) with the amino acid sequence. The polypeptide may also be referred to as "a mutant of the human antibody κ type light chain (#7)".

The mutant of the human antibody κ type light chain (#7) used as the human antibody kκ type light chain according to the present invention has the same anticancer effect as the human antibody κ type light chain (#7). Accordingly, the mutant of the human antibody κ type light chain (#7) is preferably a mutant in which CDR 1, CDR 2, and CDR 3 are identical to the amino acid sequence of SEQ ID NO. 1 or 2 (i.e., CDR 1, CDR 2, and CDR 3 are conserved), and a region other than CDR regions in the variable region and amino acids other than cysteine at the C terminal thereof are mutated from the human antibody κ type light chain (#7).

Examples of the mutant of the human antibody κ type light chain (#7) include a human antibody κ type light chain (#7 VL) composed of a polypeptide in which a variable region is represented by the amino acid sequence of SEQ ID NO. 3, a human antibody κ type light chain (#7 VL (I)) composed of a polypeptide in which a variable region is represented by the amino acid sequence of SEQ ID NO. 5, a human antibody type light chain (#7 VL (RL)) composed of a polypeptide in which a variable region is represented by the amino acid sequence of SEQ ID NO. 7, and a human antibody κ type light chain (#7 RL I) composed of a polypeptide in which a variable region is represented by the amino acid sequence of SEQ ID NO. 9. In one embodiment, the full-length amino acid sequence of the human antibody κ type light chain (#7 VL) is represented by SEQ ID NO. 4, the full-length amino acid sequence of the human antibody κ type light chain (#7 VL (I)) is represented by SEQ ID NO. 6, the full-length amino acid sequence of the human antibody κ type light chain (#7 VL (RL)) is represented by SEQ ID NO. 8, and the full-length amino acid sequence of the human antibody κ type light chain (#7 RL I) is represented by SEQ ID NO. 10.

The human antibody κ type light chain (#7 VL), human antibody κ type light chain (#7 VL (I)), and human antibody κ type light chain (#7 VL (RL)) have high cytotoxicity against lung cancer cells, ovarian cancer cells, and leukemia cells, and the human antibody κ type light chain (#7 RL I) has high cytotoxicity against lung cancer cells, gastric cancer cells, and pancreatic cancer cells.

The human antibody κ type light chain composed of the polypeptide in which a variable region is represented by amino acid sequence of SEQ ID NO. 11 is referred to as "human antibody κ type light chain (#4)". The human antibody κ type light chain (#4) may be a human antibody κ type light chain in which a known human antibody constant region is added to the above-mentioned variable region. In one embodiment, the full-length amino acid sequence is represented by SEQ ID NO. 12. The amino acid sequence of SEQ ID NO. 12 represents the full length of a wild-type human antibody κ type light chain represented by the amino acid sequence in which a variable region is represented by the amino acid sequence of SEQ ID NO. 11. In the human antibody κ type light chain (#4), CDR 1 is $24^{th}$ to $40^{th}$ in the amino acid sequence of SEQ ID NOs. 11 and 12, CDR 2 is $56^{th}$ to $62^{nd}$ in the amino acid sequence of SEQ ID NOs. 11 and 12, and CDR 3 is $95^{th}$ to $103^{rd}$ in the amino acid sequence of SEQ ID NOs. 11 and 12. Further, the cysteine that can form a sulfide bond together with another light chain and can be bound to metal ion is the $220^{th}$ cysteine in the amino acid sequence of SEQ ID NO. 12.

The human antibody κ type light chain (#4), as shown in the following example, has cytotoxicity against cancer cells, particularly, lung cancer cells, ovarian cancer cells, leukemia cells, and gastric cancer cells. For this reason, the human antibody κ type light chain (#4) is suitable as an active ingredient of an anti-cancer drug. The active center of anti-cancer activity of the human antibody κ type light chain (#4) is located in a variable region, particularly, in a CDR sequence. Further, the binding point to the metal ion is cysteine at the C terminal. Therefore, the human antibody κ type light chain (#4) may be configured such that a region other than the variable region and the cysteine at the C terminal thereof is different from the amino acid sequence of SEQ ID NO. 12.

The human antibody κ type light chain according to the present invention may also be composed of a polypeptide represented by an amino acid sequence in which one or several amino acids of the amino acid sequence of SEQ ID NO. 11 are substituted, added, and deleted, or a polypeptide represented by an amino acid sequence which has 95% or more homology (sequence identity) with the amino acid sequence. The polypeptide may also be referred to as "a mutant of the human antibody κ type light chain (#4)".

The mutant of the human antibody κ type light chain (#4) used as the human antibody κ type light chain according to the present invention has the same anticancer effect as the human antibody κ type light chain (#4). Accordingly, the mutant of the human antibody κ type light chain (#4) is preferably a mutant in which CDR 1, CDR 2, and CDR 3, and cysteine at the C terminal thereof are identical to the amino acid sequence of SEQ ID NO. 11 or 12 (i.e., CDR 1, CDR 2, and CDR 3, and cysteine at the C terminal thereof are conserved), and a region other than CDR regions in the variable region and amino acids other than the $220^{th}$ cysteine at the C terminal thereof are mutated from the human antibody κ type light chain (#4).

The human antibody κ type light chain composed of the polypeptide in which a variable region is represented by amino acid sequence of SEQ ID NO. 13 is referred to as "human antibody κ type light chain (#11)". The human antibody κ type light chain (#11) may be a human antibody κ type light chain in which a known human antibody constant region is added to the above-mentioned variable region. In one embodiment, the full-length amino acid sequence is represented by SEQ ID NO. 14. The amino acid sequence of SEQ ID NO. 14 represents the full length of a wild-type human antibody κ type light chain represented by the amino acid sequence in which a variable region is represented by the amino acid sequence of SEQ ID NO. 13. In the human antibody κ type light chain (#11), CDR 1 is $24^{th}$ to $39^{th}$ in the amino acid sequence of SEQ ID NOs. 13 and 14, CDR 2 is $55^{th}$ to $61^{st}$ in the amino acid sequence of SEQ ID NOs. 13 and 14, and CDR 3 is $94^{th}$ to $102^{nd}$ in the amino acid sequence of SEQ ID NOs. 13 and 14. Further, the cysteine that can form a sulfide bond together with another light chain and can be bound to metal ion is the $219^{th}$ cysteine in the amino acid sequence of SEQ ID NO. 14.

The human antibody κ type light chain (#11), as shown in the following example, has cytotoxicity against cancer cells, particularly, lung cancer cells and ovarian cancer cells. For this reason, the human antibody κ type light chain (#11) is suitable as an active ingredient of an anti-cancer drug. The active center of anti-cancer activity of the human antibody κ type light chain (#11) is located in a variable region, particularly, in a CDR sequence. Further, the binding point to the metal ion is cysteine at the C terminal. Therefore, the human antibody κ type light chain (#11) may be configured such that a region other than the variable region and the cysteine at the C terminal thereof is different from the amino acid sequence of SEQ ID NO. 14.

The human antibody κ type light chain according to the present invention may also be composed of a polypeptide represented by an amino acid sequence in which one or several amino acids of the amino acid sequence of SEQ ID NO. 13 are substituted, added, and deleted, or a polypeptide represented by an amino acid sequence which has 95% or more homology (sequence identity) with the amino acid sequence. The polypeptide may also be referred to as "a mutant of the human antibody κ type light chain (#11)".

The mutant of the human antibody κ type light chain (#11) used as the human antibody κ type light chain according to the present invention has the same anticancer effect as the human antibody κ type light chain (#11). Accordingly, the mutant of the human antibody κ type light chain (#11) is preferably a mutant in which CDR 1, CDR 2, and CDR 3, and cysteine at the C terminal thereof are identical to the amino acid sequence of SEQ ID NO. 13 or 14 (i.e., CDR 1, CDR 2, and CDR 3, and cysteine at the C terminal thereof are conserved), and a region other than CDR regions in the variable region and amino acids other than the $219^{th}$ cysteine at the C terminal thereof are mutated from the human antibody κ type light chain (#11).

The human antibody κ type light chain composed of the polypeptide in which a variable region is represented by amino acid sequence of SEQ ID NO. 15 is referred to as "human antibody κ type light chain (23D4)". The human antibody κ type light chain (23D4) may be a human antibody κ type light chain in which a known human antibody constant region is added to the above-mentioned variable region. In one embodiment, the full-length amino acid sequence is represented by SEQ ID NO. 16. The amino acid sequence of SEQ ID NO. 16 represents the full length of a wild-type human antibody κ type light chain represented by the amino acid sequence in which a variable region is represented by the amino acid sequence of SEQ ID NO. 15. In the human antibody κ type light chain (23D4), CDR 1 is $24^{th}$ to $39^{th}$ in the amino acid sequence of SEQ ID NOs. 15 and 16, CDR 2 is $55^{th}$ to $61^{st}$ in the amino acid sequence of SEQ ID NOs. 15 and 16, and CDR 3 is $94^{th}$ to $102^{nd}$ in the amino acid sequence of SEQ ID NOs. 15 and 16. Further, the cysteine that can form a sulfide bond together with another light chain and can be bound to metal ion is the $219^{th}$ cysteine in the amino acid sequence of SEQ ID NO. 16.

The human antibody κ type light chain (23D4), as shown in the following example, has cytotoxicity against cancer cells, particularly, lung cancer cells, ovarian cancer cells, and leukemia cells. For this reason, the human antibody κ type light chain (23D4) is suitable as an active ingredient of an anti-cancer drug. The active center of anti-cancer activity of the human antibody κ type light chain (23D4) is located in a variable region, particularly, in a CDR sequence. Further, the binding point to the metal ion is cysteine at the C terminal. Therefore, the human antibody κ type light chain (23D4) may be configured such that a region other than the variable region and the cysteine at the C terminal thereof is different from the amino acid sequence of SEQ ID NO. 16.

The human antibody κ type light chain according to the present invention may also be composed of a polypeptide represented by an amino acid sequence in which one or several amino acids of the amino acid sequence of SEQ ID NO. 15 are substituted, added, and deleted, or a polypeptide represented by an amino acid sequence which has 95% or more homology (sequence identity) with the amino acid sequence. The polypeptide may also be referred to as "a mutant of the human antibody κ type light chain (23D4)".

The mutant of the human antibody κ type light chain (23D4) used as the human antibody κ type light chain according to the present invention has the same anticancer effect as the human antibody κ type light chain (23D4). Accordingly, the mutant of the human antibody κ type light chain (23D4) is preferably a mutant in which CDR 1, CDR 2, and CDR 3, and cysteine at the C terminal thereof are identical to the amino acid sequence of SEQ ID NO. 15 or 16 (i.e., CDR 1, CDR 2, and CDR 3, and cysteine at the C terminal thereof are conserved), and a region other than CDR regions in the variable region and amino acids other than the $219^{th}$ cysteine at the C terminal thereof are mutated from the human antibody κ type light chain (23D4).

The human antibody κ type light chain composed of the polypeptide in which a variable region is represented by amino acid sequence of SEQ ID NO. 17 is referred to as "human antibody κ type light chain (W3)". The human antibody κ type light chain (W3) may be a human antibody κ type light chain in which a known human antibody constant region is added to the above-mentioned variable region. In one embodiment, the full-length amino acid sequence is represented by SEQ ID NO. 18. The amino acid sequence of SEQ ID NO. 18 represents the full length of a wild-type human antibody type light chain represented by the amino acid sequence in which a variable region is represented by the amino acid sequence of SEQ ID NO. 17. In the human antibody type light chain (W3), CDR 1 is $24^{th}$ to $39^{th}$ in the amino acid sequence of SEQ ID NOs. 17 and 18, CDR 2 is $55^{th}$ to $61^{st}$ in the amino acid sequence of SEQ ID NOs. 17 and 18, and CDR 3 is $94^{th}$ to $102^{nd}$ in the amino acid sequence of SEQ ID NOs. 17 and 18. Further, the cysteine that can form a sulfide bond together with another light chain and can be bound to metal ion is the $219^{th}$ cysteine in the amino acid sequence of SEQ ID NO. 18.

The human antibody κ type light chain (W3), as shown in the following example, has cytotoxicity against cancer cells, particularly, lung cancer cells, gastric cancer cells, pancreatic cancer cells, ovarian cancer cells, and leukemia cells. For this reason, the human antibody κ type light chain (W3) is suitable as an active ingredient of an anti-cancer drug. The active center of anti-cancer activity of the human antibody κ type light chain (W3) is located in a variable region, particularly, in a CDR sequence. Further, the binding point to the metal ion is cysteine at the C terminal. Therefore, the human antibody κ type light chain (W3) may be configured such that a region other than the variable region and the cysteine at the C terminal thereof is different from the amino acid sequence of SEQ ID NO. 18.

The human antibody κ type light chain according to the present invention may also be composed of a polypeptide represented by an amino acid sequence in which one or several amino acids of the amino acid sequence of SEQ ID NO. 17 are substituted, added, and deleted, or a polypeptide represented by an amino acid sequence which has 95% or more homology (sequence identity) with the amino acid sequence. The polypeptide may also be referred to as "a mutant of the human antibody κ type light chain (W3)".

The mutant of the human antibody κ type light chain (W3) used as the human antibody κ type light chain according to the present invention has the same anticancer effect as the human antibody κ type light chain (W3). Accordingly, the mutant of the human antibody κ type light chain (W3) is preferably a mutant in which CDR 1, CDR 2, and CDR 3, and cysteine at the C terminal thereof are identical to the amino acid sequence of SEQ ID NO. 17 or 18 (i.e., CDR 1, CDR 2, and CDR 3, and cysteine at the C terminal thereof are conserved), and a region other than CDR regions in the variable region and amino acids other than the $219^{th}$ cysteine at the C terminal thereof are mutated from the human antibody κ type light chain (W3).

The human antibody κ type light chain composed of the polypeptide in which a variable region is represented by amino acid sequence of SEQ ID NO. 19 is referred to as "human antibody κ type light chain (W10)". The human antibody κ type light chain (W10) may be a human antibody κ type light chain in which a known human antibody constant region is added to the above-mentioned variable region. In one embodiment, the full-length amino acid sequence is represented by SEQ ID NO. 20. The amino acid sequence of SEQ ID NO. 20 represents the full length of a wild-type human antibody type light chain represented by the amino acid sequence in which a variable region is represented by the amino acid sequence of SEQ ID NO. 19. In the human antibody type light chain (W10), CDR 1 is $24^{th}$ to $39^{th}$ in the amino acid sequence of SEQ ID NOs. 19 and 20, CDR 2 is $55^{th}$ to $61^{st}$ in the amino acid sequence of SEQ ID NOs. 19 and 20, and CDR 3 is $94^{th}$ to $102^{nd}$ in the amino acid sequence of SEQ ID NOs. 19 and 20. Further, the cysteine that can form a sulfide bond together with another light chain and can be bound to metal ion is the $219^{th}$ cysteine in the amino acid sequence of SEQ ID NO. 20.

The human antibody κ type light chain (W10), as shown in the following example, has cytotoxicity against cancer cells, particularly, lung cancer cells, pancreatic cancer cells, ovarian cancer cells, and leukemia cells. For this reason, the human antibody κ type light chain (W10) is suitable as an active ingredient of an anti-cancer drug. The active center of anti-cancer activity of the human antibody κ type light chain (W10) is located in a variable region, particularly, in a CDR sequence. Further, the binding point to the metal ion is cysteine at the C terminal. Therefore, the human antibody κ type light chain (W10) may be configured such that a region other than the variable region and the cysteine at the C terminal thereof is different from the amino acid sequence of SEQ ID NO. 20.

The human antibody κ type light chain according to the present invention may also be composed of a polypeptide represented by an amino acid sequence in which one or several amino acids of the amino acid sequence of SEQ ID NO. 19 are substituted, added, and deleted, or a polypeptide represented by an amino acid sequence which has 95% or more homology (sequence identity) with the amino acid sequence. The polypeptide may also be referred to as "a mutant of the human antibody κ type light chain (W10)".

The mutant of the human antibody κ type light chain (W10) used as the human antibody κ type light chain according to the present invention has the same anticancer effect as the human antibody κ type light chain (W10). Accordingly, the mutant of the human antibody κ type light chain (W10) is preferably a mutant in which CDR 1, CDR 2, and CDR 3, and cysteine at the C terminal thereof are identical to the amino acid sequence of SEQ ID NO. 19 or 20 (i.e., CDR 1, CDR 2, and CDR 3, and cysteine at the C terminal thereof are conserved), and a region other than CDR regions in the variable region and amino acids other than the $219^{th}$ cysteine at the C terminal thereof are mutated from the human antibody κ type light chain (W10).

The human antibody κ type light chain composed of the polypeptide in which a variable region is represented by amino acid sequence of SEQ ID NO. 21 is referred to as "human antibody κ type light chain (C51)". The human antibody κ type light chain (C51) may be a human antibody κ type light chain in which a known human antibody constant region is added to the above-mentioned variable region. In one embodiment, the full-length amino acid sequence is represented by SEQ ID NO. 22. The amino acid sequence of SEQ ID NO. 22 represents the full length of a wild-type human antibody κ type light chain represented by the amino acid sequence in which a variable region is represented by the amino acid sequence of SEQ ID NO. 21. In the human antibody κ type light chain (C51), CDR 1 is $24^{th}$ to $34^{th}$ in the amino acid sequence of SEQ ID NOs. 21 and 22, CDR 2 is $50^{th}$ to $56^{th}$ in the amino acid sequence of SEQ ID NOs. 21 and 22, and CDR 3 is $89^{th}$ to $97^{th}$ in the amino acid sequence of SEQ ID NOs. 21 and 22. Further, the cysteine that can form a sulfide bond together with another light chain and can be bound to metal ion is the $214^{th}$ cysteine in the amino acid sequence of SEQ ID NO. 22.

The human antibody κ type light chain (C51), as shown in the following example, has cytotoxicity against cancer cells, particularly, lung cancer cells, ovarian cancer cells, and leukemia cells. For this reason, the human antibody κ type light chain (C51) is suitable as an active ingredient of an anti-cancer drug. The active center of anti-cancer activity of the human antibody κ type light chain (C51) is located in a variable region, particularly, in a CDR sequence. Further, the binding point to the metal ion is cysteine at the C terminal. Therefore, the human antibody κ type light chain (C51) may be configured such that a region other than the variable region and the cysteine at the C terminal thereof is different from the amino acid sequence of SEQ ID NO. 22.

The human antibody κ type light chain according to the present invention may also be composed of a polypeptide represented by an amino acid sequence in which one or several amino acids of the amino acid sequence of SEQ ID NO. 21 are substituted, added, and deleted, or a polypeptide represented by an amino acid sequence which has 95% or more homology (sequence identity) with the amino acid sequence. The polypeptide may also be referred to as "a mutant of the human antibody κ type light chain (C51)".

The mutant of the human antibody κ type light chain (C51) used as the human antibody κ type light chain according to the present invention has the same anticancer effect as the human antibody κ type light chain (C51). Accordingly, the mutant of the human antibody κ type light chain (C51) is preferably a mutant in which CDR 1, CDR 2, and CDR 3, and cysteine at the C terminal thereof are identical to the amino acid sequence of SEQ ID NO. 21 or 22 (i.e., CDR 1, CDR 2, and CDR 3, and cysteine at the C terminal thereof are conserved), and a region other than CDR regions in the variable region and amino acids other than the $214^{th}$ cysteine at the C terminal thereof are mutated from the human antibody κ type light chain (C51).

The human antibody κ type light chain composed of the polypeptide in which a variable region is represented by amino acid sequence of SEQ ID NO. 23 is referred to as "human antibody κ type light chain (C82)". The human antibody κ type light chain (C82) may be a human antibody κ type light chain in which a known human antibody constant region is added to the above-mentioned variable region. In one embodiment, the full-length amino acid sequence is represented by SEQ ID NO. 24. The amino acid sequence of SEQ ID NO. 24 represents the full length of a wild-type human antibody type light chain represented by the amino acid sequence in which a variable region is represented by the amino acid sequence of SEQ ID NO. 23. In the human antibody type light chain (C82), CDR 1 is $24^{th}$ to $34^{th}$ in the amino acid sequence of SEQ ID NOs. 23 and 24, CDR 2 is $50^{th}$ to $56^{th}$ in the amino acid sequence of SEQ ID NOs. 23 and 24, and CDR 3 is $89^{th}$ to $98^{th}$ in the amino acid sequence of SEQ ID NOs. 23 and 24. Further, the cysteine that can form a sulfide bond together with another light chain and can be bound to metal ion is the $215^{th}$ cysteine in the amino acid sequence of SEQ ID NO. 24.

The human antibody κ type light chain (C82), as shown in the following example, has cytotoxicity against cancer cells, particularly, ovarian cancer cells. For this reason, the human antibody κ type light chain (C82) is suitable as an active ingredient of an anti-cancer drug. The active center of anti-cancer activity of the human antibody κ type light chain (C82) is located in a variable region, particularly, in a CDR sequence. Further, the binding point to the metal ion is cysteine at the C terminal. Therefore, the human antibody κ type light chain (C82) may be configured such that a region other than the variable region and the cysteine at the C terminal thereof is different from the amino acid sequence of SEQ ID NO. 24.

The human antibody κ type light chain according to the present invention may also be composed of a polypeptide represented by an amino acid sequence in which one or several amino acids of the amino acid sequence of SEQ ID NO. 23 are substituted, added, and deleted, or a polypeptide represented by an amino acid sequence which has 95% or more homology (sequence identity) with the amino acid sequence. The polypeptide may also be referred to as "a mutant of the human antibody κ type light chain (C82)".

The mutant of the human antibody κ type light chain (C82) used as the human antibody κ type light chain according to the present invention has the same anticancer effect as the human antibody κ type light chain (C82).

Accordingly, the mutant of the human antibody κ type light chain (C82) is preferably a mutant in which CDR 1, CDR 2, and CDR 3, and cysteine at the C terminal thereof are identical to the amino acid sequence of SEQ ID NO. 23 or 24 (i.e., CDR 1, CDR 2, and CDR 3, and cysteine at the C terminal thereof are conserved), and a region other than CDR regions in the variable region and amino acids other than the 215$^{th}$ cysteine at the C terminal thereof are mutated from the human antibody κ type light chain (C82).

The human antibody κ type light chain composed of the polypeptide in which a variable region is represented by amino acid sequence of SEQ ID NO. 25 is referred to as "human antibody κ type light chain (C89)". The human antibody κ type light chain (C89) may be a human antibody κ type light chain in which a known human antibody constant region is added to the above-mentioned variable region. In one embodiment, the full-length amino acid sequence is represented by SEQ ID NO. 26. The amino acid sequence of SEQ ID NO. 26 represents the full length of a wild-type human antibody type light chain represented by the amino acid sequence in which a variable region is represented by the amino acid sequence of SEQ ID NO. 25. In the human antibody type light chain (C89), CDR 1 is 24$^{th}$ to 35$^{th}$ in the amino acid sequence of SEQ ID NOs. 25 and 26, CDR 2 is 51$^{St}$ to 57$^{th}$ in the amino acid sequence of SEQ ID NOs. 25 and 26, and CDR 3 is 90$^{th}$ to 98$^{th}$ in the amino acid sequence of SEQ ID NOs. 25 and 26. Further, the cysteine that can form a sulfide bond together with another light chain and can be bound to metal ion is the 215$^{th}$ cysteine in the amino acid sequence of SEQ ID NO. 26.

The human antibody κ type light chain (C89), as shown in the following example, has cytotoxicity against cancer cells, particularly, ovarian cancer cells. For this reason, the human antibody κ type light chain (C89) is suitable as an active ingredient of an anti-cancer drug. The active center of anti-cancer activity of the human antibody κ type light chain (C89) is located in a variable region, particularly, in a CDR sequence. Further, the binding point to the metal ion is cysteine at the C terminal. Therefore, the human antibody κ type light chain (C89) may be configured such that a region other than the variable region and the cysteine at the C terminal thereof is different from the amino acid sequence of SEQ ID NO. 26.

The human antibody κ type light chain according to the present invention may also be composed of a polypeptide represented by an amino acid sequence in which one or several amino acids of the amino acid sequence of SEQ ID NO. 25 are substituted, added, and deleted, or a polypeptide represented by an amino acid sequence which has 95% or more homology (sequence identity) with the amino acid sequence. The polypeptide may also be referred to as "a mutant of the human antibody κ type light chain (C89)".

The mutant of the human antibody κ type light chain (C89) used as the human antibody κ type light chain according to the present invention has the same anticancer effect as the human antibody κ type light chain (C89). Accordingly, the mutant of the human antibody κ type light chain (C89) is preferably a mutant in which CDR 1, CDR 2, and CDR 3, and cysteine at the C terminal thereof are identical to the amino acid sequence of SEQ ID NO. 25 or 26 (i.e., CDR 1, CDR 2, and CDR 3, and cysteine at the C terminal thereof are conserved), and a region other than CDR regions in the variable region and amino acids other than the 215$^{th}$ cysteine at the C terminal thereof are mutated from the human antibody κ type light chain (C89).

The human antibody κ type light chain composed of the polypeptide in which a variable region is represented by amino acid sequence of SEQ ID NO. 27 is referred to as "human antibody κ type light chain (W2)". The human antibody κ type light chain (W2) may be a human antibody κ type light chain in which a known human antibody constant region is added to the above-mentioned variable region. In one embodiment, the full-length amino acid sequence is represented by SEQ ID NO. 28. The amino acid sequence of SEQ ID NO. 28 represents the full length of a wild-type human antibody κ type light chain represented by the amino acid sequence in which a variable region is represented by the amino acid sequence of SEQ ID NO. 27. In the human antibody κ type light chain (W2), CDR 1 is 24$^{th}$ to 39$^{th}$ in the amino acid sequence of SEQ ID NOs. 27 and 28, CDR 2 is 55$^{th}$ to 61$^{st}$ in the amino acid sequence of SEQ ID NOs. 27 and 28, and CDR 3 is 94$^{th}$ to 102$^{nd}$ in the amino acid sequence of SEQ ID NOs. 27 and 28. Further, the cysteine that can form a sulfide bond together with another light chain and can be bound to metal ion is the 219$^{th}$ cysteine in the amino acid sequence of SEQ ID NO. 28.

The human antibody κ type light chain (W2), as shown in the following example, has cytotoxicity against cancer cells, particularly, ovarian cancer cells and leukemia cells. For this reason, the human antibody κ type light chain (W2) is suitable as an active ingredient of an anti-cancer drug. The active center of anti-cancer activity of the human antibody κ type light chain (W2) is located in a variable region, particularly, in a CDR sequence. Further, the binding point to the metal ion is cysteine at the C terminal. Therefore, the human antibody κ type light chain (W2) may be configured such that a region other than the variable region and the cysteine at the C terminal thereof is different from the amino acid sequence of SEQ ID NO. 28.

The human antibody κ type light chain according to the present invention may also be composed of a polypeptide represented by an amino acid sequence in which one or several amino acids of the amino acid sequence of SEQ ID NO. 27 are substituted, added, and deleted, or a polypeptide represented by an amino acid sequence which has 95% or more homology (sequence identity) with the amino acid sequence. The polypeptide may also be referred to as "a mutant of the human antibody κ type light chain (W2)".

The mutant of the human antibody κ type light chain (W2) used as the human antibody κ type light chain according to the present invention has the same anticancer effect as the human antibody κ type light chain (W2). Accordingly, the mutant of the human antibody κ type light chain (W2) is preferably a mutant in which CDR 1, CDR 2, and CDR 3, and cysteine at the C terminal thereof are identical to the amino acid sequence of SEQ ID NO. 27 or 28 (i.e., CDR 1, CDR 2, and CDR 3, and cysteine at the C terminal thereof are conserved), and a region other than CDR regions in the variable region and amino acids other than the 219$^{th}$ cysteine at the C terminal thereof are mutated from the human antibody κ type light chain (W2).

The human antibody κ type light chain composed of the polypeptide in which a variable region is represented by amino acid sequence of SEQ ID NO. 29 is referred to as "human antibody κ type light chain (W4)". The human antibody κ type light chain (W4) may be a human antibody κ type light chain in which a known human antibody constant region is added to the above-mentioned variable region. In one embodiment, the full-length amino acid sequence is represented by SEQ ID NO. 30. The amino acid sequence of SEQ ID NO. 30 represents the full length of a wild-type human antibody type light chain represented by the amino acid sequence in which a variable region is represented by the amino acid sequence of SEQ ID NO. 29.

In the human antibody type light chain (W4), CDR 1 is 24$^{th}$ to 39$^{th}$ in the amino acid sequence of SEQ ID NOs. 29 and 30, CDR 2 is 55$^{th}$ to 61$^{st}$ in the amino acid sequence of SEQ ID NOs. 29 and 30, and CDR 3 is 94$^{th}$ to 102$^{nd}$ in the amino acid sequence of SEQ ID NOs. 29 and 30. Further, the cysteine that can form a sulfide bond together with another light chain and can be bound to metal ion is the 219$^{th}$ cysteine in the amino acid sequence of SEQ ID NO. 30.

The human antibody κ type light chain (W4), as shown in the following example, has cytotoxicity against cancer cells, particularly, ovarian cancer cells and leukemia cells. For this reason, the human antibody κ type light chain (W4) is suitable as an active ingredient of an anti-cancer drug. The active center of anti-cancer activity of the human antibody κ type light chain (W4) is located in a variable region, particularly, in a CDR sequence. Further, the binding point to the metal ion is cysteine at the C terminal. Therefore, the human antibody κ type light chain (W4) may be configured such that a region other than the variable region and the cysteine at the C terminal thereof is different from the amino acid sequence of SEQ ID NO. 30.

The human antibody κ type light chain according to the present invention may also be composed of a polypeptide represented by an amino acid sequence in which one or several amino acids of the amino acid sequence of SEQ ID NO. 29 are substituted, added, and deleted, or a polypeptide represented by an amino acid sequence which has 95% or more homology (sequence identity) with the amino acid sequence. The polypeptide may also be referred to as "a mutant of the human antibody κ type light chain (W4)".

The mutant of the human antibody κ type light chain (W4) used as the human antibody κ type light chain according to the present invention has the same anticancer effect as the human antibody κ type light chain (W4). Accordingly, the mutant of the human antibody κ type light chain (W4) is preferably a mutant in which CDR 1, CDR 2, and CDR 3, and cysteine at the C terminal thereof are identical to the amino acid sequence of SEQ ID NO. 29 or 30 (i.e., CDR 1, CDR 2, and CDR 3, and cysteine at the C terminal thereof are conserved), and a region other than CDR regions in the variable region and amino acids other than the 219$^{th}$ cysteine at the C terminal thereof are mutated from the human antibody κ type light chain (W4).

The human antibody κ type light chain composed of the polypeptide in which a variable region is represented by amino acid sequence of SEQ ID NO. 31 is referred to as "human antibody κ type light chain (W7)". The human antibody κ type light chain (W7) may be a human antibody κ type light chain in which a known human antibody constant region is added to the above-mentioned variable region. In one embodiment, the full-length amino acid sequence is represented by SEQ ID NO. 32. The amino acid sequence of SEQ ID NO. 32 represents the full length of a wild-type human antibody type light chain represented by the amino acid sequence in which a variable region is represented by the amino acid sequence of SEQ ID NO. 31. In the human antibody type light chain (W7), CDR 1 is 24$^{th}$ to 39$^{th}$ in the amino acid sequence of SEQ ID NOs. 31 and 32, CDR 2 is 55$^{th}$ to 61$^{st}$ in the amino acid sequence of SEQ ID NOs. 31 and 32, and CDR 3 is 94$^{th}$ to 102$^{nd}$ in the amino acid sequence of SEQ ID NOs. 31 and 32. Further, the cysteine that can form a sulfide bond together with another light chain and can be bound to metal ion is the 219$^{th}$ cysteine in the amino acid sequence of SEQ ID NO. 32.

The human antibody κ type light chain (W7), as shown in the following example, has cytotoxicity against cancer cells, particularly, ovarian cancer cells and leukemia cells. For this reason, the human antibody κ type light chain (W7) is suitable as an active ingredient of an anti-cancer drug. The active center of anti-cancer activity of the human antibody κ type light chain (W7) is located in a variable region, particularly, in a CDR sequence. Further, the binding point to the metal ion is cysteine at the C terminal. Therefore, the human antibody κ type light chain (W7) may be configured such that a region other than the variable region and the cysteine at the C terminal thereof is different from the amino acid sequence of SEQ ID NO. 32.

The human antibody κ type light chain according to the present invention may also be composed of a polypeptide represented by an amino acid sequence in which one or several amino acids of the amino acid sequence of SEQ ID NO. 31 are substituted, added, and deleted, or a polypeptide represented by an amino acid sequence which has 95% or more homology (sequence identity) with the amino acid sequence. The polypeptide may also be referred to as "a mutant of the human antibody κ type light chain (W7)".

The mutant of the human antibody κ type light chain (W7) used as the human antibody κ type light chain according to the present invention has the same anticancer effect as the human antibody κ type light chain (W7). Accordingly, the mutant of the human antibody κ type light chain (W7) is preferably a mutant in which CDR 1, CDR 2, and CDR 3, and cysteine at the C terminal thereof are identical to the amino acid sequence of SEQ ID NO. 31 or 32 (i.e., CDR 1, CDR 2, and CDR 3, and cysteine at the C terminal thereof are conserved), and a region other than CDR regions in the variable region and amino acids other than the 219$^{th}$ cysteine at the C terminal thereof are mutated from the human antibody κ type light chain (W7).

The human antibody κ type light chain composed of the polypeptide in which a variable region is represented by amino acid sequence of SEQ ID NO. 33 is referred to as "human antibody κ type light chain (W8)". The human antibody κ type light chain (W8) may be a human antibody κ type light chain in which a known human antibody constant region is added to the above-mentioned variable region. In one embodiment, the full-length amino acid sequence is represented by SEQ ID NO. 34. The amino acid sequence of SEQ ID NO. 34 represents the full length of a wild-type human antibody type light chain represented by the amino acid sequence in which a variable region is represented by the amino acid sequence of SEQ ID NO. 33. In the human antibody type light chain (W8), CDR 1 is 24$^{th}$ to 39$^{th}$ in the amino acid sequence of SEQ ID NOs. 33 and 34, CDR 2 is 55$^{th}$ to 61$^{st}$ in the amino acid sequence of SEQ ID NOs. 33 and 34, and CDR 3 is 94$^{th}$ to 102$^{nd}$ in the amino acid sequence of SEQ ID NOs. 33 and 34. Further, the cysteine that can form a sulfide bond together with another light chain and can be bound to metal ion is the 219$^{th}$ cysteine in the amino acid sequence of SEQ ID NO. 34.

The human antibody κ type light chain (W8), as shown in the following example, has cytotoxicity against cancer cells, particularly, lung cancer cells, ovarian cancer cells, and leukemia cells. For this reason, the human antibody κ type light chain (W8) is suitable as an active ingredient of an anti-cancer drug. The active center of anti-cancer activity of the human antibody κ type light chain (W8) is located in a variable region, particularly, in a CDR sequence. Further, the binding point to the metal ion is cysteine at the C terminal. Therefore, the human antibody κ type light chain (W8) may be configured such that a region other than the variable region and the cysteine at the C terminal thereof is different from the amino acid sequence of SEQ ID NO. 34.

The human antibody κ type light chain according to the present invention may also be composed of a polypeptide represented by an amino acid sequence in which one or several amino acids of the amino acid sequence of SEQ ID NO. 33 are substituted, added, and deleted, or a polypeptide represented by an amino acid sequence which has 95% or more homology (sequence identity) with the amino acid sequence. The polypeptide may also be referred to as "a mutant of the human antibody κ type light chain (W8)".

The mutant of the human antibody κ type light chain (W8) used as the human antibody κ type light chain according to the present invention has the same anticancer effect as the human antibody κ type light chain (W8). Accordingly, the mutant of the human antibody κ type light chain (W8) is preferably a mutant in which CDR 1, CDR 2, and CDR 3, and cysteine at the C terminal thereof are identical to the amino acid sequence of SEQ ID NO. 33 or 34 (i.e., CDR 1, CDR 2, and CDR 3, and cysteine at the C terminal thereof are conserved), and a region other than CDR regions in the variable region and amino acids other than the $219^{th}$ cysteine at the C terminal thereof are mutated from the human antibody κ type light chain (W8).

The human antibody κ type light chain composed of the polypeptide in which a variable region is represented by amino acid sequence of SEQ ID NO. 35 is referred to as "human antibody κ type light chain (W11)". The human antibody κ type light chain (W11) may be a human antibody κ type light chain in which a known human antibody constant region is added to the above-mentioned variable region. In one embodiment, the full-length amino acid sequence is represented by SEQ ID NO. 36. The amino acid sequence of SEQ ID NO. 36 represents the full length of a wild-type human antibody type light chain represented by the amino acid sequence in which a variable region is represented by the amino acid sequence of SEQ ID NO. 35. In the human antibody κ type light chain (W11), CDR 1 is $24^{th}$ to $39^{th}$ in the amino acid sequence of SEQ ID NOs. 35 and 36, CDR 2 is $55^{th}$ to $61^{st}$ in the amino acid sequence of SEQ ID NOs. 35 and 36, and CDR 3 is $94^{th}$ to $102^{nd}$ in the amino acid sequence of SEQ ID NOs. 35 and 36. Further, the cysteine that can form a sulfide bond together with another light chain and can be bound to metal ion is the $219^{th}$ cysteine in the amino acid sequence of SEQ ID NO. 36.

The human antibody κ type light chain (W11), as shown in the following example, has cytotoxicity against cancer cells, particularly, ovarian cancer cells and leukemia cells. For this reason, the human antibody κ type light chain (W11) is suitable as an active ingredient of an anti-cancer drug. The active center of anti-cancer activity of the human antibody κ type light chain (W11) is located in a variable region, particularly, in a CDR sequence. Further, the binding point to the metal ion is cysteine at the C terminal. Therefore, the human antibody κ type light chain (W11) may be configured such that a region other than the variable region and the cysteine at the C terminal thereof is different from the amino acid sequence of SEQ ID NO. 36.

The human antibody κ type light chain according to the present invention may also be composed of a polypeptide represented by an amino acid sequence in which one or several amino acids of the amino acid sequence of SEQ ID NO. 35 are substituted, added, and deleted, or a polypeptide represented by an amino acid sequence which has 95% or more homology (sequence identity) with the amino acid sequence. The polypeptide may also be referred to as "a mutant of the human antibody κ type light chain (W11)".

The mutant of the human antibody κ type light chain (W11) used as the human antibody κ type light chain according to the present invention has the same anticancer effect as the human antibody κ type light chain (W11). Accordingly, the mutant of the human antibody κ type light chain (W11) is preferably a mutant in which CDR 1, CDR 2, and CDR 3, and cysteine at the C terminal thereof are identical to the amino acid sequence of SEQ ID NO. 35 or 36 (i.e., CDR 1, CDR 2, and CDR 3, and cysteine at the C terminal thereof are conserved), and a region other than CDR regions in the variable region and amino acids other than the $219^{th}$ cysteine at the C terminal thereof are mutated from the human antibody κ type light chain (W11).

The human antibody κ type light chain composed of the polypeptide in which a variable region is represented by amino acid sequence of SEQ ID NO. 37 is referred to as "human antibody κ type light chain (W14)". The human antibody κ type light chain (W14) may be a human antibody κ type light chain in which a known human antibody constant region is added to the above-mentioned variable region. In one embodiment, the full-length amino acid sequence is represented by SEQ ID NO. 38. The amino acid sequence of SEQ ID NO. 38 represents the full length of a wild-type human antibody κ type light chain represented by the amino acid sequence in which a variable region is represented by the amino acid sequence of SEQ ID NO. 37. In the human antibody κ type light chain (W14), CDR 1 is $24^{th}$ to $39^{th}$ in the amino acid sequence of SEQ ID NOs. 37 and 38, CDR 2 is $55^{th}$ to $61^{st}$ in the amino acid sequence of SEQ ID NOs. 37 and 38, and CDR 3 is $94^{th}$ to $103^{rd}$ in the amino acid sequence of SEQ ID NOs. 37 and 38. Further, the cysteine that can form a sulfide bond together with another light chain and can be bound to metal ion is the $220^{th}$ cysteine in the amino acid sequence of SEQ ID NO. 38.

The human antibody κ type light chain (W14), as shown in the following example, has cytotoxicity against cancer cells, particularly, ovarian cancer cells and leukemia cells. For this reason, the human antibody κ type light chain (W14) is suitable as an active ingredient of an anti-cancer drug. The active center of anti-cancer activity of the human antibody κ type light chain (W14) is located in a variable region, particularly, in a CDR sequence. Further, the binding point to the metal ion is cysteine at the C terminal. Therefore, the human antibody κ type light chain (W14) may be configured such that a region other than the variable region and the cysteine at the C terminal thereof is different from the amino acid sequence of SEQ ID NO. 38.

The human antibody κ type light chain according to the present invention may also be composed of a polypeptide represented by an amino acid sequence in which one or several amino acids of the amino acid sequence of SEQ ID NO. 37 are substituted, added, and deleted, or a polypeptide represented by an amino acid sequence which has 95% or more homology (sequence identity) with the amino acid sequence. The polypeptide may also be referred to as "a mutant of the human antibody κ type light chain (W14)".

The mutant of the human antibody κ type light chain (W14) used as the human antibody κ type light chain according to the present invention has the same anticancer effect as the human antibody κ type light chain (W14). Accordingly, the mutant of the human antibody κ type light chain (W14) is preferably a mutant in which CDR 1, CDR 2, and CDR 3, and cysteine at the C terminal thereof are identical to the amino acid sequence of SEQ ID NO. 37 or 38 (i.e., CDR 1, CDR 2, and CDR 3, and cysteine at the C terminal thereof are conserved), and a region other than CDR regions in the variable region and amino acids other than the $220^{th}$ cysteine at the C terminal thereof are mutated from the human antibody κ type light chain (W14).

The human antibody κ type light chain composed of the polypeptide in which a variable region is represented by amino acid sequence of SEQ ID NO. 39 is referred to as "human antibody κ type light chain (W15)". The human antibody κ type light chain (W15) may be a human antibody κ type light chain in which a known human antibody constant region is added to the above-mentioned variable region. In one embodiment, the full-length amino acid sequence is represented by SEQ ID NO. 40. The amino acid sequence of SEQ ID NO. 40 represents the full length of a wild-type human antibody κ type light chain represented by the amino acid sequence in which a variable region is represented by the amino acid sequence of SEQ ID NO. 39. In the human antibody κ type light chain (W15), CDR 1 is $24^{th}$ to $39^{th}$ in the amino acid sequence of SEQ ID NOs. 39 and 40, CDR 2 is $55^{th}$ to $61^{st}$ in the amino acid sequence of SEQ ID NOs. 39 and 40, and CDR 3 is $94^{th}$ to $102^{nd}$ in the amino acid sequence of SEQ ID NOs. 39 and 40. Further, the cysteine that can form a sulfide bond together with another light chain and can be bound to metal ion is the $219^{th}$ cysteine in the amino acid sequence of SEQ ID NO. 40.

The human antibody κ type light chain (W15), as shown in the following example, has cytotoxicity against cancer cells, particularly, ovarian cancer cells and leukemia cells. For this reason, the human antibody κ type light chain (W15) is suitable as an active ingredient of an anti-cancer drug. The active center of anti-cancer activity of the human antibody κ type light chain (W15) is located in a variable region, particularly, in a CDR sequence. Further, the binding point to the metal ion is cysteine at the C terminal. Therefore, the human antibody κ type light chain (W15) may be configured such that a region other than the variable region and the cysteine at the C terminal thereof is different from the amino acid sequence of SEQ ID NO. 40.

The human antibody κ type light chain according to the present invention may also be composed of a polypeptide represented by an amino acid sequence in which one or several amino acids of the amino acid sequence of SEQ ID NO. 39 are substituted, added, and deleted, or a polypeptide represented by an amino acid sequence which has 95% or more homology (sequence identity) with the amino acid sequence. The polypeptide may also be referred to as "a mutant of the human antibody κ type light chain (W15)".

The mutant of the human antibody κ type light chain (W15) used as the human antibody κ type light chain according to the present invention has the same anticancer effect as the human antibody κ type light chain (W15). Accordingly, the mutant of the human antibody κ type light chain (W15) is preferably a mutant in which CDR 1, CDR 2, and CDR 3, and cysteine at the C terminal thereof are identical to the amino acid sequence of SEQ ID NO. 39 or 40 (i.e., CDR 1, CDR 2, and CDR 3, and cysteine at the C terminal thereof are conserved), and a region other than CDR regions in the variable region and amino acids other than the $219^{th}$ cysteine at the C terminal thereof are mutated from the human antibody κ type light chain (W15).

The human antibody κ type light chain composed of the polypeptide in which a variable region is represented by amino acid sequence of SEQ ID NO. 41 is referred to as "human antibody κ type light chain (W17)". The human antibody κ type light chain (W17) may be a human antibody κ type light chain in which a known human antibody constant region is added to the above-mentioned variable region. In one embodiment, the full-length amino acid sequence is represented by SEQ ID NO. 42. The amino acid sequence of SEQ ID NO. 42 represents the full length of a wild-type human antibody type light chain represented by the amino acid sequence in which a variable region is represented by the amino acid sequence of SEQ ID NO. 41. In the human antibody type light chain (W17), CDR 1 is $24^{th}$ to $40^{th}$ in the amino acid sequence of SEQ ID NOs. 41 and 42, CDR 2 is $56^{th}$ to $62^{nd}$ in the amino acid sequence of SEQ ID NOs. 41 and 42, and CDR 3 is $95^{th}$ to $103^{rd}$ in the amino acid sequence of SEQ ID NOs. 41 and 42. Further, the cysteine that can form a sulfide bond together with another light chain and can be bound to metal ion is the $220^{th}$ cysteine in the amino acid sequence of SEQ ID NO. 42.

The human antibody κ type light chain (W17), as shown in the following example, has cytotoxicity against cancer cells, particularly, leukemia cells. For this reason, the human antibody κ type light chain (W17) is suitable as an active ingredient of an anti-cancer drug. The active center of anti-cancer activity of the human antibody type light chain (W17) is located in a variable region, particularly, in a CDR sequence. Further, the binding point to the metal ion is cysteine at the C terminal. Therefore, the human antibody κ type light chain (W17) may be configured such that a region other than the variable region and the cysteine at the C terminal thereof is different from the amino acid sequence of SEQ ID NO. 42.

The human antibody κ type light chain according to the present invention may also be composed of a polypeptide represented by an amino acid sequence in which one or several amino acids of the amino acid sequence of SEQ ID NO. 41 are substituted, added, and deleted, or a polypeptide represented by an amino acid sequence which has 95% or more homology (sequence identity) with the amino acid sequence. The polypeptide may also be referred to as "a mutant of the human antibody κ type light chain (W17)".

The mutant of the human antibody κ type light chain (W17) used as the human antibody κ type light chain according to the present invention has the same anticancer effect as the human antibody κ type light chain (W17). Accordingly, the mutant of the human antibody κ type light chain (W17) is preferably a mutant in which CDR 1, CDR 2, and CDR 3, and cysteine at the C terminal thereof are identical to the amino acid sequence of SEQ ID NO. 41 or 42 (i.e., CDR 1, CDR 2, and CDR 3, and cysteine at the C terminal thereof are conserved), and a region other than CDR regions in the variable region and amino acids other than the $220^{th}$ cysteine at the C terminal thereof are mutated from the human antibody κ type light chain (W17).

The human antibody κ type light chain composed of the polypeptide in which a variable region is represented by amino acid sequence of SEQ ID NO. 43 is referred to as "human antibody κ type light chain (W18)". The human antibody κ type light chain (W18) may be a human antibody κ type light chain in which a known human antibody constant region is added to the above-mentioned variable region. In one embodiment, the full-length amino acid sequence is represented by SEQ ID NO. 44. The amino acid sequence of SEQ ID NO. 44 represents the full length of a wild-type human antibody type light chain represented by the amino acid sequence in which a variable region is represented by the amino acid sequence of SEQ ID NO. 43. In the human antibody type light chain (W18), CDR 1 is $24^{th}$ to $39^{th}$ in the amino acid sequence of SEQ ID NOs. 43 and 44, CDR 2 is $55^{th}$ to $61^{st}$ in the amino acid sequence of SEQ ID NOs. 43 and 44, and CDR 3 is $94^{th}$ to $102^{nd}$ in the amino acid sequence of SEQ ID NOs. 43 and 44. Further, the cysteine that can form a sulfide bond together with another light chain and can be bound to metal ion is the $219^{th}$ cysteine in the amino acid sequence of SEQ ID NO. 44.

The human antibody κ type light chain (W18), as shown in the following example, has cytotoxicity against cancer cells, particularly, leukemia cells. For this reason, the human antibody κ type light chain (W18) is suitable as an active ingredient of an anti-cancer drug. The active center of anti-cancer activity of the human antibody type light chain (W18) is located in a variable region, particularly, in a CDR sequence. Further, the binding point to the metal ion is cysteine at the C terminal. Therefore, the human antibody κ type light chain (W18) may be configured such that a region other than the variable region and the cysteine at the C terminal thereof is different from the amino acid sequence of SEQ ID NO. 44.

The human antibody κ type light chain according to the present invention may also be composed of a polypeptide represented by an amino acid sequence in which one or several amino acids of the amino acid sequence of SEQ ID NO. 43 are substituted, added, and deleted, or a polypeptide represented by an amino acid sequence which has 95% or more homology (sequence identity) with the amino acid sequence. The polypeptide may also be referred to as "a mutant of the human antibody κ type light chain (W18)".

The mutant of the human antibody κ type light chain (W18) used as the human antibody κ type light chain according to the present invention has the same anticancer effect as the human antibody κ type light chain (W18). Accordingly, the mutant of the human antibody κ type light chain (W18) is preferably a mutant in which CDR 1, CDR 2, and CDR 3, and cysteine at the C terminal thereof are identical to the amino acid sequence of SEQ ID NO. 43 or 44 (i.e., CDR 1, CDR 2, and CDR 3, and cysteine at the C terminal thereof are conserved), and a region other than CDR regions in the variable region and amino acids other than the $219^{th}$ cysteine at the C terminal thereof are mutated from the human antibody κ type light chain (W18).

The human antibody κ type light chain composed of the polypeptide in which a variable region is represented by amino acid sequence of SEQ ID NO. 45 is referred to as "human antibody κ type light chain (W19)". The human antibody κ type light chain (W19) may be a human antibody κ type light chain in which a known human antibody constant region is added to the above-mentioned variable region. In one embodiment, the full-length amino acid sequence is represented by SEQ ID NO. 46. The amino acid sequence of SEQ ID NO. 46 represents the full length of a wild-type human antibody κ type light chain represented by the amino acid sequence in which a variable region is represented by the amino acid sequence of SEQ ID NO. 45. In the human antibody κ type light chain (W19), CDR 1 is $24^{th}$ to $40^{th}$ in the amino acid sequence of SEQ ID NOs. 45 and 46, CDR 2 is $56^{th}$ to $62^{nd}$ in the amino acid sequence of SEQ ID NOs. 45 and 46, and CDR 3 is $95^{th}$ to $102^{nd}$ in the amino acid sequence of SEQ ID NOs. 45 and 46. Further, the cysteine that can form a sulfide bond together with another light chain and can be bound to metal ion is the $219^{th}$ cysteine in the amino acid sequence of SEQ ID NO. 46.

The human antibody κ type light chain (W19), as shown in the following example, has cytotoxicity against cancer cells, particularly, ovarian cancer cells. For this reason, the human antibody κ type light chain (W19) is suitable as an active ingredient of an anti-cancer drug. The active center of anti-cancer activity of the human antibody κ type light chain (W19) is located in a variable region, particularly, in a CDR sequence. Further, the binding point to the metal ion is cysteine at the C terminal. Therefore, the human antibody κ type light chain (W19) may be configured such that a region other than the variable region and the cysteine at the C terminal thereof is different from the amino acid sequence of SEQ ID NO. 46.

The human antibody κ type light chain according to the present invention may also be composed of a polypeptide represented by an amino acid sequence in which one or several amino acids of the amino acid sequence of SEQ ID NO. 45 are substituted, added, and deleted, or a polypeptide represented by an amino acid sequence which has 95% or more homology (sequence identity) with the amino acid sequence. The polypeptide may also be referred to as "a mutant of the human antibody κ type light chain (W19)".

The mutant of the human antibody κ type light chain (W19) used as the human antibody κ type light chain according to the present invention has the same anticancer effect as the human antibody κ type light chain (W19). Accordingly, the mutant of the human antibody κ type light chain (W19) is preferably a mutant in which CDR 1, CDR 2, and CDR 3, and cysteine at the C terminal thereof are identical to the amino acid sequence of SEQ ID NO. 45 or 46 (i.e., CDR 1, CDR 2, and CDR 3, and cysteine at the C terminal thereof are conserved), and a region other than CDR regions in the variable region and amino acids other than the $219^{th}$ cysteine at the C terminal thereof are mutated from the human antibody κ type light chain (W19).

The human antibody κ type light chain composed of the polypeptide in which a variable region is represented by amino acid sequence of SEQ ID NO. 47 is referred to as "human antibody κ type light chain (W21)". The human antibody κ type light chain (W21) may be a human antibody κ type light chain in which a known human antibody constant region is added to the above-mentioned variable region. In one embodiment, the full-length amino acid sequence is represented by SEQ ID NO. 48. The amino acid sequence of SEQ ID NO. 48 represents the full length of a wild-type human antibody κ type light chain represented by the amino acid sequence in which a variable region is represented by the amino acid sequence of SEQ ID NO. 47. In the human antibody type light chain (W21), CDR 1 is $24^{th}$ to $39^{th}$ in the amino acid sequence of SEQ ID NOs. 47 and 48, CDR 2 is $55^{th}$ to $61^{st}$ in the amino acid sequence of SEQ ID NOs. 47 and 48, and CDR 3 is $94^{th}$ to $102^{nd}$ in the amino acid sequence of SEQ ID NOs. 47 and 48. Further, the cysteine that can form a sulfide bond together with another light chain and can be bound to metal ion is the $219^{th}$ cysteine in the amino acid sequence of SEQ ID NO. 48.

The human antibody κ type light chain (W21), as shown in the following example, has cytotoxicity against cancer cells, particularly, ovarian cancer cells. For this reason, the human antibody κ type light chain (W21) is suitable as an active ingredient of an anti-cancer drug. The active center of anti-cancer activity of the human antibody κ type light chain (W21) is located in a variable region, particularly, in a CDR sequence. Further, the binding point to the metal ion is cysteine at the C terminal. Therefore, the human antibody κ type light chain (W21) may be configured such that a region other than the variable region and the cysteine at the C terminal thereof is different from the amino acid sequence of SEQ ID NO. 48.

The human antibody κ type light chain according to the present invention may also be composed of a polypeptide represented by an amino acid sequence in which one or several amino acids of the amino acid sequence of SEQ ID NO. 47 are substituted, added, and deleted, or a polypeptide represented by an amino acid sequence which has 95% or more homology (sequence identity) with the amino acid sequence. The polypeptide may also be referred to as "a mutant of the human antibody κ type light chain (W21)".

The mutant of the human antibody κ type light chain (W21) used as the human antibody κ type light chain according to the present invention has the same anticancer effect as the human antibody κ type light chain (W21). Accordingly, the mutant of the human antibody κ type light chain (W21) is preferably a mutant in which CDR 1, CDR 2, and CDR 3, and cysteine at the C terminal thereof are identical to the amino acid sequence of SEQ ID NO. 47 or 48 (i.e., CDR 1, CDR 2, and CDR 3, and cysteine at the C terminal thereof are conserved), and a region other than CDR regions in the variable region and amino acids other than the $219^{th}$ cysteine at the C terminal thereof are mutated from the human antibody κ type light chain (W21).

The human antibody κ type light chain composed of the polypeptide in which a variable region is represented by amino acid sequence of SEQ ID NO. 49 is referred to as "human antibody κ type light chain (W26)". The human antibody κ type light chain (W26) may be a human antibody κ type light chain in which a known human antibody constant region is added to the above-mentioned variable region. In one embodiment, the full-length amino acid sequence is represented by SEQ ID NO. 50. The amino acid sequence of SEQ ID NO. 50 represents the full length of a wild-type human antibody κ type light chain represented by the amino acid sequence in which a variable region is represented by the amino acid sequence of SEQ ID NO. 49. In the human antibody κ type light chain (W26), CDR 1 is $24^{th}$ to $39^{th}$ in the amino acid sequence of SEQ ID NOs. 49 and 50, CDR 2 is $55^{th}$ to $61^{st}$ in the amino acid sequence of SEQ ID NOs. 49 and 50, and CDR 3 is $94^{th}$ to $102^{nd}$ in the amino acid sequence of SEQ ID NOs. 49 and 50. Further, the cysteine that can form a sulfide bond together with another light chain and can be bound to metal ion is the $219^{th}$ cysteine in the amino acid sequence of SEQ ID NO. 50.

The human antibody κ type light chain (W26), as shown in the following example, has cytotoxicity against cancer cells, particularly, leukemia cells. For this reason, the human antibody κ type light chain (W26) is suitable as an active ingredient of an anti-cancer drug. The active center of anti-cancer activity of the human antibody κ type light chain (W26) is located in a variable region, particularly, in a CDR sequence. Further, the binding point to the metal ion is cysteine at the C terminal. Therefore, the human antibody κ type light chain (W26) may be configured such that a region other than the variable region is different from the amino acid sequence of SEQ ID NO. 50.

The human antibody κ type light chain according to the present invention may also be composed of a polypeptide represented by an amino acid sequence in which one or several amino acids of the amino acid sequence of SEQ ID NO. 49 are substituted, added, and deleted, or a polypeptide represented by an amino acid sequence which has 95% or more homology (sequence identity) with the amino acid sequence. The polypeptide may also be referred to as "a mutant of the human antibody κ type light chain (W26)".

The mutant of the human antibody κ type light chain (W26) used as the human antibody κ type light chain according to the present invention has the same anticancer effect as the human antibody κ type light chain (W26). Accordingly, the mutant of the human antibody κ type light chain (W26) is preferably a mutant in which CDR 1, CDR 2, and CDR 3, and cysteine at the C terminal thereof are identical to the amino acid sequence of SEQ ID NO. 49 or 50 (i.e., CDR 1, CDR 2, and CDR 3, and cysteine at the C terminal thereof are conserved), and a region other than CDR regions in the variable region and amino acids other than the $219^{th}$ cysteine at the C terminal thereof are mutated from the human antibody κ type light chain (W26).

The human antibody κ type light chain composed of the polypeptide in which a variable region is represented by amino acid sequence of SEQ ID NO. 51 is referred to as "human antibody κ type light chain (W28)". The human antibody κ type light chain (W28) may be a human antibody κ type light chain in which a known human antibody constant region is added to the above-mentioned variable region. In one embodiment, the full-length amino acid sequence is represented by SEQ ID NO. 52. The amino acid sequence of SEQ ID NO. 52 represents the full length of a wild-type human antibody κ type light chain represented by the amino acid sequence in which a variable region is represented by the amino acid sequence of SEQ ID NO. 51. In the human antibody κ type light chain (W28), CDR 1 is $24^{th}$ to $39^{th}$ in the amino acid sequence of SEQ ID NOs. 51 and 52, CDR 2 is $55^{th}$ to $61^{st}$ in the amino acid sequence of SEQ ID NOs. 51 and 52, and CDR 3 is $94^{th}$ to $102^{nd}$ in the amino acid sequence of SEQ ID NOs. 51 and 52. Further, the cysteine that can form a sulfide bond together with another light chain and can be bound to metal ion is the $219^{th}$ cysteine in the amino acid sequence of SEQ ID NO. 52.

The human antibody κ type light chain (W28), as shown in the following example, has cytotoxicity against cancer cells, particularly, leukemia cells. For this reason, the human antibody κ type light chain (W28) is suitable as an active ingredient of an anti-cancer drug. The active center of anti-cancer activity of the human antibody κ type light chain (W28) is located in a variable region, particularly, in a CDR sequence. Further, the binding point to the metal ion is cysteine at the C terminal. Therefore, the human antibody κ type light chain (W28) may be configured such that a region other than the variable region and the cysteine at the C terminal thereof is different from the amino acid sequence of SEQ ID NO. 52.

The human antibody κ type light chain according to the present invention may also be composed of a polypeptide represented by an amino acid sequence in which one or several amino acids of the amino acid sequence of SEQ ID NO. 51 are substituted, added, and deleted, or a polypeptide represented by an amino acid sequence which has 95% or more homology (sequence identity) with the amino acid sequence. The polypeptide may also be referred to as "a mutant of the human antibody κ type light chain (W28)".

The mutant of the human antibody κ type light chain (W28) used as the human antibody κ type light chain according to the present invention has the same anticancer effect as the human antibody κ type light chain (W28). Accordingly, the mutant of the human antibody κ type light chain (W28) is preferably a mutant in which CDR 1, CDR 2, and CDR 3, and cysteine at the C terminal thereof are identical to the amino acid sequence of SEQ ID NO. 51 or 52 (i.e., CDR 1, CDR 2, and CDR 3, and cysteine at the C terminal thereof are conserved), and a region other than CDR regions in the variable region and amino acids other than the $219^{th}$ cysteine at the C terminal thereof are mutated from the human antibody κ type light chain (W28).

The human antibody κ type light chain according to the present invention may include an additional polypeptide. Examples of the additional polypeptide include epitope-tagged polypeptides, such as His-tagged polypeptide, Myc-tagged polypeptide, and Flag-tagged polypeptide.

Those skilled in the art can easily mutate one or several amino acids of amino acid residues constituting a polypeptide or add an epitope-tagged polypeptide using well known techniques. For example, according to a known point mutagenesis, it is possible to mutate any base of a polynucleotide encoding a polypeptide. Further, it is possible to fabricate a deleted mutant or an added mutant by designing a primer corresponding to any site of the polynucleotide encoding the polypeptide.

The human antibody κ type light chain according to the present invention includes products produced from natural purified products, products of chemical synthetic procedures, and prokaryotic hosts or eukaryotic hosts (for example, bacterial cells, yeast cells, higher plant cells, insect cells, and mammal cells) by recombination techniques. Depending on the host used in the recombinant production procedure, the human antibody κ type light chain according to the present invention can either be glycosylated or unglycosylated. Further, in some cases, the human antibody κ type light chain according to the present invention can include an initial modified methionine residue as the result of a host-mediated process.

The human antibody κ type light chain according to the present invention may be a polypeptide formed by the peptide bonds of amino acids, but is not limited thereto. The human antibody κ type light chain according to the present invention may also be a complex polypeptide having a structure other than the polypeptide. As used herein, examples of the "structure other than the polypeptide" may include, but are not limited to, a sugar chain and an isoprenoid group.

The human antibody κ type light chain according to the present invention can be prepared by an expression system known in the art, such as a recombinant expression system or a cell-free expression system, using a vector including a polynucleotide encoding this human antibody κ type light chain (polypeptide).

In the case where the recombinant expression system is used, there can be employed a method of purifying a polypeptide, in which the polypeptide is obtained by embedding a polynucleotide encoding the human antibody κ type light chain according to the present invention into a recombinant expression vector, introducing a host capable of being expressed by a known manner, and then performing translation in the host (transformant). The recombinant expression vector may be a plasmid or may not be a plasmid as long as it is possible to introduce a target polynucleotide into the host.

When a foreign polynucleotide is introduced into such a host, it is preferable that the expression vector be embedded with a promoter functioning to express the foreign polynucleotide in the host. The method of purifying the recombinantly-produced polypeptide may be varied depending on the host used or the properties of a polypeptide, but it is possible to comparatively easily purify a target polypeptide by using a tag.

In the case where the cell-free expression system (cell-free protein synthesis system) is used, it is preferable to purify a polypeptide, which is synthesized by adding a polynucleotide encoding the human antibody κ type light chain according to the present invention to a solution containing ingredients necessary for the translation and synthesis of a protein, such as ribosome or t-RNA, and then incubating the resulting solution at an appropriate temperature.

Examples of the cell-free protein synthesis system include a system using a wheat germ extract, a system using a rabbit reticulocyte extract, a system using an *Escherichia coli* S30 extract, and a system using a cellular component extract obtained from the de-vacuolated protoplast of plants. Generally, in the translation of eukaryotic genes, a system of eukaryotic cells, that is, any of a system using a wheat germ extract and a system using a rabbit reticulocyte extract is selected. However, in view of the origin of translated genes (prokaryotes/eukaryotes) and the intended use of proteins after synthesis, the above synthesis system may be selected.

As these synthesis systems, various commercially-available kits may be used.

Meanwhile, since various virus-derived gene products frequently express activity through a complex biochemical reaction in which intracellular membranes, such as endoplasmic reticula, Golgi bodies, and the like, after the translation thereof, it is required that intracellular components (for example, microsomal membrane) are added in order to reproduce various biochemical reactions in a test tube. Since the cellular component extract obtained from the de-vacuolated protoplast of plants can be used as a cell-free protein synthesis liquid, the addition of microsomal membranes is not required, so it is preferable.

As used herein, the "intracellular membrane components" refer to cell organelles (that is, endoplasmic reticulum, Golgi body, mitochondria, chloroplast, and intracellular granules such as vacuoles). Particularly, endoplasmic reticulum and Golgi body play an important role in the modification of proteins after translation, and are cell components essential for the maturation of membrane proteins and secretory proteins.

It is preferable that the human antibody κ type light chain synthesized by the expression system and cell-free protein synthesis system of a host be purified. The process of purifying the human antibody κ type light chain is preferably a process in which a cell extract is prepared from cells and tissues by a well known method (for example, a method of recovering a soluble fraction by destroying cells and tissues and then centrifugally separating the destroyed cells and tissues), and then this cell extract is purified by a well known method (for example, ammonium sulfate precipitation or ethanol precipitation, acid extraction, anion or cation exchange chromatography, phosphocellulose chromatography, hydrophobic interaction chromatography, affinity chromatography, hydroxyapatite chromatography, and lectin chromatography). However, the process of purifying the human antibody κ type light chain is not limited thereto. Most preferably, high performance liquid chromatography ("HPLC") is used for the purification.

In addition, the human antibody κ type light chain according to the present invention can also be purified from cells or tissues naturally expressing this human antibody κ type light chain. For example, it is possible to identify cells and tissues naturally expressing the human antibody κ type light chain according to the present invention, using an antibody or an oligonucleotide. The purification of the human antibody κ type light chain from cells and tissues can be performed in the same manner as in the case of purifying the human antibody κ type light chain synthesized using the expression system of a host.

In addition, the human antibody κ type light chain according to the present invention can also be chemically synthesized. The method of chemically synthesizing the human antibody κ type light chain is not particularly limited, and may be performed by any method used at the time of chemically synthesizing a polypeptide.

<Complex-Containing Composition>

The complex-containing composition according to the present invention is a composition containing a complex in which the human antibody κ type light chain according to the present invention is bound to the metal ion.

The complex-containing composition according to the present invention is not particularly limited as long as it contains a complex in which the human antibody κ type light chain according to the present invention is bound to the metal ion. The complex-containing composition may include a human antibody heavy chain or may not include a human antibody heavy chain, but, preferably, does not contain a human antibody heavy chain.

In the complex-containing composition according to the present invention, 0.1 mol or more of the metal ion is bound per 1 mol of the human antibody κ type light chain. As the binding amount of the metal ion per 1 mol of the human antibody κ type light chain increases, the activity, such as cytotoxicity, of the human antibody κ type light chain tends to become higher.

In the complex-containing composition according to the present invention, the binding amount ratio (molar ratio) of the metal ion to the human antibody κ type light chain is a ratio of the total number of molecules of the metal ion bound to the human antibody κ type light chain in the composition to the total number of molecules of the human antibody κ type light chain included in the composition. In other words, the "composition containing a complex in which 0.1 mol or more of the metal ion is bound per 1 mol of the human antibody κ type light chain" means that, when 10 mol of the human antibody κ type light chain is included in the composition, 1 mol of the metal ion bound to the human antibody κ type light chain is included in the composition. Here, in the composition, a human antibody κ type light chain of a dimer will be measured as a human antibody κ type light chain of two molecules. Further, the composition may include a human antibody κ type light chain of a dimer bound via a metal ion, or may further include a human antibody κ type light chain of a monomer.

The amount of the metal ion bound to the human antibody κ type light chain included in the complex-containing composition according to the present invention can be measured by a general method, such as a colorimetric determination method, in which the complex-containing composition is previously subjected to dialysis treatment to remove free metal ions, the human antibody κ type light chain is denatured by a denaturing agent, and then the amount thereof is measured.

The complex-containing composition according to the present invention is obtained by bringing the human antibody κ type light chain according to the present invention in contact with the metal ions to bind the metal ions to at least a part of the human antibody κ type light chain. For example, the complex-containing composition according to the present invention can be prepared by incubating the human antibody κ type light chain according to the present invention in a solution containing the metal ions.

The human antibody κ type light chain incubated with metal ions may be a human antibody κ type light chain containing a large amount of foreign substances, but is more preferably a crude purified product or a purified product, from the viewpoint of quality control. Further, the human antibody κ type light chain may be incubated with metal ions in a solution in which dimers and monomers of the human antibody κ type light chain are mixed, and the human antibody κ type light chain purified to contain only the dimers may also be incubated with metal ions.

The incubation time of the human antibody κ type light chain according to the present invention and the metal ions can be appropriately determined in consideration of the kind of human antibody κ type light chain, the kind of metal ion, solvent, incubation temperature, and the like, such that a sufficient amount of metal ions can be bound to the human antibody κ type light chain. For example, when incubation is performed at room temperature for 30 minutes to 48 hours, a complex-containing composition in which 0.1 mol or more of the metal ion is bound per 1 mol of the human antibody κ type light chain can be easily obtained.

The complex-containing composition according to the present invention can also be prepared by bringing the human antibody κ type light chain into contact with the metal ions during the synthesis reaction of the human antibody κ type light chain and the purification process thereafter.

When the human antibody κ type light chain is expressed by an intracellular or extracellular expression system using an expression vector containing a polynucleotide encoding the human antibody κ type light chain, the metal ions are previously placed in the expression system. Thus, since the human antibody κ type light chain is expressed in the presence of the metal ions and the expressed human antibody κ type light chain is rapidly brought into contact with the metal ions, the human antibody κ type light chain is purified from the expression product by a general method, such as a column chromatography method, thereby obtaining a complex-containing composition containing a human antibody κ type light chain bound to the metal ions. As the method of previously placing the metal ions in the expression system, there is exemplified a method of adding metal ions to a culture medium for expressing cells or an extracellular expression system.

Further, when the human antibody κ type light chain is expressed by an intracellular or extracellular expression system, generally, the expressed human antibody κ type light chain is purified from the expression product by various purification methods. The human antibody κ type light chain is purified from a mixture obtained by adding the metal ions to the expression product after expression and thus it is possible to obtain human antibody κ type light chain complex-containing composition which bonds to the metal ion. Since the added metal ions can be sufficiently brought into contact with the human antibody κ type light chain, it is preferable that the mixture obtained by the addition of the metal ions be provided in the purification of the human antibody κ type light chain after being incubated for 30 minutes to 48 hours.

When the human antibody κ type light chain is prepared by an expression process of expressing the human antibody κ type light chain by an intracellular or extracellular system using an expression vector containing a polynucleotide encoding the human antibody κ type light chain and a process of purifying the human antibody κ type light chain from the expression product obtained from the expression process, the human antibody κ type light chain may be expressed in the presence of the metal ions, and the human antibody κ type light chain may also be purified from the mixture obtained by adding the metal ions to the expression product obtained from the expression process. Further, the human antibody κ type light chain may also be purified after adding the metal ions to the expression product obtained by expressing the human antibody κ type light chain in the presence of the metal ions, and, if necessary, performing incubation for an appropriate time.

In addition, the metal ions may be added during the purification process. For example, when the purification process is performed by a first purification process of obtaining a crude purified product containing the human antibody κ type light chain from the expression product obtained in the expression process by column chromatography using a column containing a first filler and a second purification process of obtaining a purified product of the human antibody κ type light chain from the crude purified product obtained in the first purification process by column chromatography using a column containing a second filler, a complex-containing composition containing the human antibody κ type light chain bound to the metal ions can be obtained by adding the metal ions to the crude purified product obtained in the first purification process before the second purification process. Since the added metal ions can be sufficiently brought into contact with the human antibody κ type light chain to be bound to the human antibody κ type light chain, it is preferable that the crude purified product added with the metal ions be incubated for 30 minutes to 48 hours, and is then provided to the second purification process. Further, even when the metal ions are added before the second purification process after the first purification process, the metal ions may be added into the expression system in the expression process.

When the purification process is performed by two-step column chromatography, the combination of the first filler and the second filler is not particularly limited as long as the human antibody κ type light chain can be finally purified to a desired degree of purification. The combination thereof can be appropriately determined in consideration of the kind of the human antibody κ type light chain and the presence or absence of addition and modification. For example, in the case where the human antibody κ type light chain to be synthesized using an expression system is an epitope-tagged polypeptide added with a His tag, it is preferable that a filler having high affinity for tagged epitope be used as the first filler, and an anion or cation exchange chromatography be used as the second filler. In this case, the human antibody κ type light chain can be purified in the first purification process, and the human antibody κ type light chain can be fractionated by separating the monomer and dimer or by the presence or absence of metal ion bonds in the second purification process.

<Pharmaceutical Composition>

When a human antibody κ type light chain having at least one activity of amidase activity, nucleic acid degradation activity, cytotoxicity against cancer cells, and anti-viral activity is used as the human antibody κ type light chain according to the present invention, and the complex-containing composition according to the present invention also has any one activity of these activities. Therefore, the complex-containing composition according to the present invention is particularly suitably used as a pharmaceutical composition, such as anti-cancer drugs and antiviral drugs.

The anti-cancer drug according to the present invention (anti-cancer drug containing the complex-containing composition according to the present invention as an active ingredient) can be administered by direct injection for use for humans or animals. Further, the anti-cancer drug according to the present invention can be formulated for parenteral administration, mucosal administration, intramuscular administration, intravenous administration, subcutaneous administration, intraocular administration, or transdermal administration. Typically, protein contained in the composition can be administered in a dose of 0.01 to 30 mg/kg body weight, preferably 0.1 to 10 mg/kg body weight, and more preferably 0.1 to 1 mg/kg body weight.

The anti-cancer drug according to the present invention may include a pharmaceutically acceptable carrier, a diluent, or an excipient (may also include a combination thereof) in addition to the human antibody κ type light chain according to the present invention. The pharmaceutically acceptable carrier or the excipient for therapeutic use is well known in the pharmaceutical art, and examples thereof are described in Remington's Pharmaceutical Sciences, Mack Publishing Co. (edited by A. R. Gennaro, 1985). The pharmaceutically acceptable carrier, the diluent, or the excipient can be easily selected by those skilled in the art in accordance with the intended administration route and standard pharmaceutical practice. The anti-cancer drug according to the present invention may further include any suitable binder, a lubricant, a suspension agent, a coating agent, or a solubilizer.

The requirements for composition/formulation may vary depending on different delivery systems. The anti-cancer drug according to the present invention can be formulated using a mini pump or by a mucosal route, for example, can be formulated for delivery as a nasal spray or aerosol for inhalation or for parenteral delivery (here, the anti-cancer drug according to the present invention is formulated in an injectable form for delivery through an intravenous route, an intramuscular route, or a subcutaneous route). Alternatively, this formulation can be designed to be delivered by both routes. In addition, it is preferable that the anti-cancer drug be formulated in a form, such as a nasal spray or aerosol for inhalation, by which the anti-cancer drug can be efficiently delivered from the nose or bronchi to lung cells.

When the anti-cancer drug according to the present invention is used for in vivo administration, various techniques for improving the stability (serum half-life) of the human antibody κ type light chain, which is an active ingredient, in a living body can be used. For example, if a neonatal Fc receptor (FcRn) is bound to Fc, it is known that the serum half-life of an antibody, such as IgG; is extended (e.g., refer to Roopenian, D. C. et. al., Nat Rev Immunol vol. 7 715-725 (2007)), and the C terminal of the human antibody κ type light chain according to the present invention can be modified to have a binding activity to FcRn. Further, if the human antibody κ type light chain according to the present invention is tagged, polyethylene glycol (PEG) can also be added.

The anti-cancer drug according to the present invention, for example, can also be made into a kit together with the instructions for dosage modes. The kit can also include various medical drugs that can be used in combination with the anti-cancer drug according to the present invention.

Since the anti-cancer drug according to the present invention contains a human antibody κ type light chain having high recognition ability for a target molecule as an active ingredient, it does not exhibit cytotoxicity to a cancer cell whose surface is not provided with the target molecule of the human antibody κ type light chain. Therefore, the anti-cancer drug of the present invention is expected to be useful for identification of such cancers.

EXAMPLES

Next, the present invention will be described in more detail by the following examples. However, the present invention is not limited to these examples.

[Construction of Expression System of Human Antibody κ Type Light Chain]

In the following examples, a human antibody κ type light chain (#7_wt) composed of an amino acid sequence of SEQ ID NO. 2, a human antibody κ type light chain (#7_C219A) composed of an amino acid sequence in which the 219$^{th}$ cysteine of the amino acid sequence of SEQ ID NO. 2 is substituted with alanine, a human antibody type light chain (#7 VL) composed of an amino acid sequence of SEQ ID NO. 4, a human antibody κ type light chain (#7 VL(I)) composed of an amino acid sequence of SEQ ID NO. 6, a human antibody κ type light chain (#7 VL(RL)) composed of an amino acid sequence of SEQ ID NO. 8, a human antibody κ type light chain (#7 RL I) composed of an amino acid sequence of SEQ ID NO. 10, a human antibody κ type light chain (#4) composed of an amino acid sequence of SEQ ID NO. 12, a human antibody type light chain (#11) composed of an amino acid sequence of SEQ ID NO. 14, a human antibody κ type light chain (23D4) composed of an amino acid sequence of SEQ ID NO. 16, a human antibody κ type light chain (W3) composed of an amino acid sequence of SEQ ID NO. 18, a human antibody κ type light chain (W10) composed of an amino acid sequence of SEQ ID NO. 20, a human antibody κ type light chain (C51) composed of an amino acid sequence of SEQ ID NO. 22, a human antibody κ type light chain (C82) composed of an amino acid sequence of SEQ ID NO. 24, a human antibody κ type light chain (C89) composed of an amino acid sequence of SEQ ID NO. 26, and a human antibody κ type light chain (W15) composed of an amino acid sequence of SEQ ID NO. 40 were used.

These human antibody κ type light chains were respectively expressed by an *Escherichia coli* expression system. Specifically, the cDNA including a base sequence encoding each of the human antibody κ type light chains was introduced into a plasmid vector having a His tag sequence site, and the plasmid vector was introduced into *Escherichia coli*, so as to prepare transformants. When each of the transformants was cultured and the expression induction with IPTG was performed, it could be identified by western blotting using SDS-PAGE analysis and anti-human (Fab')$_2$ antibodies that the protein expressed in *Escherichia coli* is a human antibody light chain. The obtained human antibody light chain had M (methionine) at the N-terminal thereof, and had a plasmid vector-derived sequence LEHHHHHH (SEQ ID NO. 53).

[Expression and Purification of Human Antibody κ Type Light Chain]

The human antibody κ type light chain that is not bound to the metal ions was expressed and purified as follows.

First, the transformant prepared by introducing the expression vector into *Escherichia coli* was culture in a LB medium at 37° C. overnight, IPTG was added to the LB medium such that the final concentration thereof was 10 μM (μμmol/L), and then the transformant was further cultured at 18° C. overnight. After the culturing, a sodium chloride-containing tris-buffer (25 mM Tris-HCl, 0.25M NaCl, pH 8.0) was added to the bacterial body harvested from a culture by centrifugation, the bacterial body was pulverized by sonication, and then centrifugation was carried out, so as to recover a soluble fraction.

Next, as the first purification process, this soluble fraction was applied to a Ni-NTA column (Qiagen Inc.) filled with Ni-NTA agarose, a suitable amount of the sodium chloride-containing tris-buffer was passed through the Ni-NTA column to express a human antibody κ type light chain, and the expressed human antibody κ type light chain was adsorbed on the Ni-NTA column. Then, the human antibody κ type light chain was eluted from the Ni-NTA column using an imidazole-containing tris-buffer (25 mM Tris-HCl, 0.25M NaCl, imidazole, pH 8.0) having a gradient of imidazole concentration from 0.03 M to 0.3 M as an eluent, so as to recover a human antibody type light chain-containing fraction. The recovered human antibody κ type light chain-containing fraction was dialyzed with an acetic acid buffer (50 mM acetic acid, pH 5.5) at 4° C. for 12 to 24 hours.

Thereafter, as the second purification process, the dialyzed human antibody type light chain-containing fraction was applied to a cation exchange column (product number: SP-5PW, manufactured by TOSOH Corporation), a suitable amount of the acetic acid buffer was passed through the cation exchange column to express a human antibody type light chain, and the expressed human antibody κ type light chain was adsorbed on the cation exchange column. Then, the human antibody κ type light chain was eluted from the cation exchange column using a sodium chloride-containing acetic acid buffer (50 mM acetic acid, NaCl, pH 5.5) having a gradient of sodium chloride concentration from 0.15 M to 0.45 M as an eluent, so as to recover a human antibody κ type light chain-containing fraction. The recovered human antibody κ type light chain-containing fraction was dialyzed with a sodium chloride-containing tris-buffer (20 mM Tris-HCl, 0.15M NaCl, pH 8.5) at 4° C. for 12 to 24 hours, and then further dialyzed with PBS (pH 7.4) at 4° C. for 12 to 24 hours. The dialyzed product was used as a complex-containing composition.

[Measurement of the Amount of Copper Ions Bound to Human Antibody κ Type Light Chain in Complex-Containing Composition]

In the following examples, in order to calculate the binding amount (mol) of copper ions per 1 mol of a human antibody κ type light chain in the complex-containing composition, the total amount (mol) of the copper ions bound to the human antibody type light chain was measured by the following method. The measurement of the amount of the copper ions was carried out using measurements of copper ion amount, and was carried out using the commercially available measuring kit "metallo assay, low concentration copper measuring LS (urinary copper quantitative kit)" (manufactured by Metallogenics Co., Ltd.). Meanwhile, the complex-containing composition (sample) to be used for the measurement, if necessary, was previously dialyzed using a solvent containing no copper ions, such as PBS (phosphate buffered saline).

Specifically, first, 100 μL of a sample was put into each well of a low adsorption type 96 well plate, and 140 μL of R-A (buffer) and 3 μL of R-R (chelate reagent solution: 3,5-DiBr-PAESA (4-(3,5-dibromo-2-pyridylazo)-N-ethyl-N-(3-sulfopropyl) aniline derivative)), having previously been incubated at 37° C., were dispensed, followed by stirring with pipetting. After the addition of R-R or the like, incubation was carried out at 37° C. for 10 minutes, and then absorbance at 590 nm was measured using a plate reader "ImmunoMini NJ-2300" (manufactured by NALGENE NUNC LTD.). The copper concentration in the sample was calculated from the measurement values obtained using the calibration curve created using a kit-accompanying copper standard solution.

The content of copper in each complex-containing composition was calculated according to the following equation. In the equation, the "copper ion (M)" represents the total amount of copper ions bound to the human antibody κ type light chain in the complex-containing composition, and the "human antibody κ type light chain (M)" represents the total amount of the human antibody κ type light chain contained in the complex-containing composition.

$$\text{Copper content (\%)} = \frac{\text{copper ion } (M)}{\text{human antibody } \kappa \text{ type light chain } (M)} \times 100 \quad \text{[Equation 1]}$$

[Cytotoxicity Assay]

The cytotoxicity of each complex-containing composition to cancer cells was tested using cancer cell lines. As the cancer cell lines, A549 cell line (human alveolar epithelial cancer cell line), ES-2 cell line (human ovarian cancer cell line), MOLT-4 cell line (human acute lymphoblastic leukemia T cell line), BxPC-3 cell line (human pancreatic adenocarcinoma cell line), SNU-1 cell line (human metastatic gastric cancer cell line), and PANC-1 cell line (human pancreatic cancer cell line) were used.

In addition, as a control, WI-38 cell line (human fetal lung fibroblast cell line) was also used.

All of these cell lines were purchased from ATCC (American Type Culture Collection). Here, the A549 cell line was cultured using a 10% FCS (fetal calf serum)-containing F-12K culture medium by a general method, the ES-2 cell line was cultured using a 10% FCS-containing McCoy's 5A culture medium by a general method, each of the MOLT-4 cell line, SNU-1 cell line, and BxPC-3 cell line was cultured using a 10% FCS-containing RPMI-1640 culture medium by a general method, the PANC-1 cell line was cultured using a 10% FCS-containing DMEM culture medium by a general method, and the WI-38 cell line was cultured using a 10% FCS-containing EMEM culture medium by a general method.

First, after being recovered by thawing the frozen cancer cell lines, the recovered cancer cell lines were seeded in a 96-well plate by 100 μL to be 5×10$^3$ cells/well (the number of seeds was appropriately adjusted by cell species). After culturing was carried out at 37° C. for 24 hours, a culture medium to be added to the 96-well plate was removed by decantation, and then each complex-containing composition prepared at a concentration of about 1 mg/mL was added to each well by 100 μL. After culturing was carried out for 24 hours or 48 hours from the addition of the complex-containing composition (after cells are planted and cultivated for 48 hours or 72 hours), a WST-1 reagent (manufactured by Roche Inc.) was added to each well by 10 μL and incubated for 1, 1.5, and 2 hours to form a formazan dye, and then the absorbance (Abs at 450 nm) of the formazan dye was measured (WST assay). As a control, a human antibody κ type light chain not bound to metal ions or PBS was added instead of the complex-containing composition and cultured for 24 hours or 48 hours, and then WST assay was carried out. Based on the results of the obtained absorbance, the cell survival rate of the well added with the human antibody κ type light chain not bound to metal ions or the well added with the PBS was set to 100%, and the cell survival rate of each well was determined, so as to evaluate the cytotoxicity of the added complex-containing composition.

Meanwhile, in the case of the MOLT-4 cell line, from the time cells were seeded in the 96-well plate, each complex-containing composition prepared at a concentration of about 1 mg/mL was added to each well by 100 μL and cultured for 24 hours or 48 hours, and then WST assay was carried out.

[Cytotoxicity Assay in Tumor-Bearing Mouse Model]

The cytotoxicity of each complex-containing composition to cancer cells in a tumor-bearing mouse model was tested using tumor-bearing mouse models.

First, the ES-2 cell line (human ovarian cancer-derived cell) or the B-16 cell line (mouse melanoma-derived cell) was subcutaneously transplanted into a mouse to a concentration of 2.5×10$^6$ cells/mouse. The complex-containing composition was administered against tumors subcutaneously established in the mouse from the 4$^{th}$ day after cancer cell transplantation. The administration of the complex-containing composition was carried out by directly injecting the complex-containing composition into a plurality of sites in the subcutaneous tumor from the outside of the mouse body using a syringe. Further, the administration of the complex-containing composition was carried out once per day for 5 days, was stopped for 2 days, and was then further carried out once per day for 5 days (carried out for a total of 10 times). As a control, a group in which PBS is administered in the same schedule was provided instead of the complex-containing composition.

The volume of the subcutaneous tumor over time was measured from the outside of the mouse body, the volume of the subcutaneous tumor at the 1$^{st}$ day after cancer cell transplantation (next day after transplantation) was set to 1, and the relative tumor volume was determined, so as to evaluate the cytotoxicity of the complex-containing composition to cancer cells in the tumor-bearing mouse model.

Example 1

The influence of the timing of adding copper ions in the expression and purification processes on the cytotoxicity of the obtained composition was examined using the human antibody κ type light chain (#7_wt).

Specifically, as described in the [expression and purification of a human antibody κ type light chain], in the method of expressing and purifying human antibody κ type light chain in the absence of copper ions (control case), a composition containing the human antibody κ type light chain (#7_wt) was obtained by a preparation method (case 1) which was carried out in the same manner as in the above [expression and purification of a human antibody κ type light chain], except that copper ions were added to the eluent after Ni-NTA column purification to a final concentration of 15 μM, incubation was performed at 4° C. for 12 hours to 16 hours, and then dialysis was performed using the acetic acid buffer, or was obtained by a preparation method (case 2) which was carried out in the same manner as in the above [expression and purification of a human antibody κ type light chain], except that the transformant of *E. coli*, into which a vector for expressing the human antibody κ type light chain (#7_wt) was introduced, was cultured in a LB culture medium added with copper ions to a final concentration of 15 μM, copper ions were added to the eluent after Ni-NTA column purification to a final concentration of 15 μM, incubation was performed at 4° C. for 12 hours to 16 hours, and then dialysis was performed using the acetic acid buffer.

Figure 1B:
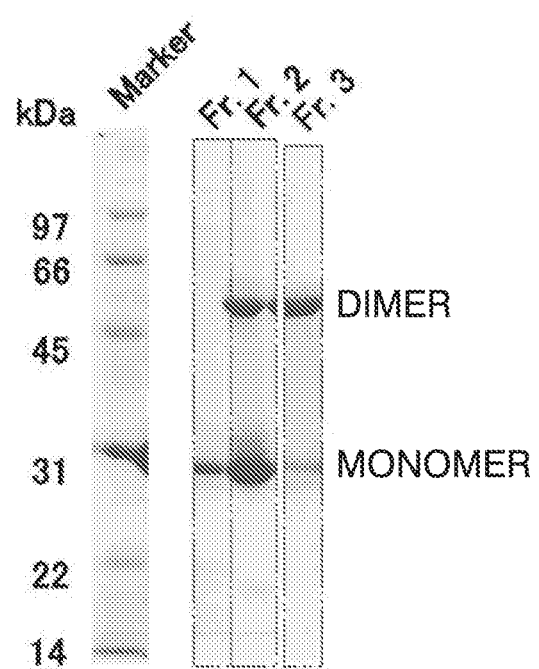
FIG. 1B is a view showing the results of SDS-PAGE (non-reduced) of each peak in the control case (copper ion-free) in Example 1.

FIG. 1A shows a cation exchange chromatogram (UV (280 nm) absorbance (mAu) and sodium chloride concentration (M) of an eluent in each retention time) in the control case (copper ion-free), and FIG. 1B shows the result of SDS-PAGE (non-reduced) of fractions 1 to 3 shown in FIG. 1A. The fraction 1 contains only the monomer of the human antibody κ type light chain (#7_wt). The fraction 2 contains both the monomer and dimer thereof, but contains a larger amount of monomers. The fraction 3 mainly contains dimers.

Figure 2A:
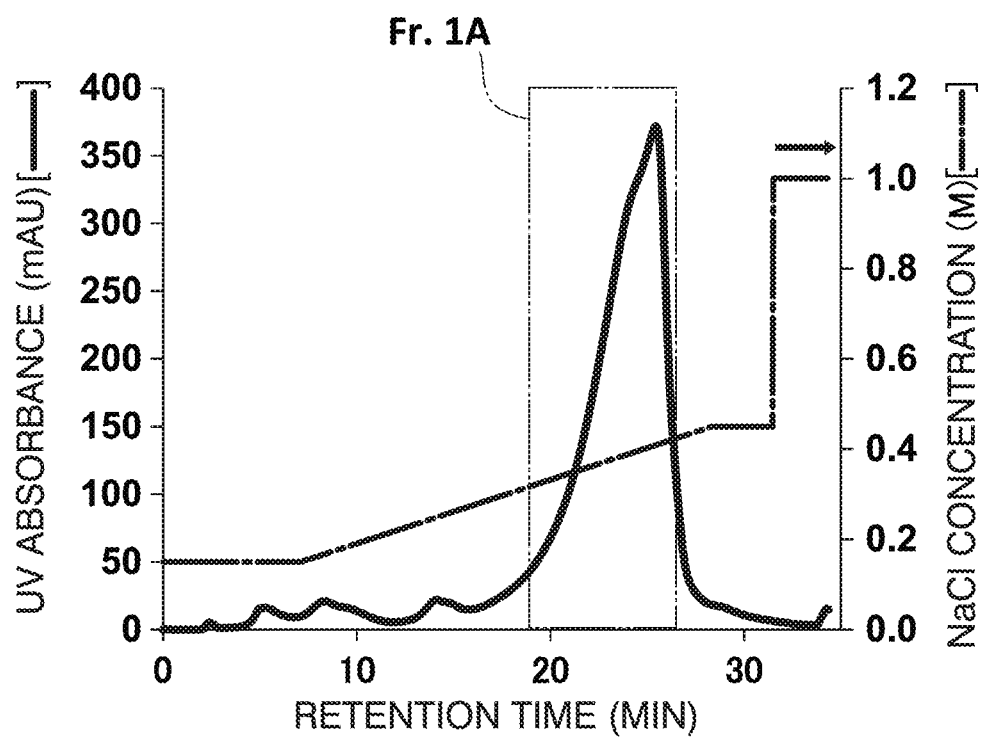
FIG. 2A is a graph showing the results of cation exchange chromatography in case 1 (addition of copper ion after primary purification) in Example 1.
Figure 2B:
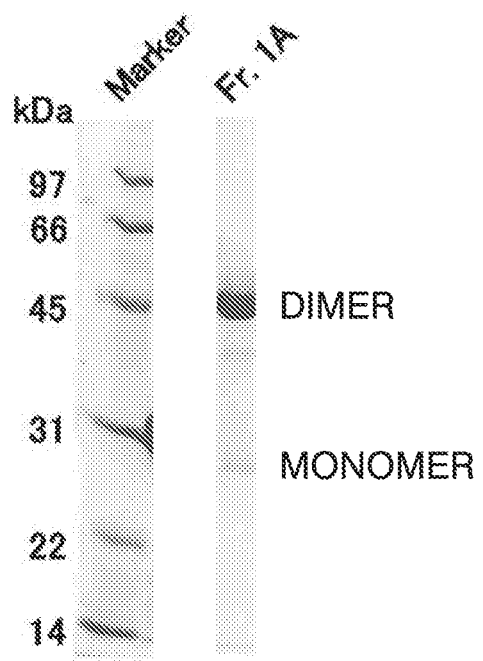
FIG. 2B is a view showing the results of SDS-PAGE (non-reduced) of each peak in case 1 (addition of copper ion after primary purification) in Example 1.

FIG. 2A shows a cation exchange chromatogram in the case 1 (addition of copper ions after primary purification), and FIG. 2B shows the result of SDS-PAGE (non-reduced) of fraction 1A shown in FIG. 2A. In the case 1, one large peak was observed at a position corresponding to the fraction 3 of the control case. According to the result of SDS-PAGE, it was found that the human antibody κ type light chain (#7_wt) contained in this fraction 1A is almost dimer, and dimers, compared to monomers, are easily formed by purification in the presence of copper ions.

Figure 3A:
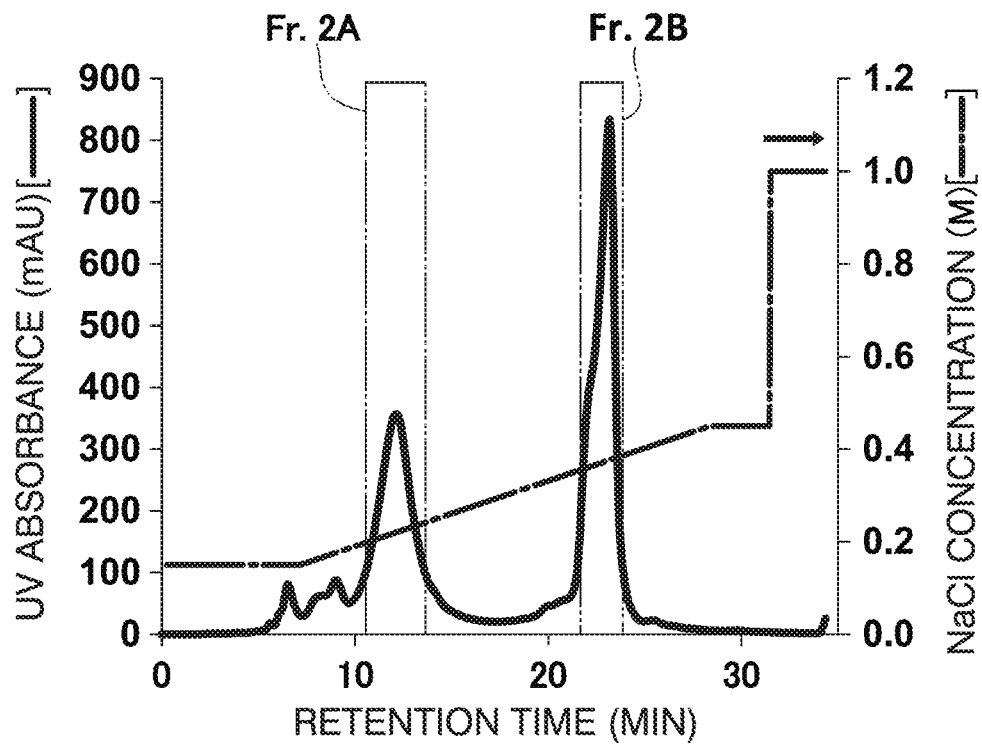
FIG. 3A is a graph showing the results of cation exchange chromatography in case 2 (addition of copper ion during expression and after primary purification) in Example 1.
Figure 3B:
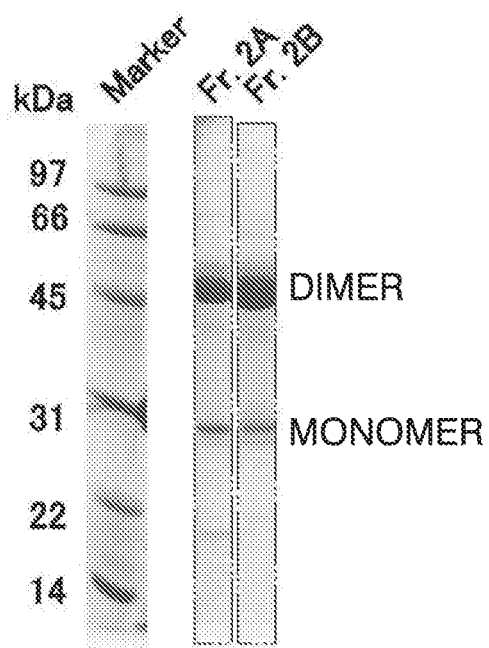
FIG. 3B is a view showing the results of SDS-PAGE (non-reduced) of each peak in case 2 (addition of copper ion during expression and after primary purification) of Example 1.

FIG. 3A shows a cation exchange chromatogram in the case 2 (addition of copper ions at the time of expression and after primary purification), and FIG. 3B shows the result of SDS-PAGE (non-reduced) of fractions 2A and 2B shown in FIG. 3A. In the case 2, peaks were observed at positions corresponding to the fractions 2 and 3 of the control case. According to the result of SDS-PAGE, it was found that the human antibody κ type light chains (#7_wt) contained in both fractions 2A and 2B are all substantially dimers, and, similarly to the case 1, dimers, compared to monomers, are easily formed by purification in the presence of copper ions.

Figure 4:
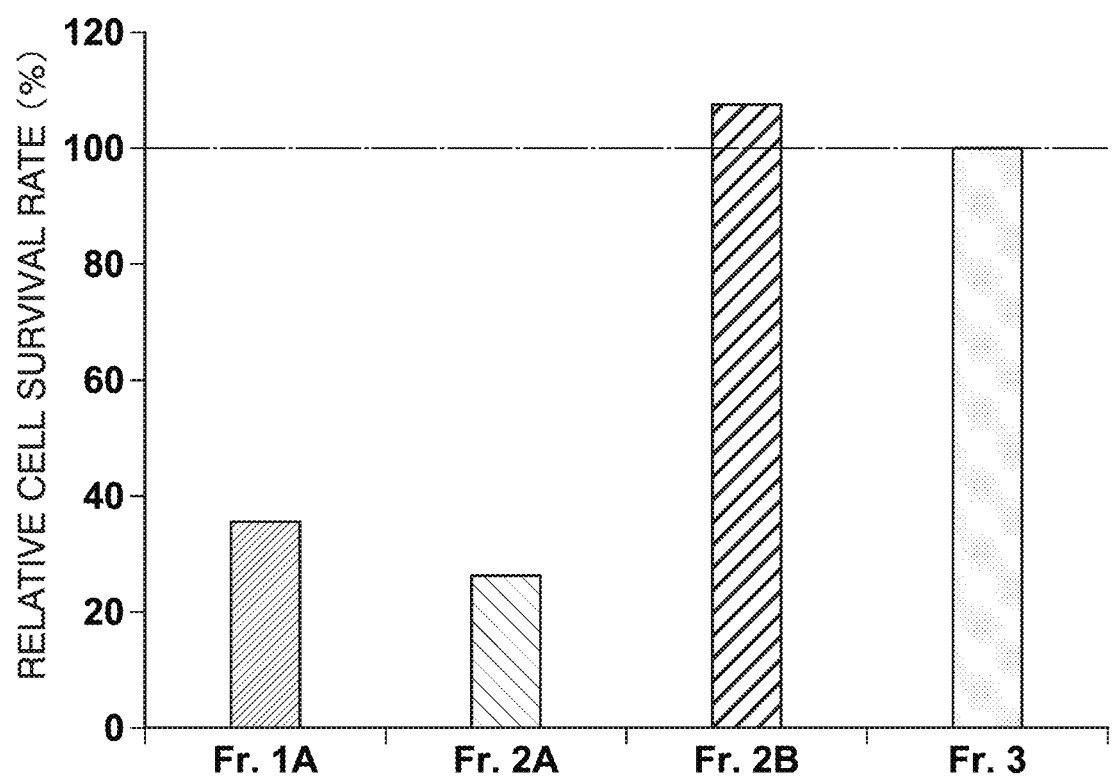
FIG. 4 is a graph showing the relative cell survival rate (%) in the case where composition (Fr. 1A) of fraction 1A of case 1, composition (Fr. 2A) of fraction 2A of case 2, and composition (Fr. 2B) of fraction 2B of case 2 in Example 1 were added, when the cell survival rate in the case where composition (Fr. 3) of fraction 3 of control case was added is set to 100%.

The cytotoxicity of the composition containing the human antibody κ type light chains (#7_wt) purified from each fraction to A549 cell line was examined. The human antibody κ type light chains (#7_wt) was added to each well to a concentration of 40 μM, and was then cultured for 24 hours. At this time, cell survival rate was measured. When the cell survival rate in the case of adding the composition (Fr. 3) of the fraction 3 of the control case was set to 100%, the relative cell survival rates in the cases of adding the composition (Fr. 1A) of the fraction 1A of the case 1, the composition (Fr. 2A) of the fraction 2A of the case 2, and the composition (Fr. 2B) of the fraction 2B of the case 2 were respectively measured. The results thereof are shown in FIG. 4. As a result, the Fr. 2B has a relative cell survival rate of greater than 100%, and has only the same degree of cytotoxicity as the Fr. 3 expressed and purified in the absence of copper ions. In contrast, each of the Fr. 1A and the Fr. 2A has a relative cell survival rate of lower than 40%, and has improved cytotoxicity compared to that of the Fr. 3 not bound to the copper ions.

When the UV/VIS spectra of the composition (Fr. 3) of the fraction 3 of the control case, the composition (Fr. 1A) of the fraction 1A of the case 1, the composition (Fr. 2A) of the fraction 2A of the case 2, and the composition (Fr. 2B) of the fraction 2B of the case 2 were measured, in the Fr. 1A and the Fr. 2A, peaks were observed in the vicinity of about 580 nm, whereas, in the Fr. 3 and the Fr. 2B, peaks were not observed. From the fact that copper ions has an absorption peak in the vicinity of about 580 nm, it was found that each of the Fr. 1A and the Fr. 2A contains the human antibody κ type light chain (#7_wt) bound to copper ions, and each of the Fr. 3 and the Fr. 2B does not contain the human antibody κ type light chain (#7_wt) bound to copper ions.

From these results, it was found that the cytotoxic activity of the human antibody κ type light chain (#7_wt) is remarkably improved by binding with copper ions.

Example 2

The cytotoxicity of each of the compositions, which were obtained by adding copper ions after the first purification process, performing incubation and then proving the resultant to the second purification process, was examined using the human antibody type light chain (#7_wt).

Specifically, a composition containing the human antibody κ type light chain (#7_wt) was obtained by a preparation method (case 3) which was carried out in the same manner as in the above [expression and purification of a human antibody κ type light chain], except that copper ions were added to the human antibody κ type light chain-containing fraction after Ni-NTA column purification to a final concentration of 15 μM, incubation was performed at 4° C. for 12 hours to 16 hours, dialysis was performed for 12 hours to 24 hours by the acetic acid buffer, and then the resultant fraction was applied to a cation exchange column, or was obtained by a preparation method (case 4) which was carried out in the same manner as in the above [expression and purification of a human antibody κ type light chain], except that copper ions were added to the human antibody κ type light chain-containing fraction after Ni-NTA column purification to a final concentration of 40 μM, incubation was performed at 4° C. for 12 hours to 16 hours, dialysis was performed for 12 hours to 24 hours by the acetic acid buffer, and then the resultant fraction was applied to a cation exchange column.

Figure 5:
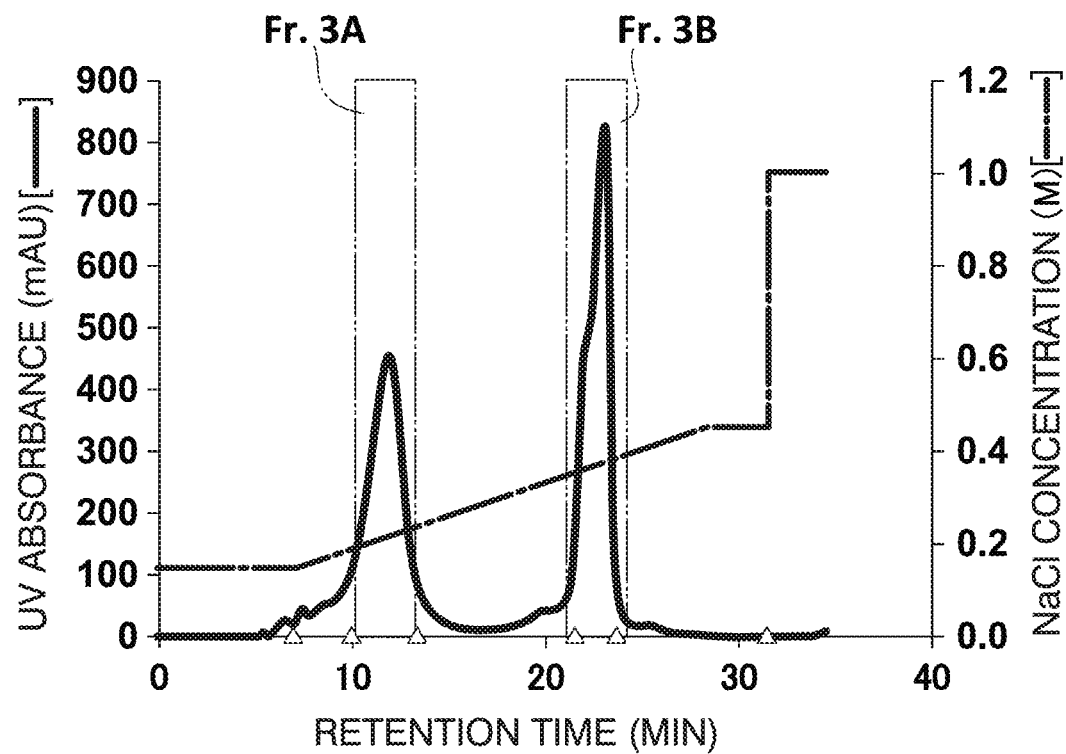
FIG. 5 is a graph showing the results of cation exchange chromatography in case 3 (incubation by addition of 15 μM copper ion after primary purification) in Example 2.
Figure 6:
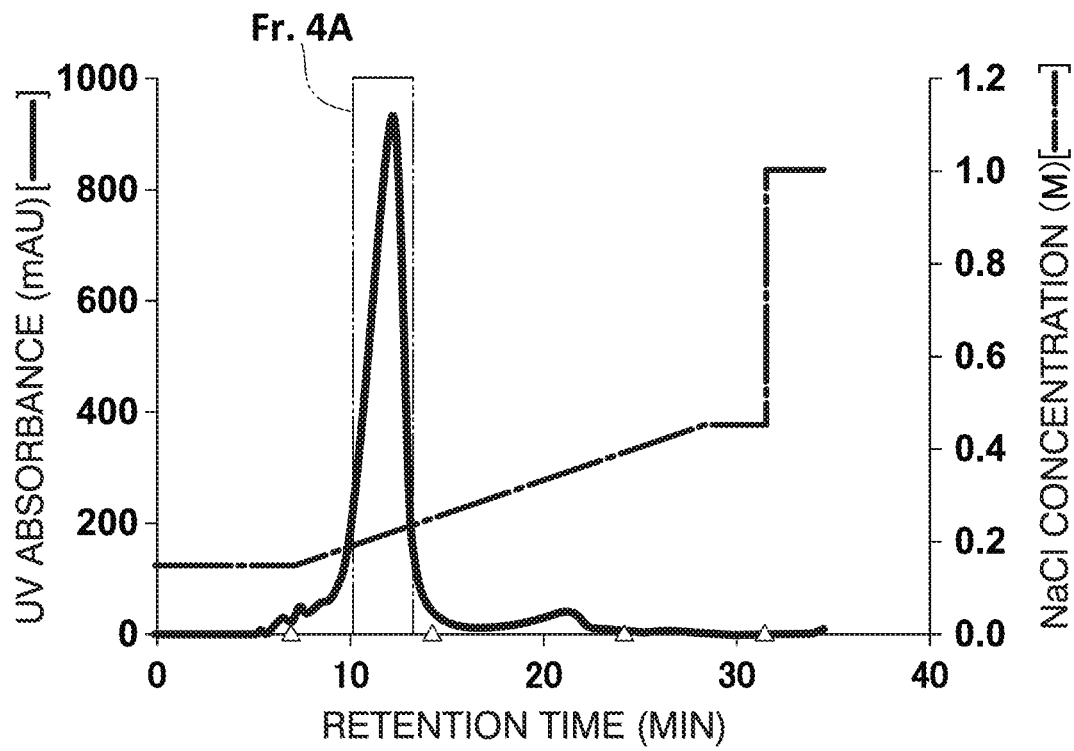
FIG. 6 is a graph showing the results of cation exchange chromatography in case 4 (incubation by addition of 40 μM copper ion after primary purification) in Example 2.

FIG. 5 shows a cation exchange chromatogram in the case 3 (15 μM copper ions were added and incubated after primary purification), and FIG. 6 shows a cation exchange chromatogram in the case 4 (40 μM copper ions were added and incubated after primary purification).

In the case 3, similarly to the case 2 of Example 1, two peaks were observed, and the fractions including two peaks were set as fractions 3A and 3B, respectively. Meanwhile, in the case 4, only one peak was observed at a position corresponding to the fraction 3A of the case 3, and the fraction including this peak was set as fraction 4A. When SDS-PAGE (non-reduced) for each fraction was performed, it was found that the human antibody κ type light chain (#7_wt) contained in both fractions 3A and 4A are all substantially dimers (results not shown).

Figure 7:
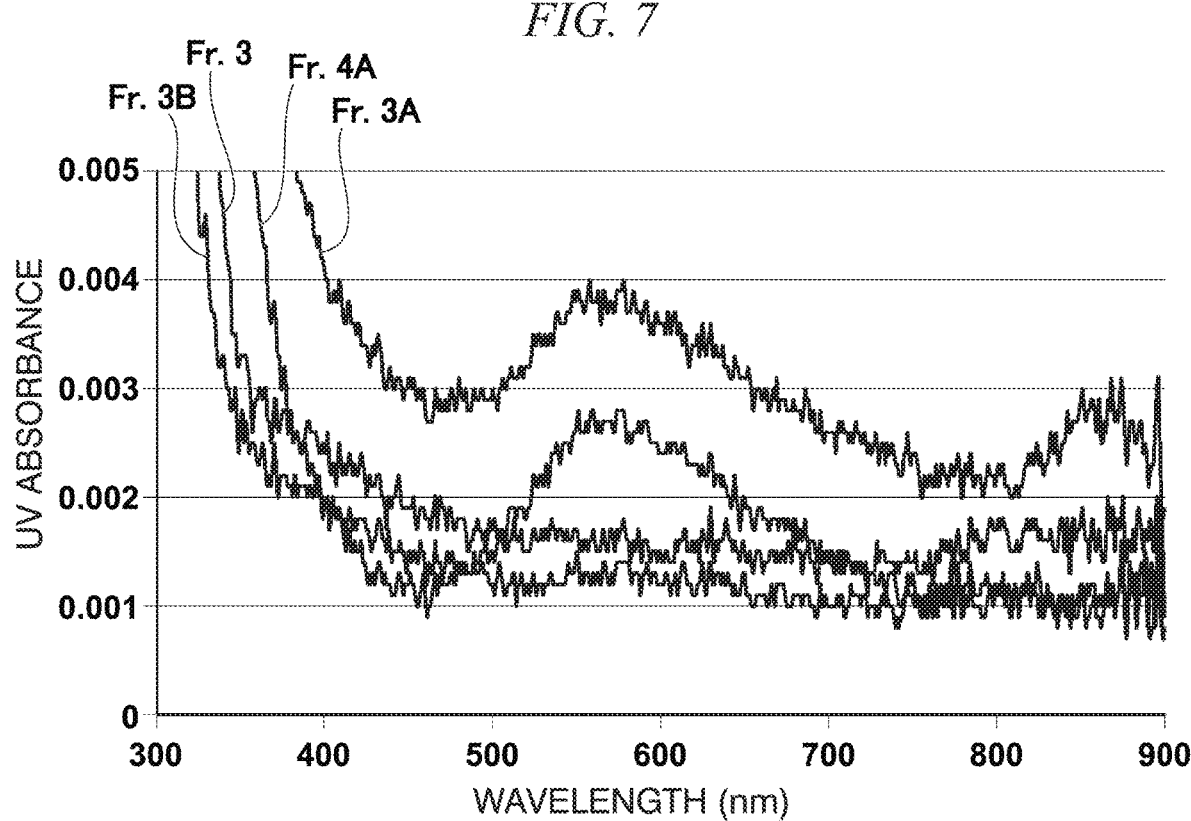
FIG. 7 is a graph showing the UV/VIS spectrum measurement results of composition (Fr. 3A) of fraction 3A of case 3, composition (Fr. 3B) of fraction 3B of case 3, and composition (Fr. 4A) of fraction 4A of case 4 in Example 2, together with the result of composition (Fr. 3) of fraction 3 of control case in Example 1.

The UV/VIS spectra of the composition (Fr. 3A) of the fraction 3A of the case 3, the composition (Fr. 3B) of the fraction 3B of the case 3, and the composition (Fr. 4A) of the fraction 4A of the case 4 were measured. The measurement results of UV/VIS spectra are shown in FIG. 7 together with the results of the composition (Fr. 3) of the fraction 3 of the control case in Example 1. As a result, in the Fr. 3A and the Fr. 4A, peaks were observed in the vicinity of about 580 nm, whereas, in the Fr. 3B, similarly to the Fr. 3, the peak was not observed.

The copper contents of the composition (Fr. 3A) of the fraction 3A of the case 3, the composition (Fr. 3B) of the fraction 3B of the case 3, and the composition (Fr. 4A) of the fraction 4A of the case 4 were measured. As a result, the copper content of the Fr. 3A was 47.5%, the copper content of the Fr. 3B was 3.2%, and the copper content of the Fr. 4A was 64.6% (Table 1).

The cytotoxicity of the composition containing the human antibody κ type light chains (#7_wt) purified from each fraction to SNU-1 cell line and PANC-1 cell line was examined. The human antibody κ type light chains (#7_wt) was added to each well to a concentration of 4 μM (100 μg/mL), and was then cultured for 24 hours or 48 hours. At this time, cell survival rate was measured. Further, the cytotoxicity thereof was examined in such a manner that cisplatin (anti-cancer drug) was added to a concentration of 4 μM or 33 μM as a positive control.

When the cell survival rate in the case of adding the Fr. 3B containing the human antibody κ type light chains (#7_wt) not bound to copper ions was set to 100%, the relative cell survival rates in the cases of adding the Fr. 3A, the Fr. 4A, and the cisplatin were respectively measured. The results thereof are shown in Table 1. As a result, each of the Fr. 3A and the Fr. 4A, each containing the human antibody κ type light chains (#7_wt) bound to copper ions, has a low relative cell survival rate to both the SNU-1 cell line and the PANC-1 cell line, and has improved cytotoxicity, compared to that of the Fr. 3B not bound to the copper ions.

TABLE 1

|  | Cisplatin (4 μM) | Cisplatin (33 μM) | Fr. 3A | Fr. 3B | Fr. 4A |
|---|---|---|---|---|---|
| Copper content (%) | — | — | 47.5 | 3.2 | 64.6 |
| Relative cell survival rate (%) | | | | | |
| SNU-1 cell line, 24 h | 85.0 | 32.0 | 85.1 | 100 | 81.8 |
| SNU-1 cell line, 48 h | 32.5 | 5.8 | 84.7 | 100 | 78.7 |
| PANC-1 cell line, 24 h | 109.3 | 60.3 | 75.2 | 100 | 70.5 |
| PANC-1 cell line, 48 h | 82.1 | 9.6 | 86.4 | 100 | 83.1 |

Example 3

The cytotoxicity of each of the compositions, which were obtained by adding copper ions after the first purification process, performing incubation and then proving the resultant to the second purification process, was examined using the human antibody κ type light chain (#7_C219A).

Specifically, as described in the [expression and purification of a human antibody κ type light chain], in the method of expressing and purifying human antibody type light chain in the absence of copper ions (control case), a composition containing the human antibody κ type light chain (#7_C219A) was obtained by a preparation method (case 3) which was carried out in the same manner as in the above [expression and purification of a human antibody κ type light chain], except that copper ions were added to the human antibody κ type light chain-containing fraction after Ni-NTA column purification to a final concentration of 15 μM, incubation was performed at 4° C. for 12 hours to 16 hours, dialysis was performed for 12 hours to 24 hours by the acetic acid buffer, and then the resultant fraction was applied to a cation exchange column, or was obtained by a preparation method (case 4) which was carried out in the same manner as in the above [expression and purification of a human antibody κ type light chain], except that copper ions were added to the human antibody κ type light chain-containing fraction after Ni-NTA column purification to a final concentration of 40 μM, incubation was performed at 4° C. for 12 hours to 16 hours, dialysis was performed for 12 hours to 24 hours by the acetic acid buffer, and then the resultant fraction was applied to a cation exchange column.

Figure 8:
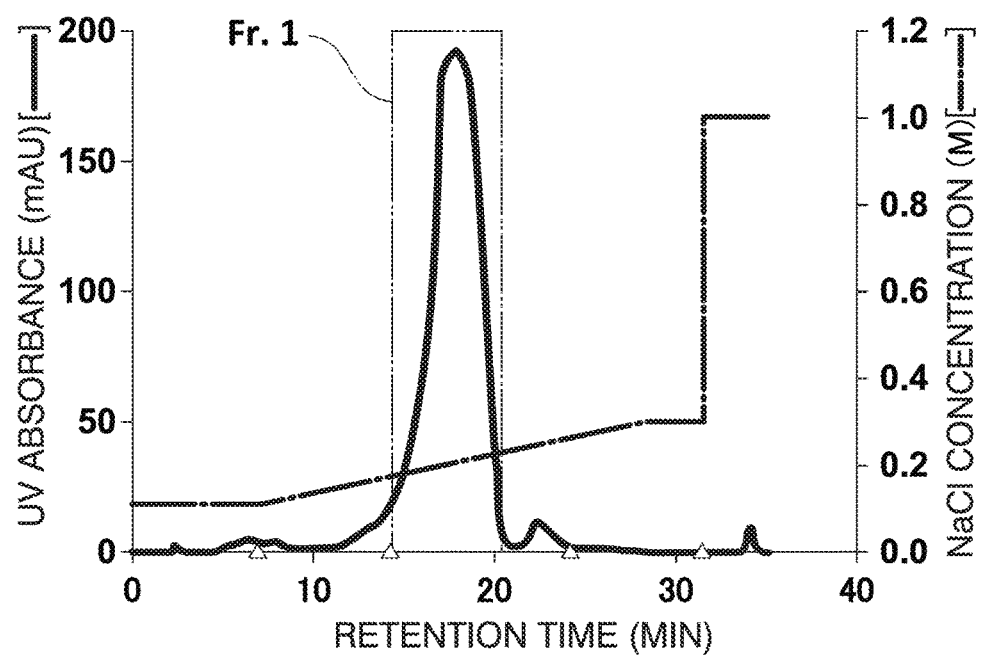
FIG. 8 is a graph showing the results of cation exchange chromatography in a control case (copper ion-free) and SDS-PAGE (non-reduced) of each peak in Example 3.
Figure 9:
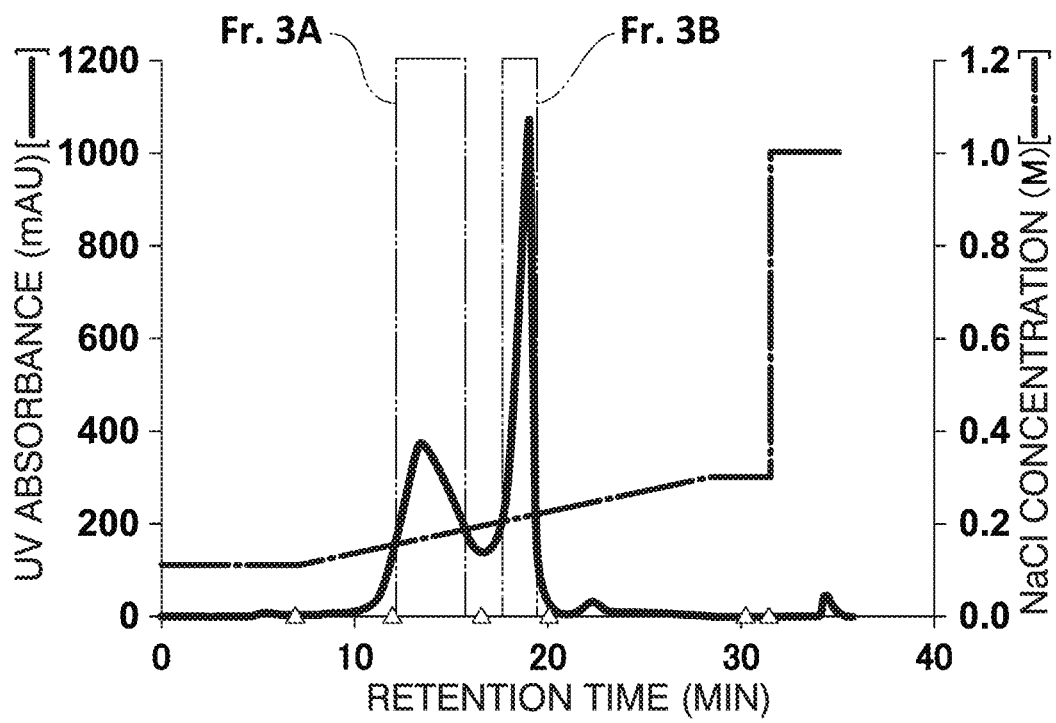
FIG. 9 is a graph showing the results of cation exchange chromatography in case 3 (incubation by addition of 15 μM copper ion after primary purification) in Example 3.
Figure 10:
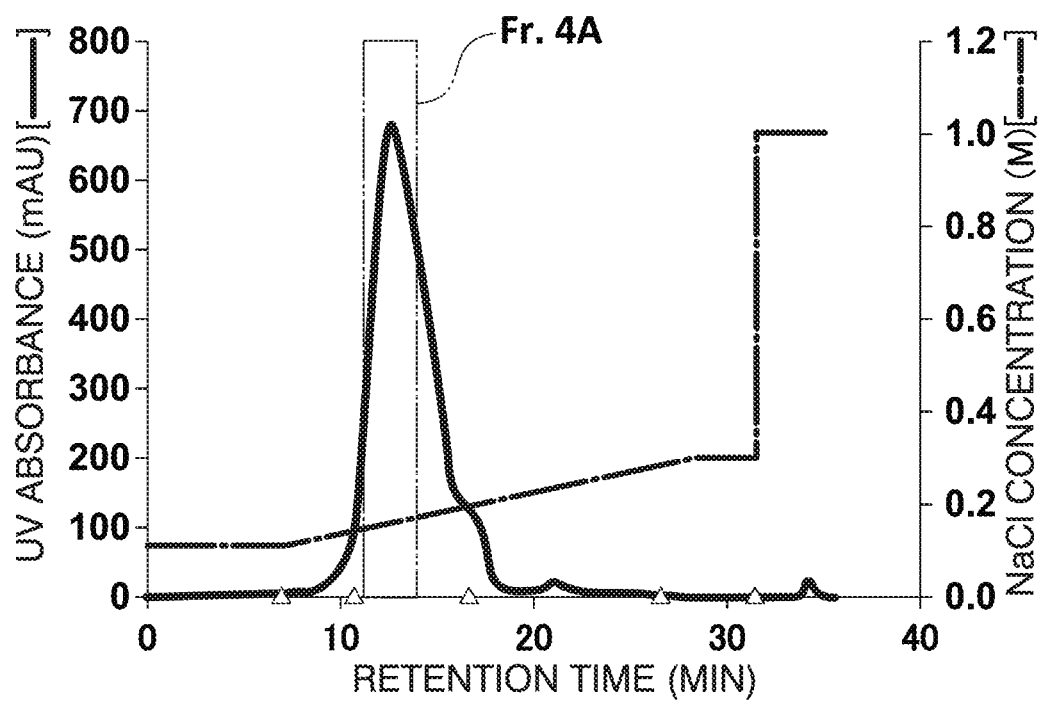
FIG. 10 is a graph showing the results of cation exchange chromatography in case 4 (incubation by addition of 40 μM copper ion after primary purification) in Example 3.

FIG. 8 shows a cation exchange chromatogram in the control case (copper ion-free), FIG. 9 shows a cation exchange chromatogram in the case 3 (15 μM copper ions were added and incubated after primary purification), and FIG. 10 shows a cation exchange chromatogram in the case 4 (40 μM copper ions were added and incubated after primary purification). In the control case, only one peak was observed at a position corresponding to the fraction 2 of the control case of Example 1, and the fraction including this peak was set as fraction 1. In the case 3, similarly to the case 3 of Example 2, two peaks were observed, and the fractions including these two peaks were set as fractions 3A and 3B, respectively. Meanwhile, in the case 4, similarly to the case 4 of Example 2, only one peak was observed, and the fraction including this peak was set as fraction 4A. When SDS-PAGE (non-reduced) for each fraction was performed, it was found that each of the fractions contains only the human antibody κ type light chain (#7_C219A), which is a monomer (results not shown).

Figure 11:
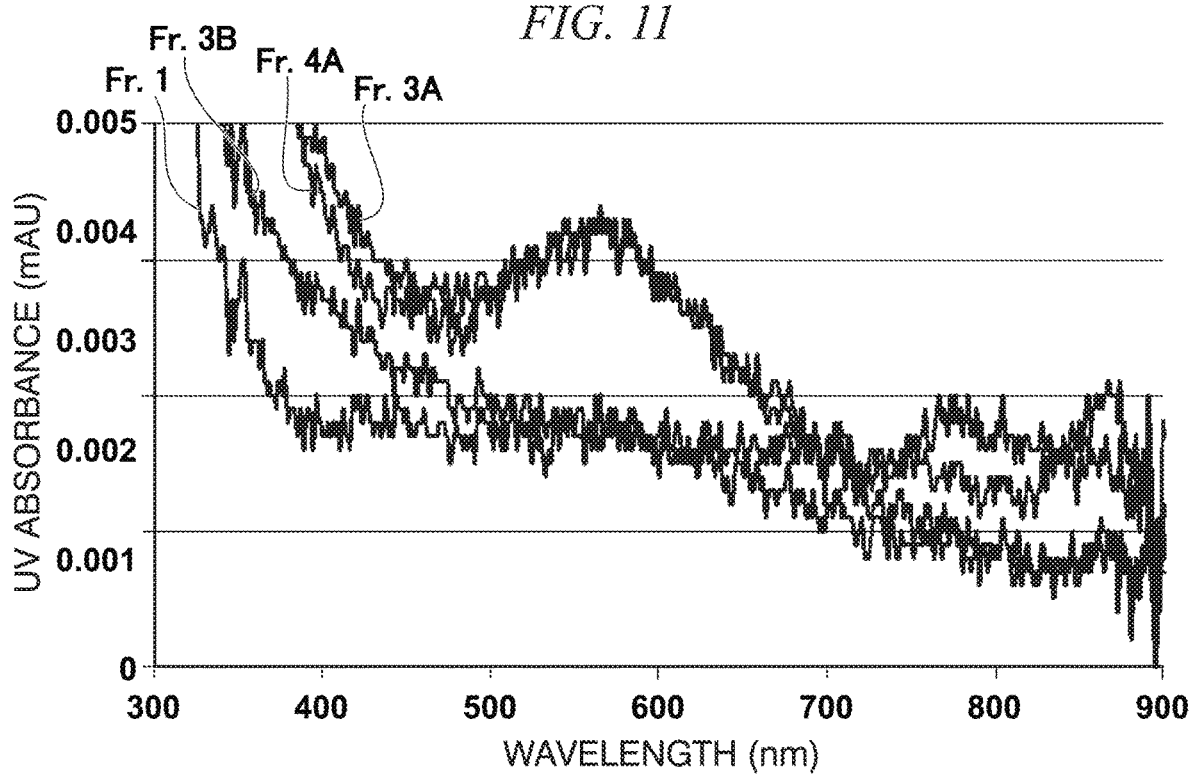
FIG. 11 is a graph showing the UV/VIS spectrum measurement results of composition (Fr. 1) of fraction 1 of control case, composition (Fr. 3A) of fraction 3A of case 3, composition (Fr. 3B) of fraction 3B of case 3, and composition (Fr. 4A) of fraction 4A of case 4 in Example 3.
Figure 12:
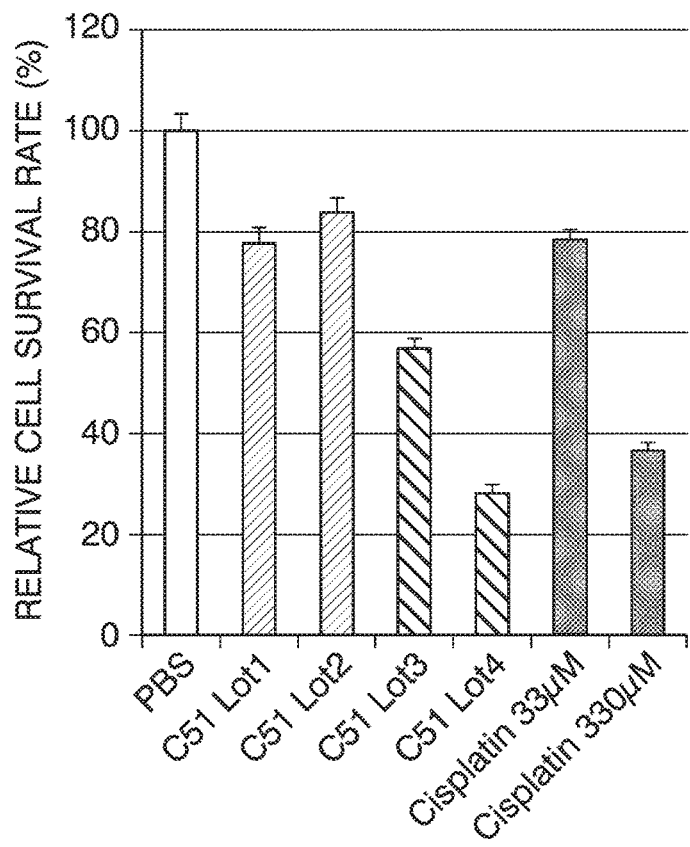
FIG. 12 is a graph showing the relative cell survival rate (%) in Example 4, in the case where each of the compositions was added, when the cell survival rate in the case where PBS was added is set to 100%.

The UV/VIS spectra of the composition (Fr. 1) of the fraction 1 of the control case, the composition (Fr. 3A) of the fraction 3A of the case 3, the composition (Fr. 3B) of the fraction 3B of the case 3, and the composition (Fr. 4A) of the fraction 4A of the case 4 were measured. The measurement results of UV/VIS spectra are shown in FIG. 11. As a result, in the Fr. 3A and the Fr. 4A, peaks were observed in the vicinity of about 580 nm, whereas, in the Fr. 3B, similarly to the Fr. 1, the peak was not observed.

The copper contents of the composition (Fr. 3A) of the fraction 3A of the case 3, the composition (Fr. 3B) of the fraction 3B of the case 3, and the composition (Fr. 4A) of the fraction 4A of the case 4 were measured. As a result, the copper content of the Fr. 3A was 37.5%, the copper content of the Fr. 3B was 7.4%, and the copper content of the Fr. 4A was 51.5% (Table 2).

The cytotoxicity of the composition containing the human antibody κ type light chains (#7_C219A) purified from each fraction to SNU-1 cell line was examined. The human antibody κ type light chains (#7_C219A) was added to each well to a concentration of 8.6 μM to 9.1 μM, and was then cultured for 24 hours. At this time, cell survival rate was measured. Further, the cytotoxicity thereof was examined in such a manner that cisplatin (anti-cancer drug) was added to a concentration of 4 μM as a positive control. When the cell survival rate in the case of adding the Fr. 3B containing the human antibody κ type light chains (#7_C219A) not bound to copper ions was set to 100%, the relative cell survival rates in the cases of adding the Fr. 3A, the Fr. 4A, and the cisplatin were respectively measured. The results thereof are shown in Table 2. As a result, each of the Fr. 3A and the Fr. 4A, each containing the human antibody κ type light chains (#7_C219A) bound to copper ions, has a low relative cell survival rate to both the SNU-1 cell line and the PANC-1 cell line, and has improved cytotoxicity, compared to that of the Fr. 3B not bound to the copper ions.

TABLE 2

|  | Cisplatin | Fr. 3A | Fr. 3B | Fr. 4A |
|---|---|---|---|---|
| Copper content (%) | — | 37.5 | 7.4 | 51.5 |
| Relative cell survival rate (%) | | | | |
| SNU-1 cell line, 24 h | 89.5 | 79.3 | 100 | 73.7 |

Example 4

The cytotoxicity of each of the compositions [C51 (Lot1) and C51 (Lot2)] obtained by expression and purification in the absence of copper ions, the composition [C51 (Lot3)] obtained by purification in the presence of copper ions, and the composition [C51 (Lot4)] obtained by expression and purification in the presence of copper ions, each composition containing the human antibody κ type light chain (C51), to A549 cell line was examined.

The compositions C51 (Lot1) and C51 (Lot2) were prepared by the above "expression and purification of human antibody κ type chain". In the cation chromatogram, in both of them, three peaks were obtained as in the control case of Example 1. However, only the fraction including peak 3 (fraction 3) was purified to examine cytotoxicity.

The composition C51 (Lot3) was prepared in the same manner as in the above "expression and purification of human antibody κ type chain", except that copper ions were added to the human antibody κ type light chain-containing fraction after Ni-NTA column purification to a final concentration of 15 μM, incubation was performed at 4° C. for 12 hours to 16 hours, and then dialysis was performed using the acetic acid buffer. In the cation chromatogram, one peak was obtained as in the case 1 of Example 1. Only the fraction (fraction 1A) including this peak was purified to examine cytotoxicity.

The composition C51 (Lot4) was prepared in the same manner as in the above "expression and purification of human antibody κ type chain", except that the transformant of *E. coli*, into which a vector for expressing the human antibody κ type light chain (C51) was introduced, was cultured in a LB culture medium added with copper ions to a final concentration of 15 μM, copper ions were added to the human antibody κ type light chain-containing fraction after Ni-NTA column purification to a final concentration of 15 μM, incubation was performed at 4° C. for 12 hours to 16 hours, and then dialysis was performed using the acetic acid buffer. In the cation chromatogram, two peaks were obtained as in the case 2 of Example 1. Only the fraction (fraction 2A) including the peak containing the human antibody κ type light chain (C51) bounded to copper ion, among these two peaks, was purified to examine cytotoxicity.

The cytotoxicity of the composition containing the human antibody κ type light chains (C51) purified from each fraction to A549 cell line was examined. The human antibody κ type light chain (C51) was added to each well to a concentration of 40 μM, and was then cultured for 24 hours. At this time, cell survival rate was measured.

Further, the cytotoxicity thereof was examined in such a manner that cisplatin (anti-cancer drug) was added to a concentration of 33 μM or 330 μM as a positive control, and PBS was added as a negative control. When the cell survival rate in the case of adding PBS was set to 100%, the relative cell survival rates in the cases of adding the compositions C51 (Lot1) to C51 (Lot4) and the cisplatin were respectively measured. The results thereof are shown in Table 12. As a result, it was found that the human antibody κ type light chain (C51) [C51 (Lot1) and C51 (Lot2)] not bound to copper ions exhibits cytotoxicity to the same degree in the case of addition of 33 μM cisplatin. Each of the compositions C51 (Lot3) and C51 (Lot4) containing the human antibody type light chains (C51) bound to copper ions, has a remarkably low relative cell survival rate, and has improved cytotoxicity, compared to the compositions C51 (Lot1) and C51 (Lot2).

Figure 13:
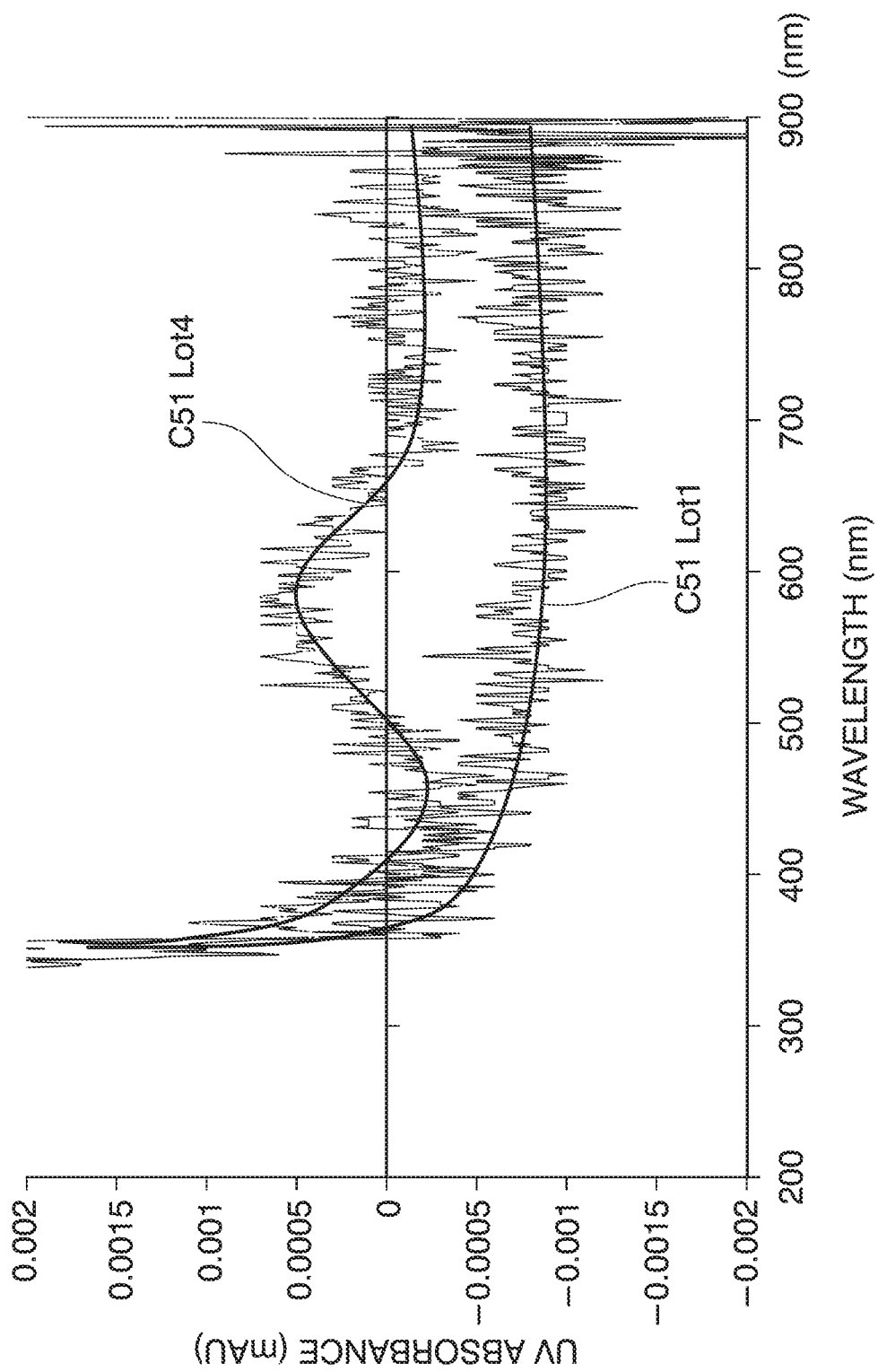
FIG. 13 is a graph showing the UV/VIS spectrum measurement results of C 51 (Lot 1) and C 51 (Lot 4) in Example 4.

The UV/VIS spectra of the compositions including the human antibody κ type light chain (C51) purified from each fraction were measured. The UV/VIS spectra measurement results of the compositions C51 (Lot1) to C51 (Lot4) are shown in FIG. 13. In the compositions C51 (Lot3) to C51 (Lot4), peaks were observed in the vicinity of about 580 nm, whereas, in the compositions C51 (Lot1) to C51 (Lot2), peaks were not observed. As a result, the binding site of the copper ion was estimated to be cysteine at the C terminal of human antibody κ type light chain.

Example 5

The cytotoxicity of the composition, which was obtained by incubating and binding the human antibody κ type light chains (C51) in the presence of various kinds of metal ions, to A549 cell line and WI-38 cell line was examined.

Specifically, first, a composition containing the human antibody κ type light chains (C51) was prepared in the same manner as in C51 (Lot1) of Example 4. Subsequently, trivalent iron ions, trivalent cobalt ions, trivalent nickel ions, trivalent copper ions, trivalent zinc ions, trivalent gold ions, trivalent silver ions, or trivalent platinum ions were added to a final concentration of 15 μM to a human antibody κ type light chain (C51) solution in which the final concentration of the human antibody κ type light chains (C51) was adjusted to 40 μM, and incubation was carried out for 24 hours. After the incubation, dialysis was repeatedly performed using PBS (pH 7.4) at 4° C. for 12 hours twice to obtain a composition, and this composition was used in cytotoxicity assay.

When the UV/VIS spectrum of each composition obtained by dialysis after incubation with copper ions was measured, peak was observed in the vicinity of about 580 nm. For this reason, it was found that the composition containing the human antibody κ type light chain bound to metal ions was obtained by incubating the purified human antibody κ type light chain bound with metal ions.

In the cytotoxicity assay, the human antibody κ type light chain (C51) was added to each well to a concentration of 4 μM, and was then cultured for 24 hours. At this time, cell survival rate was measured. Further, the cytotoxicity thereof was examined in such a manner that cisplatin (anti-cancer drug) was added to a concentration of 4 μM (A549 cell line) or 4.2 μM (WI-38 cell line) as a positive control, and PBS was added as a negative control. When the cell survival rate in the case of adding PBS was set to 100%, the relative cell survival rates in the case of adding each composition and cisplatin were respectively measured.

Figure 14:
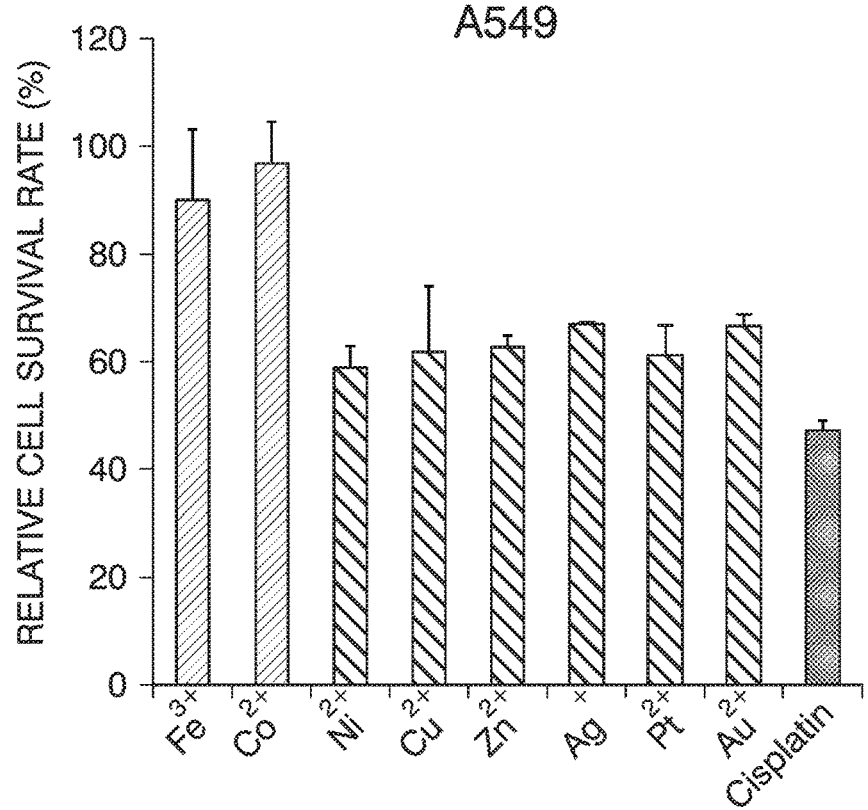
FIG. 14 is a graph showing the relative cell survival rate (%) in Example 5, using A 549 cell line, in the case where a human antibody κ type light chain (C51) bound to various metal ions was added, when the cell survival rate, in the case where PBS was added is set to 100%.
Figure 15:
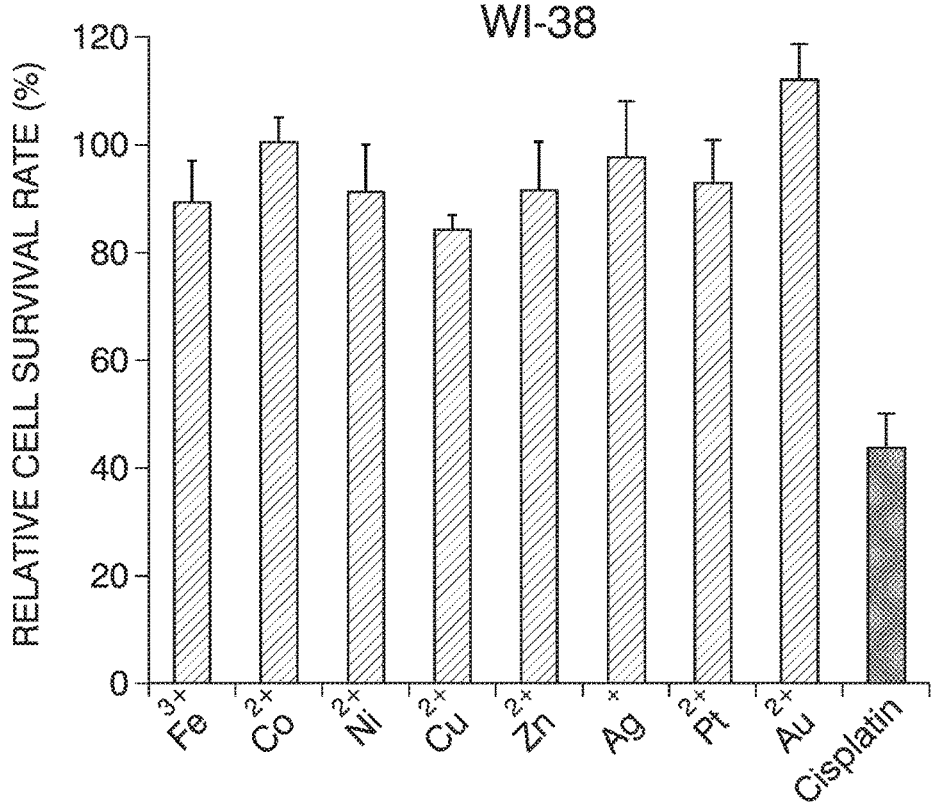
FIG. 15 is a graph showing the relative cell survival rate (%) in Example 5, using WI-38 cell line, in the case where a human antibody κ type light chain (C51) bound to various metal ions was added, when the cell survival rate, in the case where PBS was added is set to 100%.

The results for the A549 cell line are shown in FIG. 14, and the results for the WI-38 are shown in FIG. 15. As a result, in the A549 cell line, the human antibody κ type light chain (C51), which was incubated with nickel ions, copper ions, zinc ions, silver ions, or platinum ions, has a low relative cell survival rate of about 60% as in the case of addition of cisplatin, and has high cytotoxicity. Meanwhile, the human antibody κ type light chain (C51), which was incubated with iron ions or cobalt ions, has a relative cell survival rate of 90% or more, and cytotoxicity was not observed. In contrast, in the WI-38 cell line, in the case of addition of cisplatin, the relative cell survival rate was 40%, which is extremely low, whereas, in the case of the human antibody κ type light chain (C51) incubated with metal ions, the relative cell survival rate was 85% or more, which is high, regardless of the kind of metal ions, and the cytotoxicity was not observed. From these results, it was found that it is possible to improve cancer cell-specific cytotoxicity by binding a human antibody κ type light chain with metal ions of Group 10 elements, Group 11 elements, or Group 12 elements, such as copper ions.

Example 6

For various human antibody κ type light chains, the influence of the binding amount of copper ions on cytotoxicity against cancer cells was examined.

Specifically, first, a composition containing a human antibody κ type light chains was prepared in the same manner as in C51 (Lot1) of Example 4. Subsequently, copper ions were added to a human antibody κ type light chain solution in which the final concentration of this human antibody κ type light chain was adjusted to 40 μM, and incubation was carried out for 24 hours. After the incubation, dialysis was repeatedly performed using PBS (pH 7.4) at 4° C. for 12 hours twice to obtain a composition, and this composition was used in cytotoxicity assay.

In the cytotoxicity assay, at the time that each composition was added and then cultured for 24 hours, a cell survival rate was measured. Further, even for a human antibody κ type light chain not incubated with copper ions (human antibody κ type light chain not bound with copper ions), cytotoxicity was examined in the same manner. When the cell survival rate in the case of adding the human antibody κ type light chain not bound with copper ions was set to 100%, the relative cell survival rates in the case of adding each composition were respectively measured.

The human antibody κ type light chains, cancer cells, concentration (μM) of human antibody κ type light chain added to each well, and relative cell survival rates (%), which were used in the cytotoxicity assay, are shown in Tables 3 and 4.

From these results, it was found that the cytotoxicity against various cancer cells can be improved by binding various human antibody κ type light chains with copper ions.

TABLE 3

| Human antibody κ type light chain | Cancer cell line | Concentration of human antibody κ type light chain | Relative cell survival rate |
|---|---|---|---|
| #4 | A549 | 34.9 μM | 79.1% |
| #4 | A549 | 25.2 μM | 81.8% |
| #4 | ES-2 | 20 μM | 50.3% |
| #4 | MOLT-4 | 4 μM | 69.6% |
| #4 | MOLT-4 | 20 μM | 42.3% |
| #4 | MOLT-4 | 40.4 μM | 24.3% |
| #7_WT | A549 | 20 μM | 49.7% |
| #7_WT | A549 | 40 μM | 29.8% |
| #7_WT | SNU-1 | 40 μM | 67.2% |
| #7_WT | MOLT-4 | 4 μM | 70.0% |
| #7VL | A549 | 40 μM | 45.9% |
| #7VL | ES-2 | 40 μM | 35.7% |
| #7VL | MOLT-4 | 40 μM | 29.4% |
| #7VL(I) | A549 | 40 μM | 79.0% |
| #7VL(I) | ES-2 | 40 μM | 53.7% |
| #7VL(I) | MOLT-4 | 40 μM | 58.7% |
| #7VL(RL) | A549 | 40 μM | 48.0% |
| #7VL(RL) | ES-2 | 40 μM | 49.4% |
| #7VL(RL) | MOLT-4 | 40 μM | 32.4% |
| #7RL I | A549 | 40 μM | 41.9% |
| #7RL I | SNU-1 | 40 μM | 52.2% |
| #7RL I | BxPC-3 | 40 μM | 77.6% |
| #11 | A549 | 12.3 μM | 73.2% |
| #11 | A549 | 20 μM | 54.5% |
| #11 | ES-2 | 12.3 μM | 58.5% |
| #11 | ES-2 | 20 μM | 23.8% |
| 23D4 | A549 | 40 μM | 43.7% |
| 23D4 | ES-2 | 40 μM | 11.5% |
| 23D4 | MOLT-4 | 4 μM | 58.2% |
| W3 | A549 | 5.9 μM | 82.0% |
| W3 | SNU-1 | 5.9 μM | 60.5% |
| W3 | PANC-1 | 5.9 μM | 75.5% |
| W3 | BxPC-3 | 4 μM | 85.2% |
| W3 | ES-2 | 4 μM | 54.3% |
| W3 | MOLT-4 | 4 μM | 69.4% |
| W10 | A549 | 4 μM | 89.0% |
| W10 | BxPC-3 | 4 μM | 70.7% |
| W10 | ES-2 | 4 μM | 66.6% |
| W10 | MOLT-4 | 4 μM | 64.5% |

TABLE 4

| Human antibody κ type light chain | Cancer cell line | Concentration of human antibody κ type light chain | Relative cell survival rate |
|---|---|---|---|
| C51 | A549 | 4 μM | 62.6% |
| C51 | A549 | 40 μM | 36.8% |
| C51 | ES-2 | 40 μM | 51.2% |
| C51 | MOLT-4 | 4 μM | 74.5% |
| C51 | MOLT-4 | 40 μM | 1.6% |
| C82 | ES-2 | 40 μM | 45.5% |
| C89 | ES-2 | 40 μM | 52.9% |

Example 7

For various human antibody κ type light chains, the influence of the binding amount of copper ions on cytotoxicity against cancer cells was examined.

Specifically, first, a composition containing a human antibody κ type light chains was prepared in the same manner as in C51 (Lot1) of Example 4. Subsequently, copper ions were added to a human antibody κ type light chain solution in which the final concentration of this human antibody κ type light chain was adjusted to 40 μM, and incubation was carried out for 24 hours. After the incubation, dialysis was repeatedly performed using PBS (pH 7.4) at 4° C. for 12 hours twice to obtain a composition, and this composition was used in cytotoxicity assay. Further, for each composition, copper content was measured.

In the cytotoxicity assay, at the time that each composition was added and then cultured for 24 hours, a cell survival rate was measured. Further, even for a human antibody κ type light chain not incubated with copper ions (human antibody κ type light chain not bound with copper ions), cytotoxicity was examined in the same manner. When the cell survival rate in the case of adding the human antibody κ type light chain not bound with copper ions was set to 100%, the relative cell survival rates in the case of adding each composition were respectively measured.

The human antibody κ type light chains, cancer cells, concentration (μM) of human antibody κ type light chain added to each well, copper content (%) of the human antibody κ type light chain composition, and relative cell survival rates (%), which were used in the cytotoxicity assay, are shown in Table 5. As a result, even in all of the human antibody κ type light chains, the relative cell survival rate in the cancer cell line was low (about 85% or less), whereas the relative cell survival rate in the WI-38 cell line, which is a normal cell line, was high (about 90% or more). Even from these results, it was found that the cytotoxicity against, particularly, cancer cells can be improved by binding various human antibody κ type light chains with copper ions.

TABLE 5

| Human antibody κ type light chain | Cancer cell line | Concentration of human antibody κ type light chain | Copper content of human antibody κ type light chain | Relative cell survival rate |
|---|---|---|---|---|
| #4 | SNU-1 | 39.4 μM | 34% | 29.5% |
| #7_WT | PANC-1 | 7.3 μM | 41% | 65.9% |
| W2 | MOLT-4 | 4 μM | 66% | 55.0% |
| W2 | ES-2 | 4 μM | 66% | 76.6% |
| W4 | MOLT-4 | 4 μM | 56% | 62.2% |
| W4 | ES-2 | 4 μM | 56% | 72.0% |
| W4 | WI-38 | 4 μM | 56% | 90.4% |
| W7 | MOLT-4 | 4 μM | 57% | 57.9% |
| W7 | ES-2 | 4 μM | 57% | 82.9% |
| W7 | WI-38 | 4 μM | 57% | 94.5% |
| W8 | A549 | 4 μM | 72% | 80.6% |
| W8 | MOLT-4 | 4 μM | 72% | 66.1% |
| W8 | ES-2 | 4 μM | 72% | 82.1% |
| W8 | WI-38 | 4 μM | 72% | 103.1% |
| W11 | MOLT-4 | 4 μM | 68% | 63.3% |
| W11 | ES-2 | 4 μM | 68% | 68.0% |
| W11 | WI-38 | 4 μM | 68% | 92.0% |
| W14 | MOLT-4 | 4 μM | 70% | 63.5% |
| W14 | ES-2 | 4 μM | 70% | 72.5% |
| W15 | MOLT-4 | 4 μM | 37% | 85.1% |
| W15 | ES-2 | 4 μM | 37% | 84.7% |
| W17 | MOLT-4 | 4 μM | 66% | 48.3% |
| W18 | MOLT-4 | 4 μM | 39% | 60.8% |
| W21 | MOLT-4 | 4 μM | 79% | 52.4% |
| W26 | MOLT-4 | 4 μM | 57% | 70.5% |
| W28 | MOLT-4 | 4 μM | 77% | 49.1% |
| W19 | ES-2 | 4 μM | 67% | 72.6% |

Example 7

Each of the human antibody κ type light chains (W15 and #4) was bound with copper ions by performing incubation in the presence of copper ions to obtain a composition, and the influence of the obtained composition on tumor-bearing mouse models was examined.

Specifically, first, a composition containing a human antibody κ type light chains was prepared in the same manner as in C51 (Lot1) of Example 4. Subsequently, copper ions were added to a human antibody κ type light chain solution in which the final concentration of this human antibody κ type light chain was adjusted to 40 μM, and incubation was carried out for 24 hours. After the incubation, dialysis was repeatedly performed using PBS (pH 7.4) at 4° C. for 12 hours twice to obtain a complex-containing composition.

Subsequently, as in the above "cytotoxicity assay in tumor-bearing mouse model", the complex-containing composition or PBS was administered into the tumor-bearing mouse model to evaluate the cytotoxicity in the tumor-bearing mouse model.

Figure 16:
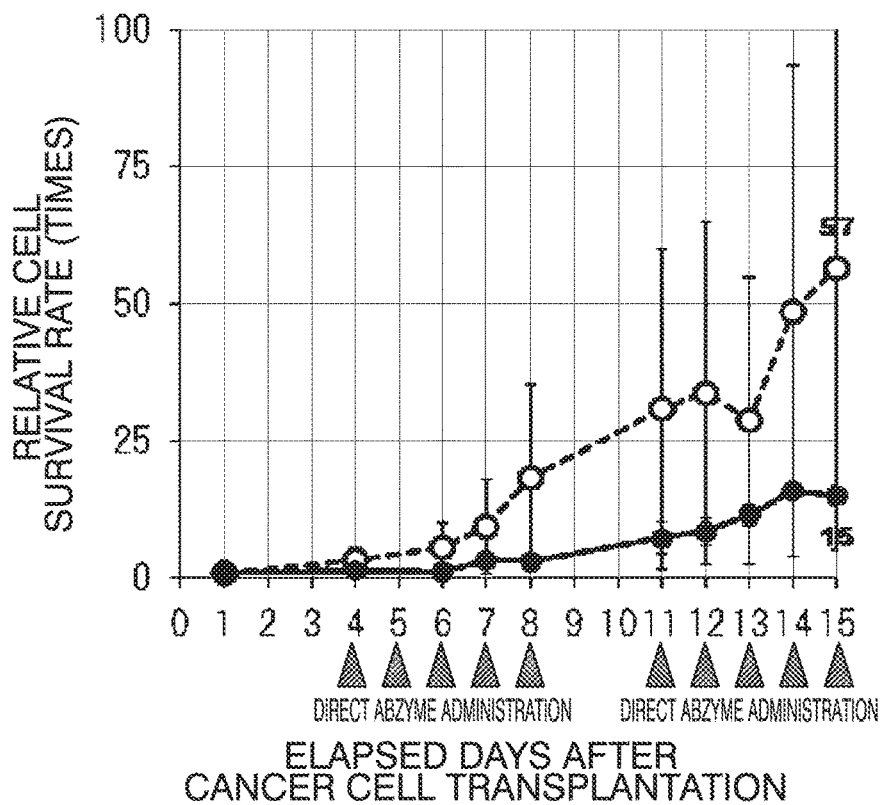
FIG. 16 is a graph showing the time course of relative tumor volume in Example 7, in the case where a human antibody κ type light chain (W15) complex-containing composition was administered to ES-2 cell line-transplanted mice.
Figure 17:
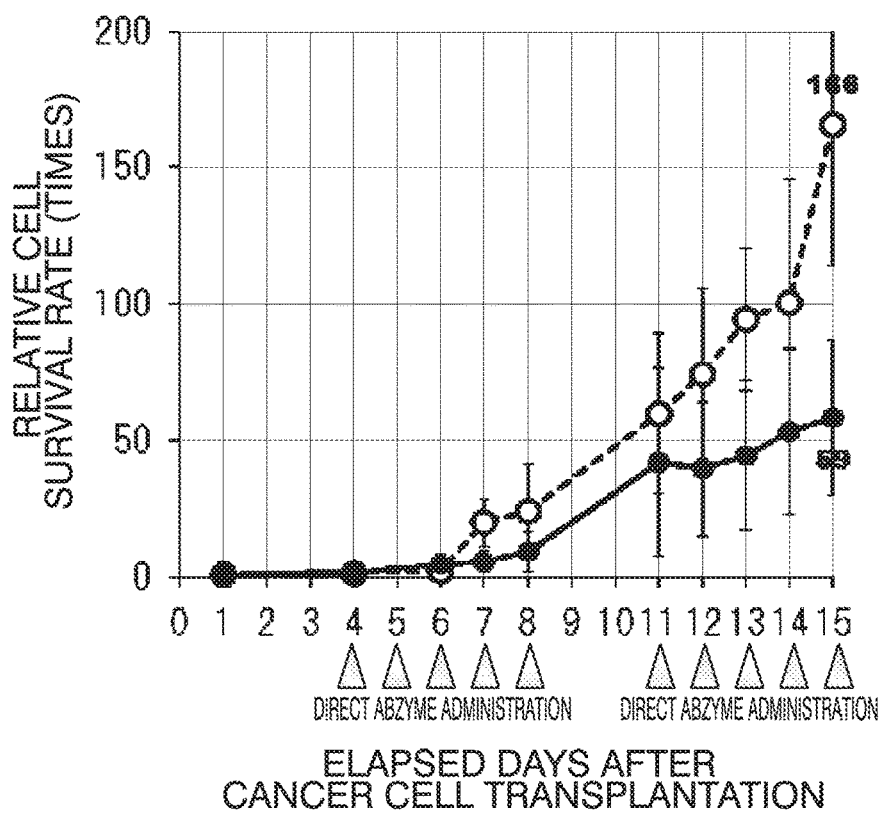
FIG. 17 is a graph showing the time course of relative tumor volume in Example 7, in the case where a human antibody κ type light chain (#4) complex-containing composition was administered to B-16 cell-line-transplanted mice.

FIG. 16 shows the results of administering the complex-containing composition containing the human antibody κ type light chain (W15) into the tumor-bearing mouse obtained by transplanting the ES-2 cell line in an amount of 63.7 μg per mouse (25.5 μM/mouse). FIG. 17 shows the results of administering the complex-containing composition containing the human antibody κ type light chain (#4) into the tumor-bearing mouse obtained by transplanting the B-16 cell line in an amount of 32.3 μg per mouse (12.9 μM/mouse). All in both cases, PBS administration groups are provided as targets. In each group, n=2.

From these results, in the group in which the complex-containing composition containing the human antibody κ type light chain (W15) was administered into the mouse transplanted with the ES-2 cell line, relative tumor volume at 15 days after transplantation remains about ¼, compared to in the control group in which PBS was administered to the mouse, and thus apparent cancer cytotoxicity was observed.

Further, even in the group in which the complex-containing composition containing the human antibody κ type light chain (#4) was administered into the mouse transplanted with the B-16 cell line, relative tumor volume at 15 days after transplantation remains about ⅓, compared to in the control group in which PBS was administered to the mouse, and thus apparent cancer cytotoxicity was observed.

INDUSTRIAL APPLICABILITY

The present invention can be used in the fields of production of pharmaceutical products containing a human antibody κ type light chain as an active ingredient, development of novel anti-cancer drugs, and cancer treatments.

The invention claimed is:

1. A method of treating a cancer comprising administering a human antibody κ type light chain complex-containing composition to a patient in an amount sufficient to cause cytotoxicity to cancer cells, the composition comprising:
   a complex in which a human antibody κ type light chain is bound to one or more kinds of metal ions selected from the group consisting of Group 10 elements, Group 11 elements, and Group 12 elements,
   wherein the human antibody κ type light chain is a dimer, cysteines at C terminals of two human antibody κ type light chains are bound to each other through the metal ion, and the human antibody κ type light chain is selected from the group consisting of:
   (1) a polypeptide in which a variable region is represented by the amino acid sequence of SEQ ID NO. 1;
   (2) a polypeptide in which a variable region is represented by the amino acid sequence of SEQ ID NO. 3;
   (3) a polypeptide in which a variable region is represented by the amino acid sequence of SEQ ID NO. 5;
   (4) a polypeptide in which a variable region is represented by the amino acid sequence of SEQ ID NO. 7;
   (5) a polypeptide in which a variable region is represented by the amino acid sequence of SEQ ID NO. 9;
   (6) a polypeptide in which a variable region is represented by the amino acid sequence of SEQ ID NO. 11;
   (7) a polypeptide in which a variable region is represented by the amino acid sequence of SEQ ID NO. 13;
   (8) a polypeptide in which a variable region is represented by the amino acid sequence of SEQ ID NO. 15;
   (9) a polypeptide in which a variable region is represented by the amino acid sequence of SEQ ID NO. 17;
   (10) a polypeptide in which a variable region is represented by the amino acid sequence of SEQ ID NO. 19;
   (11) a polypeptide in which a variable region is represented by the amino acid sequence of SEQ ID NO. 21;
   (12) a polypeptide in which a variable region is represented by the amino acid sequence of SEQ ID NO. 23;
   (13) a polypeptide in which a variable region is represented by the amino acid sequence of SEQ ID NO. 25;
   (14) a polypeptide in which a variable region is represented by the amino acid sequence of SEQ ID NO. 27;
   (15) a polypeptide which is represented by the amino acid sequence in which cysteine at position 219 in an amino acid sequence of SEQ ID NO. 2 is substituted with alanine;
   (16) a polypeptide in which a variable region is represented by the amino acid sequence of SEQ ID NO. 29;
   (17) a polypeptide in which a variable region is represented by the amino acid sequence of SEQ ID NO. 31;
   (18) a polypeptide in which a variable region is represented by the amino acid sequence of SEQ ID NO. 33;
   (19) a polypeptide in which a variable region is represented by the amino acid sequence of SEQ ID NO. 35;
   (20) a polypeptide in which a variable region is represented by the amino acid sequence of SEQ ID NO. 37;
   (21) a polypeptide in which a variable region is represented by the amino acid sequence of SEQ ID NO. 39;
   (22) a polypeptide in which a variable region is represented by the amino acid sequence of SEQ ID NO. 41;
   (23) a polypeptide in which a variable region is represented by the amino acid sequence of SEQ ID NO. 43;
   (24) a polypeptide in which a variable region is represented by the amino acid sequence of SEQ ID NO. 45;
   (25) a polypeptide in which a variable region is represented by the amino acid sequence of SEQ ID NO. 47;
   (26) a polypeptide in which a variable region is represented by the amino acid sequence of SEQ ID NO. 49; and
   (27) a polypeptide in which a variable region is represented by the amino acid sequence of SEQ ID NO. 51; and
   wherein 0.1 mol or more of the metal ion is bound per 1 mol of the human antibody κ type light chain; and
   the cancer cells are selected from the group consisting of: lung cancer cells, stomach cancer cells, leukemia cells, cancerous T-cells and pancreatic cancer cells.

2. The method of treating a cancer according to claim 1, wherein the metal ion is one or more selected from the group consisting of copper ion, nickel ion, zinc ion, gold ion, silver ion, and platinum ion.

3. The method of treating a cancer according to claim 1, wherein the cancer to be treated is selected from the group consisting of: lung cancer, stomach cancer, leukemia, and pancreatic cancer.

* * * * *

SEQUENCE LISTING

```
<160> NUMBER OF SEQ ID NOS: 53

<210> SEQ ID NO 1
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (#7_wt)

<400> SEQUENCE: 1

Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Arg Thr Phe Gly Gln Gly Thr Lys Val Glu Ile Lys
            100                 105                 110

<210> SEQ ID NO 2
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (#7_wt)

<400> SEQUENCE: 2

Asp Val Val Met Thr Gln Ser Pro Leu Ser Leu Pro Val Thr Pro Gly
```

```
                  1               5                  10                  15
            Glu Pro Ala Ser Ile Ser Cys Arg Ser Ser Gln Ser Leu Leu His Ser
                            20                  25                  30

Asn Gly Tyr Asn Tyr Leu Asp Trp Tyr Leu Gln Lys Pro Gly Gln Ser
                        35                  40                  45

Pro Gln Leu Leu Ile Tyr Leu Gly Ser Asn Arg Ala Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Met Gln Ala
                            85                  90                  95

Leu Gln Thr Pro Arg Thr Phe Gly Gln Gly Thr Lys Val Glu Ile Lys
                        100                 105                 110

Arg Thr Val Ala Ala Pro Ser Val Phe Ile Phe Pro Pro Ser Asp Glu
                    115                 120                 125

Gln Leu Lys Ser Gly Thr Ala Ser Val Val Cys Leu Leu Asn Asn Phe
                130                 135                 140

Tyr Pro Arg Glu Ala Lys Val Gln Trp Lys Val Asp Asn Ala Leu Gln
            145                 150                 155                 160

Ser Gly Asn Ser Gln Glu Ser Val Thr Glu Gln Asp Ser Lys Asp Ser
                            165                 170                 175

Thr Tyr Ser Leu Ser Ser Thr Leu Thr Leu Ser Lys Ala Asp Tyr Glu
                        180                 185                 190

Lys His Lys Leu Tyr Ala Cys Glu Val Thr His Gln Gly Leu Ser Ser
                    195                 200                 205

Pro Val Thr Lys Ser Phe Asn Arg Gly Glu Cys
            210                 215

<210> SEQ ID NO 3
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (#7 VL)

<400> SEQUENCE: 3

Glu Ile Val Met Thr Gln Ser Pro Leu Ser Leu Pro Val Thr Pro Gly
            1               5                  10                  15

Glu Pro Ala Ser Ile Ser Cys Arg Ser Ser Gln Ser Leu Leu His Ser
                            20                  25                  30

Asn Thr Arg Asn Tyr Leu Asp Trp Tyr Leu Gln Lys Pro Gly Gln Ser
                        35                  40                  45

Pro Gln Leu Leu Ile Tyr Leu Gly Ser Asn Arg Ala Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Met Gln Gly
                            85                  90                  95

Leu Gln Thr Pro Arg Thr Phe Gly Gln Gly Thr Lys Val Glu Ile Lys
                        100                 105                 110

<210> SEQ ID NO 4
<211> LENGTH: 219
<212> TYPE: PRT
<213> ORGANISM: human
```

-continued

```
<220> FEATURE:
<221> NAME/KEY: misc_feature
<223> OTHER INFORMATION: Human antibody kappa light chain (#7 VL)

<400> SEQUENCE: 4

Glu Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Thr Arg Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Gly
                85                  90                  95

Leu Gln Thr Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 5
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (#7 VL(I))

<400> SEQUENCE: 5

Glu Ile Val Met Thr Gln Ser Pro Leu Ser Leu Pro Val Thr Pro Gly
1               5                   10                  15

Glu Pro Ala Ser Ile Ser Cys Arg Ser Gln Ser Leu Leu His Ser
            20                  25                  30

Asn Thr Arg Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Met Gln Gly
                85                  90                  95

Leu Gln Thr Pro Ile Thr Phe Gly Gln Gly Thr Lys Val Glu Ile Lys
```

<210> SEQ ID NO 6
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (#7 VL(I))

<400> SEQUENCE: 6

Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Thr Arg Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Leu Gln Thr Pro Ile Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 7
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (#7 VL(RL))

<400> SEQUENCE: 7

Glu Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Thr Arg Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

```
Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Leu Gln Thr Pro Arg Thr Phe Gly Gln Gly Thr Arg Leu Glu Ile Lys
            100                 105                 110

<210> SEQ ID NO 8
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (#7 VL(RL))

<400> SEQUENCE: 8

Glu Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30

Asn Thr Arg Asn Tyr Leu Asp Trp Tyr Leu Gln Lys Pro Gly Gln Ser
             35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Leu Gln Thr Pro Arg Thr Phe Gly Gln Gly Thr Arg Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Leu Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 9
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (#7 RLI)

<400> SEQUENCE: 9

Glu Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Leu His Ser
                 20                  25                  30
```

```
Asn Thr Arg Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Leu Gln Thr Pro Ile Thr Phe Gly Gln Gly Thr Arg Leu Glu Ile Lys
                100                 105                 110

<210> SEQ ID NO 10
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (#7 RLI)

<400> SEQUENCE: 10

Glu Ile Val Met Thr Gln Ser Pro Leu Ser Leu Pro Val Thr Pro Gly
 1               5                  10                  15

Glu Pro Ala Ser Ile Ser Cys Arg Ser Gln Ser Leu Leu His Ser
                20                  25                  30

Asn Thr Arg Asn Tyr Leu Asp Trp Tyr Leu Gln Lys Pro Gly Gln Ser
            35                  40                  45

Pro Gln Leu Leu Ile Tyr Leu Gly Ser Asn Arg Ala Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                85                  90                  95

Leu Gln Thr Pro Ile Thr Phe Gly Gln Gly Thr Arg Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
 130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Leu Tyr Ala Cys Glu Val Thr His Gln Gly Leu Ser Ser
                195                 200                 205

Pro Val Thr Lys Ser Phe Asn Arg Gly Glu Cys
    210                 215

<210> SEQ ID NO 11
<211> LENGTH: 113
<212> TYPE: PRT
<213> ORGANISM: human
<220> FEATURE:
<221> NAME/KEY: misc_feature
<223> OTHER INFORMATION: Variable domain of human antibody kappa light
      chain (#4)
```

<400> SEQUENCE: 11

```
Asp Val Val Met Thr Gln Thr Pro Leu Ser Leu Ser Val Thr Pro Gly
1               5                   10                  15

Glu Pro Ala Ser Ile Ser Cys Arg Ser Thr Gln Ser Leu Leu Asp Ser
            20                  25                  30

Asp Gly Val Asn Pro Ser Phe Asp Trp Tyr Val Gln Lys Pro Gly Gln
        35                  40                  45

Ser Pro Gln Leu Leu Ile His Arg Gly Phe Tyr Arg Ala Ser Gly Val
    50                  55                  60

Pro Asp Arg Phe Ser Gly Ser Gly Ser Gly Thr Asp Phe Thr Leu Arg
65                  70                  75                  80

Ile Ser Arg Val Glu Ala Glu Asp Val Gly Val Tyr Tyr Cys Met Gln
                85                  90                  95

Arg Ile Glu Phe Pro Leu Thr Phe Gly Gly Gly Thr Lys Val Glu Leu
            100                 105                 110

Lys
```

<210> SEQ ID NO 12
<211> LENGTH: 220
<212> TYPE: PRT
<213> ORGANISM: human
<220> FEATURE:
<221> NAME/KEY: misc_feature
<223> OTHER INFORMATION: Human antibody kappa light chain (#4)

<400> SEQUENCE: 12

```
Asp Val Val Met Thr Gln Thr Pro Leu Ser Leu Ser Val Thr Pro Gly
1               5                   10                  15

Glu Pro Ala Ser Ile Ser Cys Arg Ser Thr Gln Ser Leu Leu Asp Ser
            20                  25                  30

Asp Gly Val Asn Pro Ser Phe Asp Trp Tyr Val Gln Lys Pro Gly Gln
        35                  40                  45

Ser Pro Gln Leu Leu Ile His Arg Gly Phe Tyr Arg Ala Ser Gly Val
    50                  55                  60

Pro Asp Arg Phe Ser Gly Ser Gly Ser Gly Thr Asp Phe Thr Leu Arg
65                  70                  75                  80

Ile Ser Arg Val Glu Ala Glu Asp Val Gly Val Tyr Tyr Cys Met Gln
                85                  90                  95

Arg Ile Glu Phe Pro Leu Thr Phe Gly Gly Gly Thr Lys Val Glu Leu
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Leu Tyr Ala Cys Glu Val Thr His Gln Gly Leu Ser
        195                 200                 205

Ser Pro Val Thr Lys Ser Phe Asn Arg Gly Glu Cys
    210                 215                 220
```

```
<210> SEQ ID NO 13
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (#11)

<400> SEQUENCE: 13

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Leu Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Tyr Thr Phe Gly Gln Gly Thr Lys Leu Glu Ile Lys
            100                 105                 110

<210> SEQ ID NO 14
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (#11)

<400> SEQUENCE: 14

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Leu Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Tyr Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190
```

```
Lys His Lys Leu Tyr Ala Cys Glu Val Thr His Gln Gly Leu Ser Ser
            195                 200                 205

Pro Val Thr Lys Ser Phe Asn Arg Gly Glu Cys
            210                 215
```

<210> SEQ ID NO 15
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (23D4)

<400> SEQUENCE: 15

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110
```

<210> SEQ ID NO 16
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (23D4)

<400> SEQUENCE: 16

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160
```

Ser Gly Asn Ser Gln Glu Ser Val Thr Glu Gln Asp Ser Lys Asp Ser
            165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
            210                 215

<210> SEQ ID NO 17
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (W3)

<400> SEQUENCE: 17

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ile
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Thr Glu Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Arg Gln Phe Pro Trp Thr Phe Gly Gln Gly Thr Lys Val Glu Ile Ile
            100                 105                 110

<210> SEQ ID NO 18
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (W3)

<400> SEQUENCE: 18

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ile
            20                  25                  30

Asp Gly Asn Thr Tyr Leu Ser Trp Leu His Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Thr Glu Thr Asp Phe Thr Leu Lys Ile
65                  70                  75                  80

Ser Arg Val Glu Ala Glu Asp Val Gly Ile Tyr Tyr Cys Met Gln Ala
                85                  90                  95

Arg Gln Phe Pro Trp Thr Phe Gly Gln Gly Thr Lys Val Glu Ile Ile
            100                 105                 110

Arg Thr Val Ala Ala Pro Ser Val Phe Ile Phe Pro Pro Ser Asp Glu

```
                115                 120                 125
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
        210                 215

<210> SEQ ID NO 19
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (W10)

<400> SEQUENCE: 19

Asp Ile Val Met Thr Gln Thr Pro Leu Ser Leu Ser Val Thr Pro Gly
1               5                   10                  15

Gln Thr Ala Ser Ile Ser Cys Arg Ser Asp Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile His Glu Leu Ser Ser Arg Leu Ser Gly Val Pro
    50                  55                  60

Glu Arg Phe Ser Gly Ser Gly Ser Gly Thr Glu Phe Thr Leu Lys Ile
65                  70                  75                  80

Ser Arg Val Glu Val Glu Asp Val Gly Ile Tyr Tyr Cys Met Gln Gly
                85                  90                  95

Met Arg Pro Pro Phe Thr Phe Gly Pro Gly Thr Lys Val Asp Ile Lys
            100                 105                 110

<210> SEQ ID NO 20
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (W10)

<400> SEQUENCE: 20

Asp Ile Val Met Thr Gln Thr Pro Leu Ser Leu Ser Val Thr Pro Gly
1               5                   10                  15

Gln Thr Ala Ser Ile Ser Cys Arg Ser Asp Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile His Glu Leu Ser Ser Arg Leu Ser Gly Val Pro
    50                  55                  60

Glu Arg Phe Ser Gly Ser Gly Ser Gly Thr Glu Phe Thr Leu Lys Ile
65                  70                  75                  80
```

```
Ser Arg Val Glu Val Glu Asp Val Gly Ile Tyr Tyr Cys Met Gln Gly
                85                  90                  95

Met Arg Pro Pro Phe Thr Phe Gly Pro Gly Thr Lys Val Asp Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 21
<211> LENGTH: 107
<212> TYPE: PRT
<213> ORGANISM: human
<220> FEATURE:
<221> NAME/KEY: misc_feature
<223> OTHER INFORMATION: Variable domain of human antibody kappa light
      chain (C51)

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Thr Ser Leu Glu Pro
65                  70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys
            100                 105

<210> SEQ ID NO 22
<211> LENGTH: 214
<212> TYPE: PRT
<213> ORGANISM: human
<220> FEATURE:
<221> NAME/KEY: misc_feature
<223> OTHER INFORMATION: Human antibody kappa light chain (C51)

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45
```

```
Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Leu Glu Pro
65              70                  75                  80

Glu Asp Phe Ala Val Tyr Tyr Cys Gln Gln Arg Ser Asp Trp Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 23
<211> LENGTH: 108
<212> TYPE: PRT
<213> ORGANISM: human
<220> FEATURE:
<221> NAME/KEY: misc_feature
<223> OTHER INFORMATION: Variable domain of human antibody kappa light
      chain (C82)

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Gly Pro Phe
            20                  25                  30

Leu Ala Trp Tyr Gln Gln Lys Pro Gly Gln Ala Pro Arg Leu Leu Ile
        35                  40                  45

Tyr Asp Thr Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65              70                  75                  80

Glu Asp Phe Ala Val Tyr Tyr Cys Gln Gln Arg Tyr Thr Trp Pro Gly
                85                  90                  95

Asn Ser Phe Gly Gly Gly Ala Lys Val Glu Ile Lys
            100                 105

<210> SEQ ID NO 24
<211> LENGTH: 215
<212> TYPE: PRT
<213> ORGANISM: human
<220> FEATURE:
<221> NAME/KEY: misc_feature
<223> OTHER INFORMATION: Human antibody kappa light chain (C82)

<400> SEQUENCE: 24

Glu Ile Val Leu Thr Gln Ser Pro Ala Thr Leu Ser Leu Ser Pro Gly
```

-continued

```
                1               5                  10                 15
            Glu Arg Ala Thr Leu Ser Cys Arg Ala Ser Gln Ser Val Gly Pro Phe
                            20                  25                 30

Leu Ala Trp Tyr Gln Gln Lys Pro Gly Gln Ala Pro Arg Leu Leu Ile
                            35                  40                 45

Tyr Asp Thr Ser Thr Arg Ala Thr Gly Ile Pro Ala Arg Phe Ser Gly
                        50                  55                 60

Ser Gly Ser Gly Thr Asp Phe Thr Leu Thr Ile Ser Ser Leu Glu Pro
            65                  70                  75                 80

Glu Asp Phe Ala Val Tyr Tyr Cys Gln Gln Arg Tyr Thr Trp Pro Gly
                            85                  90                 95

Asn Ser Phe Gly Gly Gly Ala Lys Val Glu Ile Lys Arg Thr Val Ala
                            100                 105                110

Ala Pro Ser Val Phe Ile Phe Pro Pro Ser Asp Glu Gln Leu Lys Ser
                            115                 120                125

Gly Thr Ala Ser Val Val Cys Leu Leu Asn Asn Phe Tyr Pro Arg Glu
                        130                 135                 140

Ala Lys Val Gln Trp Lys Val Asp Asn Ala Leu Gln Ser Gly Asn Ser
            145                 150                 155                160

Gln Glu Ser Val Thr Glu Gln Asp Ser Lys Asp Ser Thr Tyr Ser Leu
                            165                 170                175

Ser Ser Thr Leu Thr Leu Ser Lys Ala Asp Tyr Glu Lys His Lys Val
                        180                 185                 190

Tyr Ala Cys Glu Val Thr His Gln Gly Leu Ser Ser Pro Val Thr Lys
                        195                 200                 205

Ser Phe Asn Arg Gly Glu Cys
                        210                 215
```

<210> SEQ ID NO 25
<211> LENGTH: 108
<212> TYPE: PRT
<213> ORGANISM: human
<220> FEATURE:
<221> NAME/KEY: misc_feature
<223> OTHER INFORMATION: Variable domain of human antibody kappa light
      chain (C89)

<400> SEQUENCE: 25

```
            Glu Ile Val Met Thr Gln Ser Pro Gly Thr Leu Ser Leu Ser Pro Gly
            1               5                   10                 15

Glu Arg Ala Thr Leu Ser Cys Arg Ala Ser Pro Ser Val Ser Ser Ser
                            20                  25                 30

Tyr Leu Ala Trp Tyr Gln Gln Lys Pro Gly Gln Ala Pro Arg Leu Leu
                        35                  40                 45

Ile Tyr Gly Ala Ser Ser Arg Ala Thr Gly Ile Ser Asp Arg Phe Ser
                        50                  55                 60

Gly Ser Gly Ser Gly Thr Asp Phe Thr Leu Thr Ile Ser Arg Leu Glu
            65                  70                  75                 80

Pro Glu Asp Phe Ala Val Tyr Tyr Cys Gln Gln Tyr Gly Ser Ser Pro
                            85                  90                 95

Gly Thr Phe Gly Gln Gly Thr Lys Leu Glu Ile Lys
                            100                 105
```

<210> SEQ ID NO 26
<211> LENGTH: 215
<212> TYPE: PRT
<213> ORGANISM: human

<220> FEATURE:
<221> NAME/KEY: misc_feature
<223> OTHER INFORMATION: Human antibody kappa light chain (C89)

<400> SEQUENCE: 26

Glu Ile Val Met Thr Gln Ser Pro Gly Thr Leu Ser Leu Ser Pro Gly
1               5                   10                  15

Glu Arg Ala Thr Leu Ser Cys Arg Ala Ser Pro Ser Val Ser Ser Ser
            20                  25                  30

Tyr Leu Ala Trp Tyr Gln Lys Pro Gly Gln Ala Pro Arg Leu Leu
        35                  40                  45

Ile Tyr Gly Ala Ser Ser Arg Ala Thr Gly Ile Ser Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Gly Thr Phe Gly Gln Gly Thr Lys Leu Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 27
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (W2)

<400> SEQUENCE: 27

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Phe Leu Gln Arg Pro Gly Gln Pro
        35                  40                  45

Pro His Leu Leu Val Tyr Glu Val Phe Lys Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Phe Gly Val Tyr Tyr Cys Met Gln Ser
                85                  90                  95

Thr Gln Leu Pro Leu Ser Phe Gly Gly Gly Thr Lys Val Glu Ile Lys

<210> SEQ ID NO 28
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (W2)

<400> SEQUENCE: 28

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Phe Leu Gln Arg Pro Gly Gln Pro
        35                  40                  45

Pro His Leu Leu Val Tyr Glu Val Phe Lys Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Phe Gly Val Tyr Tyr Cys Met Gln Ser
                85                  90                  95

Thr Gln Leu Pro Leu Ser Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 29
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (W4)

<400> SEQUENCE: 29

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Asn
            20                  25                  30

Asp Gly Asn Ser Tyr Leu Ser Trp Leu His Gln Arg Pro Gly Gln Pro
        35                  40                  45

Pro Arg Leu Leu Ile Tyr Lys Ile Phe Asn Arg Phe Ser Gly Val Pro
    50                  55                  60

```
Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ser
                 85                  90                  95

Thr Gln Phe Pro His Thr Phe Gly Gln Gly Thr Lys Leu Glu Ile Lys
            100                 105                 110

<210> SEQ ID NO 30
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (W4)

<400> SEQUENCE: 30

Asp Ile Val Met Thr Gln Thr Pro Leu Ser Pro Val Thr Leu Gly
 1               5                  10                  15

Gln Pro Ala Ser Ile Ser Cys Arg Ser Gln Ser Leu Val His Asn
             20                  25                  30

Asp Gly Asn Ser Tyr Leu Ser Trp Leu His Gln Arg Pro Gly Gln Pro
             35                  40                  45

Pro Arg Leu Leu Ile Tyr Lys Ile Phe Asn Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Ser
                 85                  90                  95

Thr Gln Phe Pro His Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
        130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 31
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (W7)

<400> SEQUENCE: 31

Asp Ile Val Met Thr Gln Thr Pro Val Ser Leu Ala Val Thr Pro Gly
 1               5                  10                  15

Gln Ser Ala Ser Ile Ser Cys Arg Ser Ser Gln Ser Leu Leu His Gly
             20                  25                  30
```

Asp Gly Arg Ser Tyr Leu Tyr Trp Tyr Val Gln Arg Pro Gly Gln Ser
            35                  40                  45

Pro Gln Leu Leu Met Tyr Glu Ala Ser Thr Arg Val Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Arg
                100                 105                 110

<210> SEQ ID NO 32
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (W7)

<400> SEQUENCE: 32

Asp Ile Val Met Thr Gln Thr Pro Val Ser Leu Ala Val Thr Pro Gly
1               5                   10                  15

Gln Ser Ala Ser Ile Ser Cys Arg Ser Gln Ser Leu Leu His Gly
                20                  25                  30

Asp Gly Arg Ser Tyr Leu Tyr Trp Tyr Val Gln Arg Pro Gly Gln Ser
            35                  40                  45

Pro Gln Leu Leu Met Tyr Glu Ala Ser Thr Arg Val Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Leu Thr Phe Gly Gly Gly Thr Lys Val Glu Ile Arg
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 33
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (W8)

<400> SEQUENCE: 33

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Val Gln Lys Pro Gly Gln Ser
        35                  40                  45

Pro Gln Val Leu Ile Tyr Glu Ala Ser Gly Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Gly
                85                  90                  95

Ile His Ile Pro Ala Thr Phe Gly Gln Gly Thr Arg Val Glu Ile Lys
            100                 105                 110

<210> SEQ ID NO 34
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (W8)

<400> SEQUENCE: 34

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Val Gln Lys Pro Gly Gln Ser
        35                  40                  45

Pro Gln Val Leu Ile Tyr Glu Ala Ser Gly Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Ile Tyr Tyr Cys Met Gln Gly
                85                  90                  95

Ile His Ile Pro Ala Thr Phe Gly Gln Gly Thr Arg Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 35
<211> LENGTH: 112

```
<212> TYPE: PRT
<213> ORGANISM: human
<220> FEATURE:
<221> NAME/KEY: misc_feature
<223> OTHER INFORMATION: Variable domain of human antibody kappa light
      chain (W11)

<400> SEQUENCE: 35

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Ser Arg Thr Phe Gly Gln Gly Thr Lys Val Glu Ile Lys
            100                 105                 110

<210> SEQ ID NO 36
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (W11)

<400> SEQUENCE: 36

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Ser Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205
```

```
Pro Val Thr Lys Ser Phe Asn Arg Gly Glu Cys
    210                 215
```

<210> SEQ ID NO 37
<211> LENGTH: 113
<212> TYPE: PRT
<213> ORGANISM: human
<220> FEATURE:
<221> NAME/KEY: misc_feature
<223> OTHER INFORMATION: Variable domain of human antibody kappa light
      chain (W14)

<400> SEQUENCE: 37

```
Asp Ile Val Met Thr Gln Ser Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Ala Ser Ser Arg Phe Pro Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Ile Tyr Leu Pro Ala Leu Thr Phe Gly Gly Gly Thr Lys Val Glu Ile
            100                 105                 110

Lys
```

<210> SEQ ID NO 38
<211> LENGTH: 220
<212> TYPE: PRT
<213> ORGANISM: human
<220> FEATURE:
<221> NAME/KEY: misc_feature
<223> OTHER INFORMATION: Human antibody kappa light chain (W14)

<400> SEQUENCE: 38

```
Asp Ile Val Met Thr Gln Ser Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Ala Ser Ser Arg Phe Pro Gly Val Pro
    50                  55                  60

Asp Arg Phe Ile Gly Ser Gly Ser Gly Thr Asp Phe Thr Leu Lys Ile
65                  70                  75                  80

Ser Arg Val Glu Ala Glu Asp Val Gly Ile Tyr Tyr Cys Met Gln Gly
                85                  90                  95

Ile Tyr Leu Pro Ala Leu Thr Phe Gly Gly Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160
```

```
Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
            195                 200                 205

Ser Pro Val Thr Lys Ser Phe Asn Arg Gly Glu Cys
            210                 215                 220

<210> SEQ ID NO 39
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (W15)

<400> SEQUENCE: 39

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Arg Thr Phe Gly Gln Gly Thr Lys Val Glu Ile Lys
            100                 105                 110

<210> SEQ ID NO 40
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (W15)

<400> SEQUENCE: 40

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Arg Thr Phe Gly Gln Gly Thr Lys Val Glu Ile Lys
            100                 105                 110

Arg Thr Val Ala Ala Pro Ser Val Phe Ile Phe Pro Pro Ser Asp Glu
```

```
            115                 120                 125
Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
            210                 215
```

<210> SEQ ID NO 41
<211> LENGTH: 113
<212> TYPE: PRT
<213> ORGANISM: human
<220> FEATURE:
<221> NAME/KEY: misc_feature
<223> OTHER INFORMATION: Variable domain of human antibody kappa light
      chain (W17)

<400> SEQUENCE: 41

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly His Thr Tyr Leu Asp Trp Tyr Leu Gln Lys Pro Gly Gln
        35                  40                  45

Ser Pro Gln Leu Leu Ile Phe Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Val Ser Arg Val Glu Ala Glu Asp Val Gly Met Tyr Tyr Cys Met Gln
                85                  90                  95

Arg Lys Glu Phe Pro Tyr Thr Phe Gly Gln Gly Thr Lys Leu Glu Ile
            100                 105                 110

Lys
```

<210> SEQ ID NO 42
<211> LENGTH: 220
<212> TYPE: PRT
<213> ORGANISM: human
<220> FEATURE:
<221> NAME/KEY: misc_feature
<223> OTHER INFORMATION: Human antibody kappa light chain (W17)

<400> SEQUENCE: 42

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly His Thr Tyr Leu Asp Trp Tyr Leu Gln Lys Pro Gly Gln
        35                  40                  45

Ser Pro Gln Leu Leu Ile Phe Thr Leu Ser Tyr Arg Ala Ser Gly Val
    50                  55                  60

Pro Asp Arg Phe Ser Gly Ser Gly Ser Gly Thr Asp Phe Thr Leu Lys
```

```
                65                  70                  75                  80
Val Ser Arg Val Glu Ala Glu Asp Val Gly Met Tyr Tyr Cys Met Gln
                    85                  90                  95

Arg Lys Glu Phe Pro Tyr Thr Phe Gly Gln Gly Thr Lys Leu Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 43
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (W18)

<400> SEQUENCE: 43

Asp Ile Val Met Thr Gln Thr Pro Leu Ser Ser Pro Val Thr Leu Gly
1               5                   10                  15

Gln Pro Ala Ser Met Ser Cys Arg Ser Ser Gln Ser Leu Val His Pro
                20                  25                  30

Asp Gly Asn Thr Tyr Leu Ser Trp Leu Gln Gln Arg Pro Gly Gln Pro
            35                  40                  45

Pro Arg Leu Leu Ile Tyr Lys Ile Ser Ser Arg Phe Pro Gly Val Pro
50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Met Gln Gly
                    85                  90                  95

Ser Gln Phe Pro Tyr Thr Phe Gly Gly Gly Thr Lys Leu Glu Ile Lys
                100                 105                 110

<210> SEQ ID NO 44
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (W18)

<400> SEQUENCE: 44

Asp Ile Val Met Thr Gln Thr Pro Leu Ser Ser Pro Val Thr Leu Gly
1               5                   10                  15

Gln Pro Ala Ser Met Ser Cys Arg Ser Ser Gln Ser Leu Val His Pro
                20                  25                  30
```

```
Asp Gly Asn Thr Tyr Leu Ser Trp Leu Gln Gln Arg Pro Gly Gln Pro
         35                  40                  45

Pro Arg Leu Leu Ile Tyr Lys Ile Ser Ser Arg Phe Pro Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Met Gln Gly
                 85                  90                  95

Ser Gln Phe Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 45
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (W19)

<400> SEQUENCE: 45

Asp Ile Val Met Thr Gln Thr Pro Val Thr Leu Pro Val Thr Pro Gly
 1               5                  10                  15

Glu Pro Ala Ser Ile Ser Cys Arg Ser Gln Ser Leu Leu Asp Ser
                 20                  25                  30

Asp Asp Gly Asn Thr Tyr Leu Asp Trp Tyr Leu Gln Lys Pro Gly Gln
                 35                  40                  45

Ser Pro Gln Leu Leu Ile Tyr Thr Leu Ser Tyr Arg Ala Ser Gly Val
 50                  55                  60

Pro Asp Arg Phe Ser Gly Ser Gly Ser Gly Thr Asp Phe Thr Leu Lys
 65                  70                  75                  80

Ile Ser Arg Val Glu Ala Glu Asp Ile Gly Val Tyr Tyr Cys Met Gln
                 85                  90                  95

Asn Leu Arg Leu Pro Thr Phe Gly Gly Gly Thr Lys Val Asp Ile Lys
                100                 105                 110

<210> SEQ ID NO 46
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (W19)

<400> SEQUENCE: 46
```

```
Asp Ile Val Met Thr Gln Thr Pro Val Thr Leu Pro Val Thr Pro Gly
1               5                   10                  15

Glu Pro Ala Ser Ile Ser Cys Arg Ser Ser Gln Ser Leu Leu Asp Ser
            20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
50                  55                  60

Pro Asp Arg Phe Ser Gly Ser Gly Thr Asp Phe Thr Leu Lys
65                  70                  75                  80

Ile Ser Arg Val Glu Ala Glu Asp Ile Gly Val Tyr Tyr Cys Met Gln
                85                  90                  95

Asn Leu Arg Leu Pro Thr Phe Gly Gly Gly Thr Lys Val Asp Ile Lys
            100                 105                 110

Arg Thr Val Ala Ala Pro Ser Val Phe Ile Phe Pro Pro Ser Asp Glu
            115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
210                 215

<210> SEQ ID NO 47
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (W21)

<400> SEQUENCE: 47

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
            35                  40                  45

Pro Arg Leu Leu Ile Tyr Lys Ile Ser Asn Arg Phe Ser Gly Val Pro
50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Ala Gln Thr
                85                  90                  95

Thr His Phe Pro Pro Thr Phe Gly Gln Gly Thr Lys Val Glu Ile Lys
            100                 105                 110

<210> SEQ ID NO 48
<211> LENGTH: 219
```

```
<212> TYPE: PRT
<213> ORGANISM: human
<220> FEATURE:
<221> NAME/KEY: misc_feature
<223> OTHER INFORMATION: Human antibody kappa light chain (W21)

<400> SEQUENCE: 48

Asp Ile Val Met Thr Gln Thr Pro Leu Ser Ser Pro Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Ser Trp Leu Gln Gln Arg Pro Gly Gln Pro
        35                  40                  45

Pro Arg Leu Leu Ile Tyr Lys Ile Ser Asn Arg Phe Ser Gly Val Pro
    50                  55                  60

Asp Arg Phe Ser Gly Ser Gly Ala Gly Thr Asp Phe Thr Leu Lys Ile
65                  70                  75                  80

Ser Arg Val Glu Ala Glu Asp Val Gly Val Tyr Tyr Cys Ala Gln Thr
                85                  90                  95

Thr His Phe Pro Pro Thr Phe Gly Gln Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 49
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (W26)

<400> SEQUENCE: 49

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Val Leu Ile Tyr Glu Val Ser Ser Arg Phe Ser Gly Val Pro
    50                  55                  60

Asp Arg Val Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95
```

-continued

```
Ile Gln Leu Pro Pro Ser Phe Gly Gly Gly Thr Lys Val Glu Ile Lys
            100                 105                 110

<210> SEQ ID NO 50
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (W26)

<400> SEQUENCE: 50

Asp Ile Val Met Thr Gln Thr Pro Leu Ser Leu Ser Val Thr Pro Gly
1               5                   10                  15

Gln Pro Ala Ser Ile Ser Cys Lys Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Val Leu Ile Tyr Glu Val Ser Ser Arg Phe Ser Gly Val Pro
    50                  55                  60

Asp Arg Val Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ser
                85                  90                  95

Ile Gln Leu Pro Pro Ser Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 51
<211> LENGTH: 112
<212> TYPE: PRT
<213> ORGANISM: human
<220> FEATURE:
<221> NAME/KEY: misc_feature
<223> OTHER INFORMATION: Variable domain of human antibody kappa light
      chain (W28)

<400> SEQUENCE: 51

Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Ser Arg Phe Ser Gly Val Pro
```

```
                 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                     85                  90                  95

Ile His Leu Pro Tyr Thr Phe Gly Gln Gly Thr Lys Leu Glu Ile Lys
                100                 105                 110

<210> SEQ ID NO 52
<211> LENGTH: 219
<212> TYPE: PRT
<213> ORGANISM: human
<220> FEATURE:
<221> NAME/KEY: misc_feature
<223> OTHER INFORMATION: Human antibody kappa light chain (W28)

<400> SEQUENCE: 52

Asp Ile Val Met Thr Gln Thr Pro Leu Ser Leu Ser Val Thr Pro Gly
  1               5                  10                  15

Gln Pro Ala Ser Ile Ser Cys Lys Ser Ser Gln Ser Leu Leu His Ser
                 20                  25                  30

Asp Gly Lys Thr Tyr Leu Tyr Trp Tyr Leu Gln Lys Pro Gly Gln Ser
             35                  40                  45

Pro Gln Leu Leu Ile Tyr Glu Val Ser Ser Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Gly
                     85                  90                  95

Ile His Leu Pro Tyr Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
            130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
            195                 200                 205

Pro Val Thr Lys Ser Phe Asn Arg Gly Glu Cys
    210                 215

<210> SEQ ID NO 53
<211> LENGTH: 8
<212> TYPE: PRT
<213> ORGANISM: Artificial Sequence
<220> FEATURE:
<223> OTHER INFORMATION: Description of Artificial Sequence:Artificially
      Synthesized Sequence

<400> SEQUENCE: 53

Leu Glu His His His His His His
 1               5
```